United States Patent
Wu et al.

(10) Patent No.: US 10,906,920 B2
(45) Date of Patent: *Feb. 2, 2021

(54) HETEROCYCLIC COMPOUNDS AS IMMUNOMODULATORS

(71) Applicant: Incyte Corporation, Wilmington, DE (US)

(72) Inventors: Liangxing Wu, Wilmington, DE (US); Kaijiong Xiao, Clark, NJ (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/810,154

(22) Filed: Mar. 5, 2020

(65) Prior Publication Data

US 2020/0277309 A1 Sep. 3, 2020

Related U.S. Application Data

(63) Continuation of application No. 16/409,026, filed on May 10, 2019, now Pat. No. 10,618,916.

(60) Provisional application No. 62/670,249, filed on May 11, 2018, provisional application No. 62/688,164, filed on Jun. 21, 2018.

(51) Int. Cl.
*C07D 471/04* (2006.01)
*A61K 31/437* (2006.01)
*C07D 519/00* (2006.01)
*A61P 37/04* (2006.01)

(52) U.S. Cl.
CPC ............ *C07D 519/00* (2013.01); *A61P 37/04* (2018.01)

(58) Field of Classification Search
CPC .......................... C07D 471/04; A61K 31/437
USPC .......................................... 546/118; 514/303
See application file for complete search history.

(56) References Cited

U.S. PATENT DOCUMENTS

| | | | |
|---|---|---|---|
| 3,272,781 A | 9/1966 | Goodrow | |
| 4,208,328 A | 6/1980 | Lavallee | |
| 4,789,711 A | 12/1988 | Monnier et al. | |
| 5,077,164 A | 12/1991 | Ueda et al. | |
| 6,114,497 A | 9/2000 | Tada et al. | |
| 6,297,351 B1 | 10/2001 | Murayama et al. | |
| 6,372,907 B1 | 4/2002 | Lee et al. | |
| 6,521,618 B2 | 2/2003 | Boschelli et al. | |
| 6,867,200 B1 | 3/2005 | Allen et al. | |
| 7,320,989 B2 | 1/2008 | Anderson et al. | |
| 8,541,424 B2 | 9/2013 | DeGoey et al. | |
| 8,993,604 B2 | 3/2015 | Byrd et al. | |
| 9,163,017 B2 | 10/2015 | DeGoey et al. | |
| 9,540,322 B2 | 1/2017 | Jorgensen et al. | |
| 9,643,922 B2 | 5/2017 | Jorgensen et al. | |
| 10,017,520 B2 | 7/2018 | Koehler et al. | |
| 10,202,343 B2 | 2/2019 | Jorgensen et al. | |
| 10,308,644 B2 | 6/2019 | Wu et al. | |
| 10,618,916 B2 | 4/2020 | Wu et al. | |
| 10,669,271 B2 | 6/2020 | Wu et al. | |
| 10,793,505 B2 | 10/2020 | Wu et al. | |
| 10,800,768 B2 | 10/2020 | Wu et al. | |
| 2002/0082266 A1 | 6/2002 | Gallant et al. | |

(Continued)

FOREIGN PATENT DOCUMENTS

CA  2355249  6/2000
CL  2018001531  7/2018

(Continued)

OTHER PUBLICATIONS

Abdellaoui et al., "Palladium-catalyzed non-directed C-H bond arylation of difluorobenzenes and dichlorobenzenes bearing benzoxazole or benzothiazole," Catalysis Communications, 2015, 71:13-16.

(Continued)

*Primary Examiner* — Charanjit Aulakh
(74) *Attorney, Agent, or Firm* — Fish & Richardson P.C.

(57) ABSTRACT

Disclosed are compounds of Formula (I), methods of using the compounds as immunomodulators, and pharmaceutical compositions comprising such compounds. The compounds are useful in treating, preventing or ameliorating diseases or disorders such as cancer or infections.

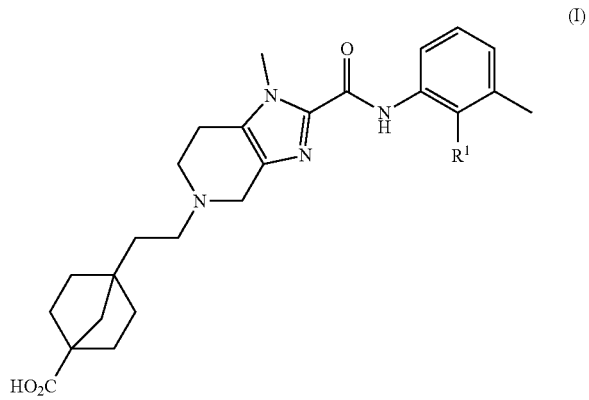

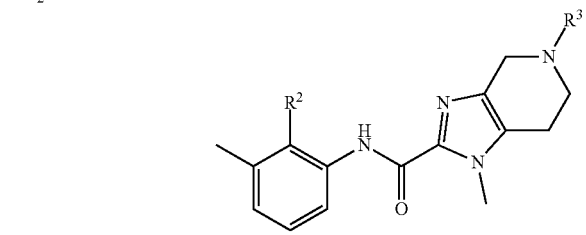

41 Claims, No Drawings

(56) References Cited

U.S. PATENT DOCUMENTS

| | | |
|---|---|---|
| 2003/0134843 A1 | 7/2003 | Lubisch et al. |
| 2004/0058938 A1 | 3/2004 | Cullmann et al. |
| 2004/0063963 A1 | 4/2004 | Ueno et al. |
| 2004/0082635 A1 | 4/2004 | Hashimoto et al. |
| 2004/0186114 A1 | 9/2004 | Cirillo et al. |
| 2004/0214040 A1 | 10/2004 | Lee et al. |
| 2005/0187230 A1 | 8/2005 | Ding et al. |
| 2005/0245536 A1 | 11/2005 | Hao et al. |
| 2005/0260126 A1 | 11/2005 | Kudo et al. |
| 2005/0288295 A1 | 12/2005 | Currie et al. |
| 2006/0004010 A1 | 1/2006 | Habashita et al. |
| 2006/0089362 A1 | 4/2006 | Seno et al. |
| 2006/0178367 A1 | 8/2006 | Currie et al. |
| 2006/0229337 A1 | 10/2006 | Brittelli et al. |
| 2006/0270686 A1 | 11/2006 | Kelly et al. |
| 2007/0099938 A1 | 5/2007 | Ohmoto et al. |
| 2007/0191395 A1 | 8/2007 | Kawakami et al. |
| 2008/0139557 A1 | 6/2008 | Blomgren et al. |
| 2008/0153834 A1 | 6/2008 | Blomgren et al. |
| 2008/0280891 A1 | 11/2008 | Kelly et al. |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa, Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0229816 A1 | 8/2016 | Sato et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0283423 A1 | 9/2020 | Yu et al. |

FOREIGN PATENT DOCUMENTS

| | | |
|---|---|---|
| CL | 2018003734 | 2/2019 |
| CL | 2018003697 | 5/2019 |
| CN | 101891895 | 11/2010 |
| CN | 103933036 | 7/2014 |
| CN | 104045552 | 9/2014 |
| CN | 104211726 | 12/2014 |
| EP | 0644460 | 3/1995 |
| EP | 1505068 | 2/2005 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004294556 | 10/2004 |
| JP | 2005002330 | 1/2005 |
| JP | 2005248082 | 9/2005 |
| JP | 2005290301 | 10/2005 |
| JP | 2006-290883 A | 10/2006 |
| JP | 2008218327 | 9/2008 |
| JP | 2010202530 | 9/2010 |
| JP | 2013084945 | 5/2013 |
| JP | 2015155397 | 8/2015 |
| JP | 2015193612 | 11/2015 |
| JP | 2016135778 | 7/2016 |
| KR | 1715090 | 3/2015 |
| KR | 1717601 | 12/2015 |
| KR | 1653560 | 2/2016 |
| WO | WO 98/27108 | 6/1998 |
| WO | WO 1999/018096 | 4/1999 |
| WO | WO 99/44992 A1 | 9/1999 |
| WO | WO 00/35886 | 6/2000 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |

(56) References Cited

FOREIGN PATENT DOCUMENTS

| | | |
|---|---|---|
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/031587 | 4/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2005/000833 | 1/2005 |
| WO | WO 2005/014543 | 2/2005 |
| WO | WO 2005/023761 | 3/2005 |
| WO | WO 2005/034869 | 4/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/050803 | 5/2006 |
| WO | WO 2006/053121 | 5/2006 |
| WO | WO 2006/094235 | 9/2006 |
| WO | WO 2006/125101 | 11/2006 |
| WO | WO 2007/004954 | 1/2007 |
| WO | WO 2007/034282 | 3/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/027812 | 3/2008 |
| WO | WO 2008/033854 | 3/2008 |
| WO | WO 2008/033857 | 3/2008 |
| WO | WO 2008/033858 | 3/2008 |
| WO | WO 2008/062182 | 5/2008 |
| WO | WO 2008/104077 | 9/2008 |
| WO | WO 2008/104278 | 9/2008 |
| WO | WO 2008/104279 | 9/2008 |
| WO | WO 2008/118122 | 10/2008 |
| WO | WO 2008/134553 | 11/2008 |
| WO | WO 2008/141249 | 11/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/077197 | 6/2009 |
| WO | WO 2009/079683 | 7/2009 |
| WO | WO 2009/106539 | 9/2009 |
| WO | WO 2009/123986 | 10/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/104306 | 9/2010 |
| WO | WO 2010/115736 | 10/2010 |
| WO | WO 2010/119264 | 10/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |

(56) References Cited

FOREIGN PATENT DOCUMENTS

| | | |
|---|---|---|
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |

OTHER PUBLICATIONS

Ahmed et al., "Enantioselective Polymerization of Epoxides Using Biaryl-Linked Bimetallic Cobalt Catalysts: A Mechanistic Study," J Am Chem Soc., 2013, 135(50):18901-18911.
Amaya et al., "Synthesis of three-dimensionally arranged bis-biphenol ligand on hexaaryl benzene scaffold and its application for cross-pinacol coupling reaction," Tetrehedron Letters, 2011, 52(35):4567-4569.
Anyika et al., "Point-to-Axial Chirality Transfer—A New Probe for "Sensing" the Absolute Configurations of Monoamines," J Am Chem Soc., 2014, 136(2):550-553.
Arkin et al., "Small-Molecule Inhibitors of Protein-Protein Interactions: Progressing toward the Reality," Chemistry & Biology, Sep. 2014, 21:1102-1114.
Arkin et al., "Small-Molecule Inhibitors of Protein—Protein Interactions: Progressing Towards the Dream," Nature Reviews, Apr. 2004, 3:301-317.
Artz et al., "Host-guest complexation. 28. Hemispherands with four self-organizing units," J Am Chem Soc., 1984, 106(7):2160-2171.
Atzrodt et al., The Renaissance of H/D Exchange, Angew Chem Int Ed., 2007, 7744-7765.
Barakat, "Do We Need Small Molecule Inhibitors for the Immune Checkpoints?" J. Pharma. Care Health Sys., 2014, 1(4):1000e119.
Bather et al, "Restoring function in exhausted CD8 T cells during chronic viral infection," Nature, Feb. 2006, 439:682-687.
Bentley et al., "Antenna Biphenols: Development of Extended Wavelength Chiroptical Reporters," J Org Chem., 2016, 81(3):1185-1191.
Berg, "Modulation of Protein—Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al, "PD-L1/B7H-1 Inhibits the Effector Phase of Tumor Rejection by T Cell Receptor (TCR) Transgenic CD8+ T Cells," Cancer Res., Feb. 2004, 64(3):1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J. Combi. Chem., Nov. 2004, 6:874-883.
Blom, "Two-Pump At Column Dilution Configuration for Preparative LC-MS", K. Blom, J. Combi. Chem., 2002, 4:295-301.
Bross et al., "Radiation damage to 2-(2'-hydroxyphenyl)benzothiazoles," Radiation Physics and Chemistry, Jul. 1992, 41:379-387.

Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.
Carter et al, "PD-1:PD-L inhibitory pathway affects both CD4+ and CD8+ T cells and is overcome By IL-2," Eur. J. Immunol., 2002, 32(3):634-643.
Chang et al., "Blocking of the PD-1/PD-L1 Interaction by a d-Peptide Antagonist for Cancer Immunotherapy," Angew. Chem. Int. Ed., 2015, 127(40):11926-11930.
Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.
Chen et al., "Anti-PD-1/PD-L1 therapy of human cancer: past, present, and future," J. Clin. Invest., Sep. 2015, 125(9):3384-3391.
Cheng et al., "Synthetic connections to the aromatic directed metalation reaction. Iterative orthometalation-cross coupling tactics for the construction of polyphenyls," Tetrahedron Letters, 1978, 28(43):5097-5098.
Cheng et al., "Recent Advances in Small Molecule Based Cancer Immunotherapy," Eur J Med Chem., 2018, 157:582-598.
Cheng et al., "Structure and Interactions of the Human Programmed Cell Death 1 Receptor," J. Bio. Chem., Apr. 2013, 288(17):11771-11785.
Chilean Office Action in Chilean Application No. 201801685, dated Aug. 20, 2019, 18 pages.
Chilean Office Action in Chilean Application No. 201803701, dated Nov. 22, 2019, 18 pages.
Chilean Office Action in Chilean Application No. 201901744, dated Apr. 14, 2020, 19 pages.
Clayden et al., "Conformational Preference and Remote (1,10) Stereocontrol in Biphenyl-2,2'—dicarboxamides," Org. Lett., 2001, 3(26):4133-4136.
Cram et al., "Host-guest complexation. 32. Spherands composed of cyclic urea and anisyl units," J Am Chem Soc., 1984, 106(23):7150-7167.
Cram et al., "Host-guest complexation. 29. Expanded hemispherands," J Am Chem Soc., 1984, 106(11):6386-3292.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database Accession No. 1590700-72-3 abstract, Apr. 27, 2014, 1 page.
Database Accession No. 1581556-71-9 abstract, Apr. 8, 2014, 1 page.
Database Accession No. 1580823-55-7 abstract, Apr. 6, 2014, 1 page.
Database Accession No. 1568738-04-4 abstract, Mar. 14, 2014, 1 page.
Database accession No. 1478989-52-4 abstract, Nov. 22, 2013, 1 page.
Database accession No. 2013:447446 abstract, 2013, 1 page.
De Lucca et al., "Small Molecule Reversible Inhibitors of Bruton's Tyrosine Kinase (BTK): Structure-Activity Relationships Leading to the Identification of 7-(2-Hydroxypropan-2-yl)-4[2-methyl-3-(4-oxo-3,4-dihydroquinazolin-3-yl)phenyl]-9H-carbazole-1-carboxamide (BMS-935177),"Journal of Medicinal Chemistry, 2016, 59(17):7915-7935.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dhanunjayarao et al., "Synthesis and Optical Properties of Salicylaldimine-Based Diboron Complexes," Eur J Inorg Chem., 2014, 3:539-545.
Dolan et al., "PD-1 Pathway Inhibitors: Changing the Landscape of Cancer Immunotherapy," Cancer Control, Jul. 2014, 21(3):231-237.

(56) References Cited

OTHER PUBLICATIONS

Domling et al., "Programmed Death-1: Therapeutic Success after More than 100 Years of Cancer Immunotherapy," Angew. Chem. Int. Ed., 2014, 53:2283-2288.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jul. 10, 2018, 6 pages.
European Communication in European Application No. 16805690.1, dated Jan. 22, 2020, 5 pages.
European Communication in European Application No. 17743174.9, dated Jan. 31, 2020, 5 pages.
Fabris et al., "Central to Axial Transfer of Chirality in Menthone or Camphor-Derived 2,2'—Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al, "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands. Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regio specific dimerization of aromatic acids: two direct C-H bond activations in water," Angewandte Chemie, 2015, 54(19):5718-5721.
Goswami et al., "A turn on ESIPT probe for rapid and ratiometric fluorogenic detection of homocysteine and cysteine in water with live cell-imaging," Tetrahedron Letters, 2014, 55(2):490-494.
Green et al., "Synthesis and investigation of the configurational stability of some dimethylammonium borate salts," J. Chem. Soc., Perkin Trans. 1, 2000, 24:4403-4408.
Greenwald et al, "The B7 Family Revisited," Annu. Rev. Immunol., 2005, 23:515-548.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Hu et al., "Novel highly active binuclear neutral nickel and palladium complexes as precatalysts for norbornene polymerization," Journal of Molecular Catalysis A: Chemical 253, 2006, 155-164.
Huang et al, "The prognostic significance of PD-L1 in bladder cancer," Oncol. Rep., 2015, 33:3075-3084.
Huddle et al., "Reactions of alkyl-lithium compounds with aryl halides ," J Chem Soc., Perkin I, 1980, 12:2617-2625.
HuGEMM™ and HuCELL™ Models, "FactSheet," CrownBio, Oct. 2016, 8 pages.
Indian Office Action with Indian Application No. 201817026809, dated Apr. 29, 2020, 6 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/041899, dated Jan. 15, 2019, 7 pages.
International Preliminary Report on Patentability in International Application No. PCT/US2017/048880, dated Mar. 5, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067951, dated Jun. 25, 2019, 8 pages.
International Preliminary Report on Patentability in International Application No. PCT/US2017/067880, dated Jun. 25, 2019, 7 pages.
International Preliminary Report on Patentability in International Application No. PCT/US2017/067984, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067886, dated Jun. 25, 2019, 9 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067925, dated Mar. 27, 2017, 13 pages.
International Search Report and Written Opinion in International Application No. PCT/US2016/067155, dated Apr. 24, 2017, 26 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/041899, dated Sep. 5, 2017, 12 pages.
International Search Report and Written Opinion in International Application No. PCT/US2017/038120, dated Aug. 1, 2017, 14 pages.

(56) References Cited

OTHER PUBLICATIONS

International Search Report and Written Opinion in International Application No. PCT/US2017/067904, dated Mar. 22, 2018, 14 pages.
International Search Report and Written Opinion in International Application No. PCT/US2017/067880, dated Mar. 21, 2018, 13 pages.
International Search Report and Written Opinion in International Application No. PCT/US2017/067984, dated Mar. 22, 2018, 14 pages.
International Search Report and Written Opinion in International Application No. PCT/US2017/067886, dated Mar. 23, 2018, 24 pages.
International Search Report and Written Opinion in International Application No. PCT/US2017/067946, dated May 22, 2018, 16 Pages.
International Search Report and Written Opinion in International Application No. PCT/US2017/067951, dated Mar. 27, 2018, 15 pages.
International Search Report and Written Opinion in International Application No. PCT/US2017/048880, dated Oct. 23, 2017, 15 pages.
International Search Report and Written Opinion in International Application No. PCT/US2019/031728, dated Jun. 25, 2019, 12 pages.
International Search Report and Written Opinion in International Application No. PCT/US2019/025036, dated Jul. 3, 2019, 12 pages.
Israeli Office Action in Israeli Application No. 259,406, dated Mar. 11, 2020, 10 pages.
Iwai et al, "Involvement of PD-L1 on tumor cells in the escape from host immune system and tumor immunotherapy by PD-L1 blockade," PNAS, Sep. 2002, 99(19):12293-12297.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides, " J Org Chem., 1993, 58(6):1409-1414.
Komiyama et al, "IL-17 Plays an Important Role in the Development of Experimental Autoimmune Encephalomyelitis," J. Immunol., Jul. 2006, 177:566-73.
Latchman et al, "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.

Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of the Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al, "Autoimmune Dilated Cardiomyopathy in PD-1 Receptor-Deficient Mice," Science, Jan. 2001, 291:319-322.
Nishimura et al, "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," TRENDS in Immunology, May 2001, 22(5):265-268.
Nishino et al., "Copper-Mediated C-H/C-H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al., "Facile syntheses and multi-orthofunctionalizations of tertiary benzamides," Bulletin of the Korean Chemical Society, 1993, 14(6):732-739.

(56) References Cited

OTHER PUBLICATIONS

Paek et al., "Chiral host. Attempted synthesis using McMurray reaction as a final ring closure method," Bulletin of the Korean Chemical Society, 1989, 10(6):572-577.
Pardoll, "The blockade of immune checkpoints in cancer immunotherapy," Nature, Apr. 2012, 12:252-264.
Parry et al, "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Postow et al, "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Sabatier et al, "Prognostic and predictive value of PDL1 expression in breast cancer," Oncotarget, Mar. 2015, 6(7):5449-5464.
Sharpe et al, "The function of programmed cell death 1 and its ligands in regulating autoimmunity and infection," Nat. Immunol., Mar. 2007 8(3):239-245.
Sharpe et al., "The B7—CD28 Superfamily," Nature Reviews, Feb. 2002, 2:116-126.
Sharma et al., "Palladium-Catalyzed Decarboxylative Acylation of O-Phenyl Carbamates with Alpha-Oxocalboxylic Acids at Room Temperature," Advanced Synthesis & Catalysis, 2013, 355(4):667-672.
STN Search Report dated Apr. 14, 2016, 79 pages.
STN Search Report dated Apr. 29, 2016, 69 pages.
STN Search Report dated Aug. 30, 2016, 4 pages.
STN Search Report dated Jun. 6, 2016, 115 pages.
STN Search Report dated Sep. 2, 2016, 115 pages.
STN Search Report, dated May 1, 2016, 12 pages.
STN Search Report dated May 24, 2016, 92 pages.
STN Search Report dated Sep. 12, 2016, 4 pages.
STN Search Report dated Jun. 16, 2016, 8 pages.
STN Search Report dated Sep. 12, 2016, 17 pages.
STN Search Report dated Jul. 12, 2016, 4 pages.
STN Search Report dated Aug. 19, 2016, 23 pages.
STN Search Report dated Dec. 15, 2016, 4 pages.
STN Search Report dated Dec. 19, 2016, 11 pages.
STN Search Report dated Dec. 16, 2016, 25 pages.
STN Search Report dated Dec. 16, 2016, 4 pages.
STN Search Report dated Dec. 20, 2016, 117 pages.
STN Search Report dated Sep. 27, 2017, 4 pages.
STN Search Report dated Mar. 27, 2018, 4 pages.
STN Search Report dated Apr. 30, 2018, 8 pages.
Sorrell et al., "3,3'-Disubstituted 2,2'-biphenols. Synthesis of nonplanar, tetradentate chelating ligands," J Org Chem., 1985, 50(26):5765-5769.
Storz, "Intellectual property issues of immune checkpoint inhibitors," mAbs, Jan. 2016, 8(1):10-26.
Sumrit et al., "Aluminum complexes containing salicylbenzoxazole ligands and their application in the ring-opening polymerization of rac-lactide and E-caprolactone," Dalton Transactions (2016), 45(22), 9250-9266.
Tang et al., "Facile synthesis of enantioenriched phenol-sulfoxides and their aluminum complexes," Org Biomol Chem., 2016, 14(24):5580-5585.
Thiel et al., "Small-Molecule Stabilization of Protein—Protein Interactions: An Underestimated Concept in Drug Discovery?" Angew. Chem. Int. Ed., 2012, 51:2012-2018.
Tucker et al., "Host-guest complexation. 52. Bridged and chiral hemispherands," J Org Chem., 1989, 54(23):5460-5482.
Unrau et al., "Directed ortho metalation. Suzuki cross coupling connections. Convenient regiospecific routes to functionalized m- and p-terraryls and m-quinquearyls," Tetrahedron Letters, 1992, 33(20):2773-2776.
Velcheti et al., "Programmed death-1/programmed death-1 ligand axis as a therapeutic target in oncology: current insights," Journal of Receptor Ligand and Channel Research, Dec. 2014, 8(23): 1-7.
Wang et al, "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatics and color: Massive electrostatic perturbation of chromophores by ion cluster ligands," J Am Chem Soc., 2007, 129(3):547-553.
Weiss et al., "Electrostatic activation of SNAr-reactivity by sulfonylonio substituents," Zeitschrift fuer Naturforschung, 2001, 56(12):1360-1368 English Abstract.
Weiss et al., "First-ever per(onio) substitution of benzene: the role of the counterion," Angewandte Chemie, 1995, 34(12):1319-1321.
Weiss et al., "Massive electrostatic effects on heteropolar C-C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein—protein interfaces," Nature, Dec. 2007, 450:1001-1009.
Wu et al., "Targeting the BACE1 Active Site Flap Leads to a Potent Inhibitor That Elicits Robust Brain Aβ Reduction in Rodents," ACS Medicinal Chemistry Letters, 2016, 7(3):271-276.
www.medscape.com' [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.

(56) References Cited

OTHER PUBLICATIONS

Xu et al., "Quantitative structure-activity relationship study on BTK inhibitors by modified multivariate adaptive regression spline and CoMSIA methods," SAR QSAR Environ Res., 2015, 26(4):279-300.

Xu et al., "Design, synthesis and biological evaluation of deuterated nintedanib for improving pharmacokinetic properties," J Label Compd RadioPharm., Jun. 15, 2015, 58(7):308-312.

Yin et al., "Strategies for Targeting Protein—Protein Interactions With Synthetic Agents," Angew. Chem. Int. Ed., 2005, 44:4130-4163.

Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.

Young et al., "Potent and selective Bruton's tyrosine kinase inhibitors: Discovery of GDC-0834," Bioorganic & Medicinal Chemistry Letters , 2015, 25(6):1333-1337.

Zarganes-Tzitzikas, "Inhibitors of programmed cell death 1 (PD-1): a patent review (2010-2015)," Expert Opinion on Therapeutic Patents, Sep. 19, 2016, 26(9):973-977.

Zak et al., "Structural basis for small molecule targeting of the programmed death ligand 1 (PD-L1)," Oncotarget, 2016, 7(21):30323-30335.

Zak et al., "Structural basis for small molecule targeting of the programmed death ligand 1 (PD-L1)" Oncotarget, Apr. 2016, 19 pages; Supplemental Material for 2016, 7(21):30323-30335.

Zak et al., "Structure of the Complex of Human Programmed Death 1, PD-1, and Its Ligand PD-L1: with Supplemental Information," Structure, Dec. 2015, 23:2341-2348.

Zang et al., "Four 2D metal-organic networks incorporating Cd-cluster SUBs: hydrothermal synthesis, structures and photoluminescent properties," CrystEngComm, 2009, 11(1):122-129.

Zhan et al., "From monoclonal antibodies to small molecules: the development of inhibitors targeting the PD-1/PD-L1 pathway," Drug Discovery Today, Apr. 2016, 10 pages.

Zhang et al., "Electrospray mass spectrum of a per(onio)-substituted benzene: retention of Coulombic charge upon collisionally activated decomposition," J Am Soc. Mass. Spectrom., 1998, 9(1):15-20.

Zhang et al., "Non-symmetrical diarylcarboxylic acids via rhodium(I)-catalyzed regiospecific cross-dehydrogenation coupling of aromatic acids: twofold direct C-H bond activations in water," RSC Advances, 2016, 6(64):91617-91620.

Zhang et al., "Structural and Functional Analysis of the Costimulatory Receptor Programmed Death-1," Immunity, Mar. 2004, 20:337-347.

Zhang et al., "Biaryl-Based Macrocyclic and Polymeric Chiral (Salophen)Ni(II) Complexes: Synthesis and Spectroscopic Study," J Org Chem., 2001, 66(2):481-487.

Zhao et al., "Design, synthesis and organocatalysis of 2,2'-biphenol-based prolinamide organocatalysts in the asymmetric direct aldol reaction in water," Synlett, 2013, 24(20):2743-2747.

Australian Office Action in Australian Application No. 2016358100, dated May 8, 2020, 5 pages.

Colombian Office Action in Colombian Application No. NC2018/0007528, dated Jun. 30, 2020, 9 pages.

Israeli Office Action in Israeli Application No. 260,166, dated Jun. 2, 2020, 13 pages.

International Preliminary Report on Patentability in International Application No. PCT/US2019/031728, dated Nov. 17, 2020, 7 pages.

HETEROCYCLIC COMPOUNDS AS IMMUNOMODULATORS

The present application is a continuation of U.S. patent application Ser. No. 16/409,026, filed May 10, 2019, which claims the benefit of U.S. Provisional Application No. 62/670,249, filed May 11, 2018; and U.S. Provisional Application No. 62/688,164, filed Jun. 21, 2018, each of which is incorporated herein by reference in its entirety.

FIELD OF THE INVENTION

The present application is concerned with pharmaceutically active compounds. The disclosure provides compounds as well as their compositions and methods of use. The compounds modulate PD-1/PD-L1 protein/protein interaction and are useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is unregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds that block PD-1/PD-L1 protein/protein interaction.

SUMMARY

The present disclosure provides, inter alia, a compound of Formula (I):

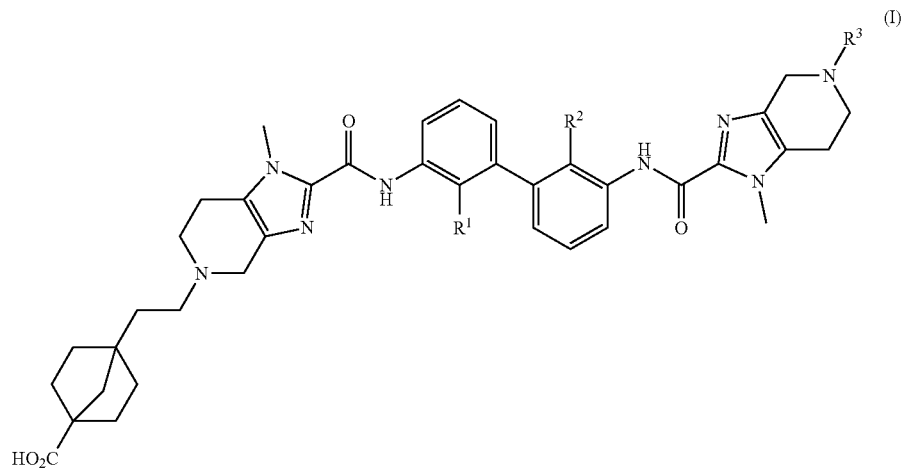

or a pharmaceutically acceptable salt or a stereoisomer thereof, wherein constituent variables are defined herein. The present disclosure further provides a pharmaceutical composition comprising a compound disclosed herein, or a pharmaceutically acceptable salt or a stereoisomer thereof, and one or more pharmaceutically acceptable excipient or carrier.

The present disclosure further provides methods of inhibiting PD-1/PD-L1 interaction, said method comprising administering to a patient a compound disclosed herein, or a pharmaceutically acceptable salt or a stereoisomer thereof.

The present disclosure further provides methods of treating a disease or disorder associated with inhibition of PD-1/PD-L1 interaction, said method comprising administering to a patient in need thereof a therapeutically effective amount of a compound of disclosed herein, or a pharmaceutically acceptable salt or a stereoisomer thereof.

The present disclosure further provides methods of enhancing, stimulating and/or increasing the immune response in a patient, said method comprising administering to the patient in need thereof a therapeutically effective amount of a compound disclosed herein, or a pharmaceutically acceptable salt or a stereoisomer thereof.

DETAILED DESCRIPTION

I. Compounds

The present disclosure provides, inter alia, compounds of Formula I:

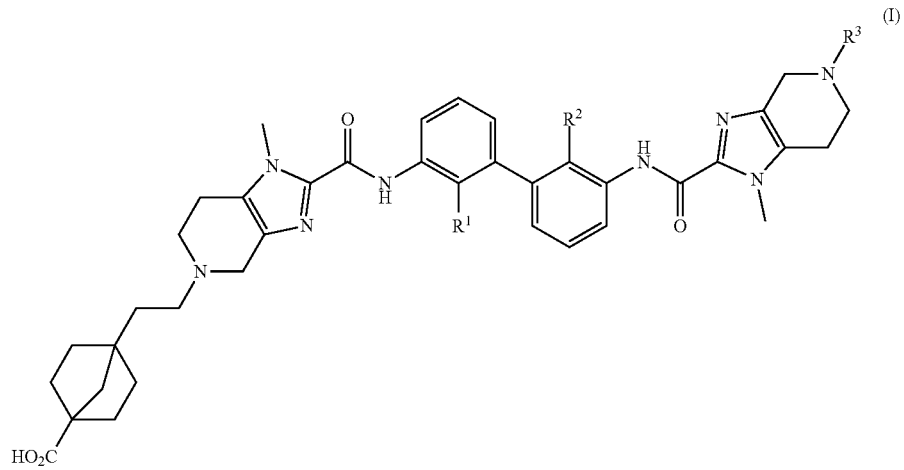

(I)

or a pharmaceutically acceptable salt or a stereoisomer thereof, wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl or 4- to 6-membered heterocycloalkyl-$C_{1-2}$ alkyl-, wherein the 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- of $R^3$ are each optionally substituted with 1 or 2 substituents independently selected from $CONH_2$, $SO_2NH_2$, COOH, OH, $CON(CH_3)_2$, $CH_3$, F, Cl, Br, CN, ethyl, and propyl.

In some embodiments, provided herein is a compound of Formula (I), or a pharmaceutically acceptable salt or a stereoisomer thereof, wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl or 4- to 6-membered heterocycloalkyl-$C_{1-2}$ alkyl-, wherein the 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- of $R^3$ are each optionally substituted with 1 or 2 substituents independently selected from $CONH_2$, $SO_2NH_2$, COOH, OH, $CON(CH_3)_2$, and $CH_3$.

In some embodiments, provided herein is a compound of Formula (I), or a pharmaceutically acceptable salt or a stereoisomer thereof, wherein:

$C_{1-2}$ alkyl- of $R^3$ are each optionally substituted with 1 or 2 substituents independently selected from $CONH_2$, $SO_2NH_2$, COOH, and OH.

In some embodiments, $R^1$ is methyl, F, Cl, or Br. In some embodiments, $R^1$ is methyl. In some embodiments, $R^1$ is F, Cl, or Br. In some embodiments, $R^1$ is Cl. In some embodiments, $R^1$ is methyl or Cl. In some embodiments, $R^1$ is CN. In some embodiments, $R^1$ is F. In some embodiments, $R^1$ is Br.

In some embodiments, $R^2$ is methyl. In some embodiments, $R^2$ is CN. In some embodiments, $R^2$ is F, Cl, or Br. In some embodiments, $R^2$ is Cl. In some embodiments, $R^2$ is methyl, CN, or Cl. In some embodiments, $R^2$ is F. In some embodiments, $R^2$ is Br.

In some embodiments, $R^1$ is Cl and $R^2$ is Cl.
In some embodiments, $R^1$ is Cl and $R^2$ is methyl.
In some embodiments, $R^1$ is methyl and $R^2$ is Cl.
In some embodiments, $R^1$ is Cl and $R^2$ is CN.
In some embodiments, $R^1$ is methyl and $R^2$ is methyl.

In some embodiments, $R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, OH, $CON(CH_3)_2$, $CH_3$, F, Cl, Br, CN, ethyl, and propyl.

In some embodiments, $R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, OH, $CON(CH_3)_2$, and $CH_3$.

In some embodiments, $R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, and OH.

In some embodiments, the 1 or 2 substituents on $R^3$ is independently selected from $CONH_2$, $SO_2NH_2$, COOH, OH, $CON(CH_3)_2$, and $CH_3$. In some embodiments, the substituent on $R^3$ is $CONH_2$. In some embodiments, the substituent on $R^3$ is $SO_2NH_2$. In some embodiments, the substituent on $R^3$ is COOH. In some embodiments, the substituent on $R^3$ is OH. In some embodiments, the substituent on $R^3$ is $CON(CH_3)_2$. In some embodiments, the substituent on $R^3$ is $CH_3$. In some embodiments, the substituent on $R^3$ is F. In some embodiments, the substituent on $R^3$ is Cl. In some embodiments, the substituent on $R^3$ is Br.

In some embodiments, the substituent on $R^3$ is CN. In some embodiments, the substituent on $R^3$ is ethyl. In some embodiments, the substituent on $R^3$ is propyl.

In some embodiments, $R^3$ is H.
In some embodiments, $R^3$ is $C_{1-4}$ alkyl, optionally substituted with 1 or 2 substituents independently selected from COOH, OH, and $CON(CH_3)_2$.

In some embodiments, $R^3$ is $C_{1-4}$ alkyl, optionally substituted with 1 or 2 substituents independently selected from COOH and OH.

In some embodiments, $R^3$ is methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, or 4-carboxybutyl.

In some embodiments, $R^3$ is methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl or 2-carboxy-2-methylpropyl.

In some embodiments, $R^3$ is $C_{3-8}$ cycloalkyl, optionally substituted with 1 or 2 substituents independently selected from COOH, OH, and $CH_3$.

In some embodiments, $R^3$ is $C_{3-8}$ cycloalkyl, optionally substituted with 1 or 2 substituents independently selected from COOH and OH.

In some embodiments, $R^3$ is $C_{3-8}$ cycloalkyl-$C_{1-2}$ alkyl-, optionally substituted with 1 or 2 substituents independently selected from COOH and OH.

In some embodiments, $R^3$ is $C_{6-10}$ aryl-$C_{1-2}$ alkyl, optionally substituted with 1 or 2 substituents independently selected from COOH and OH.

In some embodiments, $R^3$ is cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (4-carboxycyclohexyl)ethyl (e.g., (trans-4-carboxycyclohexyl)ethyl or (cis-4-carboxycyclohexyl)ethyl)), or 4-carboxy-4-methylcyclohexyl (e.g., cis-4-carboxy-4-methylcyclohexyl or trans-4-carboxy-4-methylcyclohexyl).

In some embodiments, $R^3$ is cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, or 4-carboxyphenethyl.

In some embodiments, $R^3$ is 5- to 6-membered heteroaryl-$C_{1-2}$ alkyl, optionally substituted with 1 or 2 substituents independently selected from $CONH_2$, $SO_2NH_2$, and COOH.

In some embodiments, $R^3$ is 4- to 6-membered heterocycloalkyl, optionally substituted with 1 or 2 substituents independently selected from $CONH_2$, $SO_2NH_2$, and COOH.

In some embodiments, $R^3$ is (1H-pyrazol-3-yl)methyl, tetrahydro-2H-pyran-4-yl, 1-carbamoylpiperidin-4-yl, 1-sulfamoylpiperidin-4-yl, or (3-carboxy-1H-pyrazol-5-yl)methyl.

In some embodiments, $R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, (3-carboxy-1H-pyrazol-5-yl)

methyl, 4-carboxybutyl, (4-carboxycyclohexyl)ethyl (e.g., (trans-4-carboxycyclohexyl)ethyl or (cis-4-carboxycyclohexyl)ethyl)), or 4-carboxy-4-methylcyclohexyl (e.g., cis-4-carboxy-4-methylcyclohexyl or trans-4-carboxy-4-methylcyclohexyl).

In some embodiments, $R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl) methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, or (3-carboxy-1H-pyrazol-5-yl) methyl.

In some embodiments, $R^3$ is methyl.
In some embodiments, $R^3$ is ethyl.
In some embodiments, $R^3$ is isopropyl.
In some embodiments, $R^3$ is 1,3-dihydroxypropan-2-yl.
In some embodiments, $R^3$ is 2,3-dihydroxypropyl.
In some embodiments, $R^3$ is 2-hydroxypropyl.
In some embodiments, $R^3$ is 2-hydroxyethyl.
In some embodiments, $R^3$ is 3-hydroxypropyl.
In some embodiments, $R^3$ is carboxymethyl.
In some embodiments, $R^3$ is 3-carboxypropyl.
In some embodiments, $R^3$ is 2-carboxy-2-methylpropyl.
In some embodiments, $R^3$ is cyclobutyl.
In some embodiments, $R^3$ is 4-hydroxycyclohexyl.
In some embodiments, $R^3$ is (1-carboxycyclopropyl)methyl.
In some embodiments, $R^3$ is (4-carboxybicyclo[2.2.1]heptan-1-yl)ethyl.
In some embodiments, $R^3$ is (4-carboxybicyclo[2.2.1]heptan-1-yl)methyl.
In some embodiments, $R^3$ is (4-carboxybicyclo[2.2.2]octan-1-yl)methyl.
In some embodiments, $R^3$ is (3-carboxybicyclo[1.1.1]pentan-1-yl)methyl.
In some embodiments, $R^3$ is 4-carboxyphenethyl.
In some embodiments, $R^3$ is (1H-pyrazol-3-yl)methyl.
In some embodiments, $R^3$ is tetrahydro-2H-pyran-4-yl.
In some embodiments, $R^3$ is 1-carbamoylpiperidin-4-yl.
In some embodiments, $R^3$ is 1-sulfamoylpiperidin-4-yl.
In some embodiments, $R^3$ is (3-carboxy-1H-pyrazol-5-yl) methyl.
In some embodiments, $R^3$ is 4-carboxybutyl.
In some embodiments, $R^3$ is (4-carboxycyclohexyl)ethyl (e.g., (trans-4-carboxycyclohexyl)ethyl or (cis-4-carboxycyclohexyl)ethyl)).
In some embodiments, $R^3$ is 4-carboxy-4-methylcyclohexyl (e.g., cis-4-carboxy-4-methylcyclohexyl or trans-4-carboxy-4-methylcyclohexyl).

In some embodiments, provided herein is a compound of Formula (I), or a pharmaceutically acceptable salt or a stereoisomer thereof, wherein wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, OH, $CON(CH_3)_2$, and $CH_3$.

In some embodiments, provided herein is a compound of Formula (I), or a pharmaceutically acceptable salt or a stereoisomer thereof, wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, and OH.

In some embodiments, provided herein is a compound of Formula (I), or a pharmaceutically acceptable salt or a stereoisomer thereof, wherein:
$R^1$ is methyl or Cl;
$R^2$ is methyl, CN, or Cl; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, OH, $CON(CH_3)_2$, and $CH_3$.

In some embodiments, provided herein is a compound of Formula (I), or a pharmaceutically acceptable salt or a stereoisomer thereof, wherein:
$R^1$ is methyl or Cl;
$R^2$ is methyl, CN, or Cl; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, and OH.

In some embodiments, provided herein is a compound of Formula (I), or a pharmaceutically acceptable salt or a stereoisomer thereof, wherein:
$R^1$ is methyl or Cl;
$R^2$ is methyl, CN, or Cl; and
$R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran- 4-yl, 1-carbamoylpiperidin-4-yl, 1-sulfamoylpiperidin-4-yl, (3-carboxy-1H-pyrazol-5-yl)methyl, 4-carboxybutyl, (4-carboxycyclohexyl)ethyl (e.g., (trans-4-carboxycyclohexyl)ethyl or (cis-4-carboxycyclohexyl)ethyl)), or 4-carboxy-4-methylcyclohexyl (e.g., cis-4-carboxy-4-methylcyclohexyl or trans-4-carboxy-4-methylcyclohexyl).

In some embodiments, provided herein is a compound of Formula (I), or a pharmaceutically acceptable salt or a stereoisomer thereof, wherein:

$R^1$ is methyl or Cl;

$R^2$ is methyl, CN, or Cl; and $R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, or (3-carboxy-1H-pyrazol-5-yl)methyl.

In some embodiments, provided herein is a compound is selected from:

4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-isopropyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-cyclobutyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(1-carbamoylpiperidin-4-yl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(1-methyl-5-(1-sulfamoylpiperidin-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-((1H-pyrazol-3-yl)methyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-(1,3-dihydroxypropan-2-yl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-(2,3-dihydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3-1-(2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3-1-(2-hydroxyethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-(3-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid);

4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid; 4-(2-(2-((3'-(5-(carboxymethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(2-carboxy-2-methylpropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-((1-carboxycyclopropyl)methyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)bicyclo[2.2.2]octane-1-carboxylic acid;

3-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]
pyridin-5-yl)methyl)bicyclo[1.1.1]pentane-1-carboxylic
acid;

4-(2-(2-((3'-(5-(4-carboxyphenethyl)-1-methyl-4,5,6,7-
tetrahydro-1H-imidazo[4,5-c]pyridine-2-carboxamido)-2,
2'-dichloro-[1,1'-biphenyl]-3-yl)carbamoyl)-1-methyl-1,4,6,
7-tetrahydro-5H-imidazo[4,5-c]pyri din-5-yl)ethyl)bicyclo
[2.2.1]heptane-1-carboxylic acid;

5-((2-((3'-(5-(2-(4-carboxybicyclo[2.2.1]heptan-1-yl)
ethyl)-1-methyl-4,5,6,7-tetrahydro-1H-imidazo[4,5-c]pyri-
dine-2-carboxamido)-2,2'-dichloro-[1,1'-biphenyl]-3-yl)car-
bamoyl)-1-methyl-1,4,6,7-tetrahydro-5H-imidazo[4,5-c]
pyridin-5-yl)methyl)-1H-pyrazole-3-carboxylic acid;

4-(2-(2-((2-chloro-2'-methyl-3'-(1-methyl-4,5,6,7-tetra-
hydro-1H-imidazo[4,5-c]pyridine-2-carboxamido)-[1,1'-bi-
phenyl]-3-yl)carbamoyl)-1-methyl-1,4,6,7-tetrahydro-5H-
imidazo[4,5-c]pyridin-5-yl)ethyl)bicyclo[2.2.1]heptane-1-
carboxylic acid;

4-(2-(2-((2-chloro-2'-methyl-3'-(1-methyl-5-(tetrahydro-
2H-pyran-4-yl)-4,5,6,7-tetrahydro-1H-imidazo[4,5-c]pyri-
dine-2-carboxamido)-[1,1'-biphenyl]-3-yl)carbamoyl)-1-
methyl-1,4,6,7-tetrahydro-5H-imidazo[4,5-c]pyridin-5-yl)
ethyl)bicyclo[2.2.1]heptane-1-carboxylic acid;

4-(2-(2-((2-chloro-3'-(1,5-dimethyl-4,5,6,7-tetrahydro-
1H-imidazo[4,5-c]pyridine-2-carboxamido)-2'-methyl-[1,
1'-biphenyl]-3-yl)carbamoyl)-1-methyl-1,4,6,7-tetrahydro-
5H-imidazo[4,5-c]pyridin-5-yl)ethyl)bicyclo[2.2.1]
heptane-1-carboxylic acid;

4-(2-(2-((3'-(5-(1-carbamoylpiperidin-4-yl)-1-methyl-4,
5,6,7-tetrahydro-1H-imidazo[4,5-c]pyridine-2-carbox-
amido)-2-chloro-2'-methyl-[1,1'-biphenyl]-3-yl)carbam-
oyl)-1-methyl-1,4,6,7-tetrahydro-5H-imidazo[4,5-c]
pyridin-5-yl)ethyl)bicyclo[2.2.1]heptane-1-carboxylic acid;

4-(2-(2-((2-chloro-3'-(5-(2-hydroxypropyl)-1-methyl-4,5,
6,7-tetrahydro-1H-imidazo[4,5-c]pyridine-2-carboxamido)-
2'-methyl-[1,1'-biphenyl]-3-yl)carbamoyl)-1-methyl-1,4,6,
7-tetrahydro-5H-imidazo[4,5-c]pyridin-5-yl)ethyl)bicyclo
[2.2.1]heptane-1-carboxylic acid;

4-(2-(2-((2-chloro-3'-(5-(2-hydroxyethyl)-1-methyl-4,5,
6,7-tetrahydro-1H-imidazo[4,5-c]pyridine-2-carboxamido)-
2'-methyl-[1,1'-biphenyl]-3-yl)carbamoyl)-1-methyl-1,4,6,
7-tetrahydro-5H-imidazo[4,5-c]pyridin-5-yl)ethyl)bicyclo
[2.2.1]heptane-1-carboxylic acid;

4,4'-(((((2-chloro-2'-methyl-[1,1'-biphenyl]-3,3'-diyl)bis
(azanediyl))bis(carbonyl))bis(1-methyl-1,4,6,7-tetrahydro-
5H-imidazo[4,5-c]pyridine-2,5-diyl))bis(ethane-2,1-diyl))
bis(bicyclo[2.2.1]heptane-1-carboxylic acid);

4-((2-((3'-(5-(2-(4-carboxybicyclo[2.2.1]heptan-1-yl)
ethyl)-1-methyl-4,5,6,7-tetrahydro-1H-imidazo[4,5-c]pyri-
dine-2-carboxamido)-2'-chloro-2-methyl-[1,1'-biphenyl]-3-
yl)carbamoyl)-1-methyl-1,4,6,7-tetrahydro-5H-imidazo[4,
5-c]pyridin-5-yl)methyl)bicyclo[2.2.1]heptane-1-carboxylic
acid;

4-(2-(2-((3'-(5-(4-carboxyphenethyl)-1-methyl-4,5,6,7-
tetrahydro-1H-imidazo[4,5-c]pyridine-2-carboxamido)-2-
chloro-2'-methyl-[1,1'-biphenyl]-3-yl)carbamoyl)-1-methyl-
1,4,6,7-tetrahydro-5H-imidazo[4,5-c]pyridin-5-yl)ethyl)
bicyclo[2.2.1]heptane-1-carboxylic acid;

4-(2-(2-((2-42'-chloro-2-methyl-3'-(1-methyl-4,5,6,7-tetra-
hydro-1H-imidazo[4,5-c]pyridine-2-carboxamido)-[1,1'-bi-
phenyl]-3-yl)carbamoyl)-1-methyl-1,4,6,7-tetrahydro-5H-
imidazo[4,5-c]pyridin-5-yl)ethyl)bicyclo[2.2.1]heptane-1-
carboxylic acid;

4-(2-(2-((2'-chloro-2-methyl-3'-(1-methyl-5-(tetrahydro-
2H-pyran-4-yl)-4,5,6,7-tetrahydro-1H-imidazo[4,5-c]pyri-
dine-2-carboxamido)-[1,1'-biphenyl]-3-yl)carbamoyl)-1-
methyl-1,4,6,7-tetrahydro-5H-imidazo[4,5-c]pyridin-5-yl)
ethyl)bicyclo[2.2.1]heptane-1-carboxylic acid;

4-(2-(2-((2'-chloro-3'-(1,5-dimethyl-4,5,6,7-tetrahydro-
1H-imidazo[4,5-c]pyridine-2-carboxamido)-2-methyl-[1,1'-
biphenyl]-3-yl)carbamoyl)-1-methyl-1,4,6,7-tetrahydro-
5H-imidazo[4,5-c]pyridin-5-yl)ethyl)bicyclo[2.2.1]
heptane-1-carboxylic acid;

4-(2-(2-((3'-(5-(1-carbamoylpiperidin-4-yl)-1-methyl-4,
5,6,7-tetrahydro-1H-imidazo[4,5-c]pyridine-2-carbox-
amido)-2'-chloro-2-methyl-[1,1'-biphenyl]-3-yl)carbam-
oyl)-1-methyl-1,4,6,7-tetrahydro-5H-imidazo[4,5-c]
pyridin-5-yl)ethyl)bicyclo[2.2.1]heptane-1-carboxylic acid;

4-(2-(2-42'-chloro-3'-(5-(2-hydroxypropyl)-1-methyl-4,5,
6,7-tetrahydro-1H-imidazo[4,5-c]pyridine-2-carboxamido)-
2-methyl-[1,1'-biphenyl]-3-yl)carbamoyl)-1-methyl-1,4,6,
7-tetrahydro-5H-imidazo[4,5-c]pyridin-5-yl)ethyl)bicyclo
[2.2.1]heptane-1-carboxylic acid;

4-(2-(2-42'-chloro-3'-(5-(2-hydroxyethyl)-1-methyl-4,5,
6,7-tetrahydro-1H-imidazo[4,5-c]pyridine-2-carboxamido)-
2-methyl-[1,1'-biphenyl]-3-yl)carbamoyl)-1-methyl-1,4,6,
7-tetrahydro-5H-imidazo[4,5-c]pyridin-5-yl)ethyl)bicyclo
[2.2.1]heptane-1-carboxylic acid;

4-((2-((3'-(5-(2-(4-carboxybicyclo[2.2.1]heptan-1-yl)
ethyl)-1-methyl-4,5,6,7-tetrahydro-1H-imidazo[4,5-c]pyri-
dine-2-carboxamido)-2-chloro-2'-methyl-[1,1'-biphenyl]-3-
yl)carbamoyl)-1-methyl-1,4,6,7-tetrahydro-5H-imidazo[4,
5-c]pyridin-5-yl)methyl)bicyclo[2.2.1]heptane-1-carboxylic
acid;

4-(2-(2-((3'-(5-(4-carboxyphenethyl)-1-methyl-4,5,6,7-
tetrahydro-1H-imidazo[4,5-c]pyridine-2-carboxamido)-2'-
chloro-2-methyl-[1,1'-biphenyl]-3-yl)carbamoyl)-1-methyl-
1,4,6,7-tetrahydro-5H-imidazo[4,5-c]pyridin-5-yl)ethyl)
bicyclo[2.2.1]heptane-1-carboxylic acid;

4-(2-(2-((2-chloro-2'-cyano-3'-(1-methyl-4,5,6,7-tetra-
hydro-1H-imidazo[4,5-c]pyridine-2-carboxamido)-[1,1'-bi-
phenyl]-3-yl)carbamoyl)-1-methyl-1,4,6,7-tetrahydro-5H-
imidazo[4,5-c]pyridin-5-yl)ethyl)bicyclo[2.2.1]heptane-1-
carboxylic acid;

4-(2-(2-((2-chloro-2'-cyano-3'-(1-methyl-5-(tetrahydro-
2H-pyran-4-yl)-4,5,6,7-tetrahydro-1H-imidazo[4,5-c]pyri-
dine-2-carboxamido)-[1,1'-biphenyl]-3-yl)carbamoyl)-1-
methyl-1,4,6,7-tetrahydro-5H-imidazo[4,5-c]pyridin-5-yl)
ethyl)bicyclo[2.2.1]heptane-1-carboxylic acid;

4-(2-(2-((2-chloro-2'-cyano-3'-(1,5-dimethyl-4,5,6,7-tet-
rahydro-1H-imidazo[4,5-c]pyridine-2-carboxamido)-[1,1'-
biphenyl]-3-yl)carbamoyl)-1-methyl-1,4,6,7-tetrahydro-
5H-imidazo[4,5-c]pyridin-5-yl)ethyl)bicyclo[2.2.1]
heptane-1-carboxylic acid;

4-(2-(2-((2-chloro-2'-cyano-3'-(5-(2-hydroxypropyl)-1-
methyl-4,5,6,7-tetrahydro-1H-imidazo[4,5-c]pyridine-2-
carboxamido)[1,1'-biphenyl]-3-yl)carbamoyl)-1-methyl-1,
4,6,7-tetrahydro-5H-imidazo[4,5-c]pyri din-5-yl)ethyl)
bicyclo[2.2.1]heptane-1-carboxylic acid;

4-(2-(2-((2-chloro-2'-cyano-3'-(5-(2-hydroxyethyl)-1-
methyl-4,5,6,7-tetrahydro-1H-imidazo[4,5-c]pyridine-2-
carboxamido)[1,1'-biphenyl]-3-yl)carbamoyl)-1-methyl-1,
4,6,7-tetrahydro-5H-imidazo[4,5-c]pyri din-5-yl)ethyl)
bicyclo[2.2.1]heptane-1-carboxylic acid;

4,4'-(((((2-chloro-2'-cyano-[1,1'-biphenyl]-3,3'-diyl)bis
(azanediyl))bis(carbonyl))bis(1-methyl-1,4,6,7-tetrahydro-
5H-imidazo[4,5-c]pyridine-2,5-diyl))bis(ethane-2,1-diyl))
bis(bicyclo[2.2.1]heptane-1-carboxylic acid);

4-((2-((3'-(5-(2-(4-carboxybicyclo[2.2.1]heptan-1-yl)
ethyl)-1-methyl-4,5,6,7-tetrahydro-1H-imidazo[4,5-c]pyri-
dine-2-carboxamido)-2'-chloro-2-cyano-[1,1'-biphenyl]-3- yl)carbamoyl)-1-methyl-1,4,6,7-tetrahydro-5H-imidazo[4,5-c]pyridin-5-yl)methyl)bicyclo[2.2.1]heptane-1-carboxylic acid;

4-(2-(2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4,4'-(((((2,2'-dimethyl-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid);

4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid;

4-(2-(2-((2,2'-dimethyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(2-hydroxypropyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(2-hydroxyethyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid; and 4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

or a pharmaceutically acceptable salt or a stereoisomer thereof.

In some embodiments, provided herein is a compound selected from:

4-(2-(2-((3'-(5-(2-(4-carboxycyclohexyl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(4-carboxybutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((2,2'-dichloro-3'-(5-(5-(dimethyl amino)-5-oxopentyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

4-(2-(2-((3'-(5-(4-carboxy-4-methylcyclohexyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid;

or a pharmaceutically acceptable salt or a stereoisomer thereof.

In some embodiments, provided herein is a compound of Formula I, wherein one or more hydrogen atoms are replaced by deuterium, or a pharmaceutically acceptable salt or a stereoisomer thereof.

In some embodiments, the compound is selected from the examples provided herein.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and 13 (CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound.

The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —$NH_2$.

The term "carbamyl" refers to a group of formula C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F. In some embodiments, halo groups are Cl.

The term "haloalkyl" as used herein refers to an alkyl group in which one or more of the hydrogen atoms has been replaced by a halogen atom. The term "$C_{n-m}$haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, indanyl, indenyl and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroatom" used herein is meant to include boron, phosphorus, sulfur, oxygen and nitrogen.

The term "heteroaryl" or "heteroaromatic," employed alone or in combination with other terms, refers to a monocyclic or polycyclic aromatic heterocycle having at least one heteroatom ring member selected from boron, phosphorus, sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-14, or 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eightmembered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-b]thiazolyl, purinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, bicyclo[2.2.1]heptanyl, bicyclo[2.2.2]octanyl and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from boron, nitrogen, sulfur, oxygen and phosphorus, and which has 4-14 ring members, 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic or polycyclic (e.g., having two or three fused or bridged rings) ring systems or spirocycles. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art.

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

II. Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

Compounds of formula 1-8 can be synthesized using a process shown in Scheme 1. Boc-protected compound 1-1 can be deprotected under acidic conditions (e.g., hydrochloric acid or trifluoroacetic acid) to provide amine 1-2. Palladium-catalyzed cross-coupling reaction of halo-substituted compound 1-2 with a boronic ester of formula 1-3 under standard conditions (such as Suzuki coupling reaction, e.g., in the presence of a palladium catalyst and a suitable base) can produce compounds of formula 1-4. The reaction of amine 1-4 with methyl 4-(2-oxoethyl)bicyclo[2.2.1]heptane-1-carboxylate 1-5 under reductive amination conditions (e.g., sodium triacetoxyborohydride or sodium cyanoborohydride as the reducing reagent) to generate compounds of formula 1-6. After removal of the Boc group of compound 1-6 under acidic conditions (e.g., hydrochloric acid or trifluoroacetic acid), the $R^3$ group can be introduced to the resulting amine by reductive amination with the corresponding aldehydes or ketones to generate compounds of formula 1-7. Then ester 1-7 can be hydrolyzed under alkaline conditions to provide the desired compounds of formula 1-8.

Scheme 1

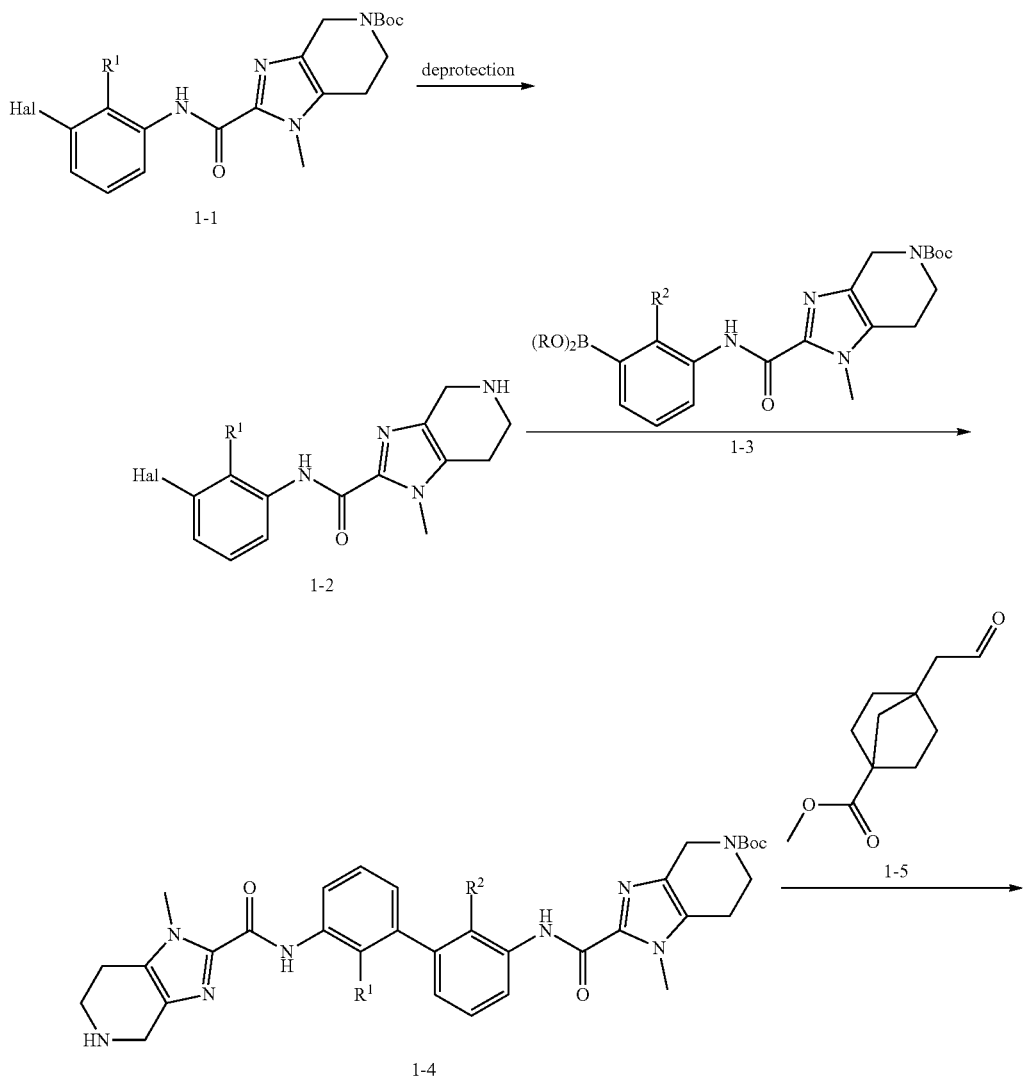

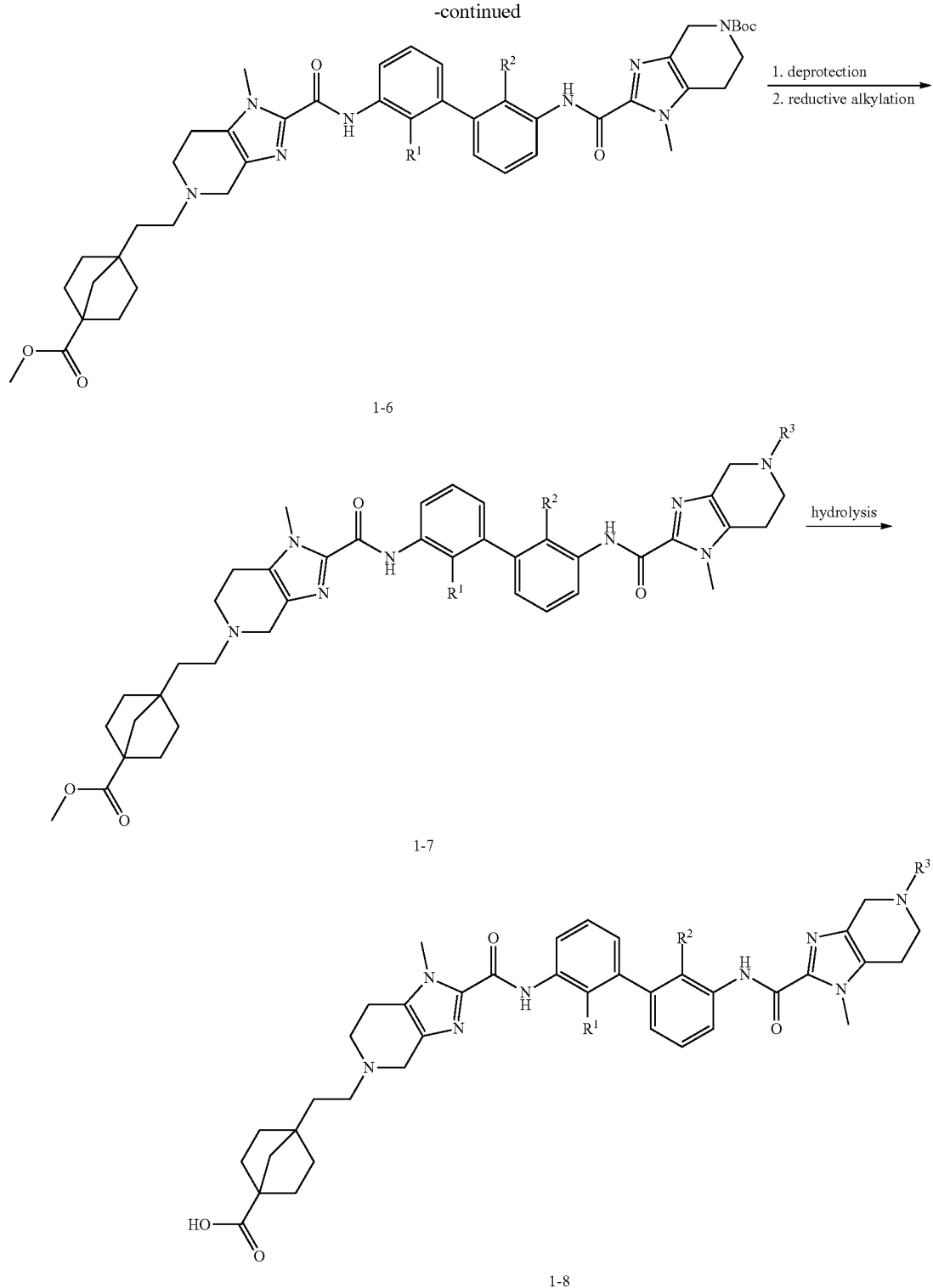

Compounds of formula 2-4 can be synthesized using a process shown in Scheme 2. The free amine in compound 2-1 can be protected with Boc. The resulting compound can be deprotonated by a strong base such as, but not limited to, n-butyl lithium to generate the corresponding heteroaryl lithium intermediate, which can further react with an alkyl- chloroformate to give esters of formula 2-2. The reaction of ester 2-2 with halo-substituted aniline 2-3 in the presence of a suitable base such as, but not limited to, potassium tert-butoxide can furnish the desired compounds of formula 2-4.

Scheme 2

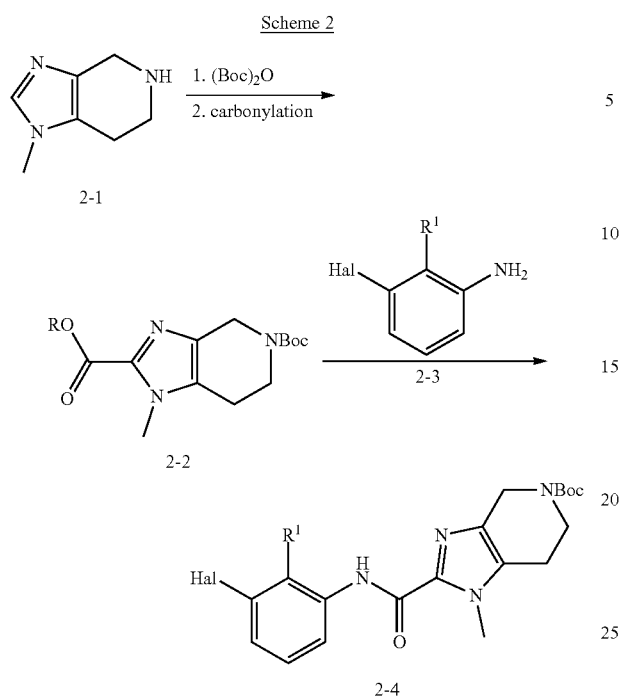

Compounds of formula 3-2 can be prepared according to Scheme 3. Halo-substituted compound 3-1 can be converted to the boronic ester 3-2 under standard conditions [e.g., in the presence of bis(pinacolato)diboron and a palladium catalyst, such as, tetrakis(triphenylphosphine) palladium(0) and palladium(II) acetate].

Scheme 3

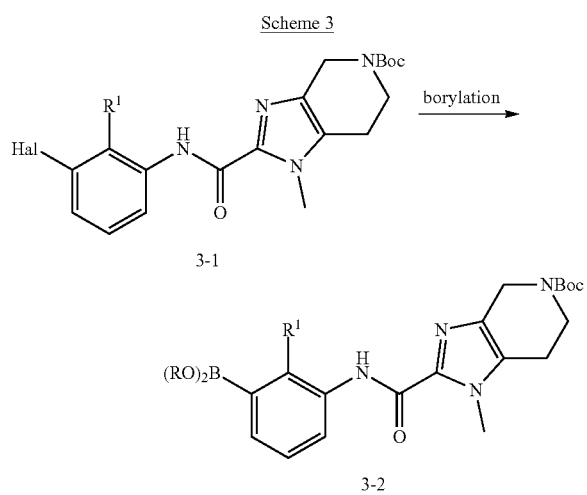

Compound 4-4 can be prepared according to Scheme 4. Alcohol 4-1 can be converted to aldehyde 4-2 in the presence of an oxidant such as, but not limited to, Dess-Martin periodinane or pyridinium chlorochromate. Aldehyde 4-2 can be extended by one carbon atom in a Wittig reaction with (methoxymethyl)triphenylphosphonium chloride 4-3 to form an enol ether, which can be further hydrolyzed under acidic conditions (e.g., hydrochloric acid) to provide the desired compound 4-4.

Scheme 4

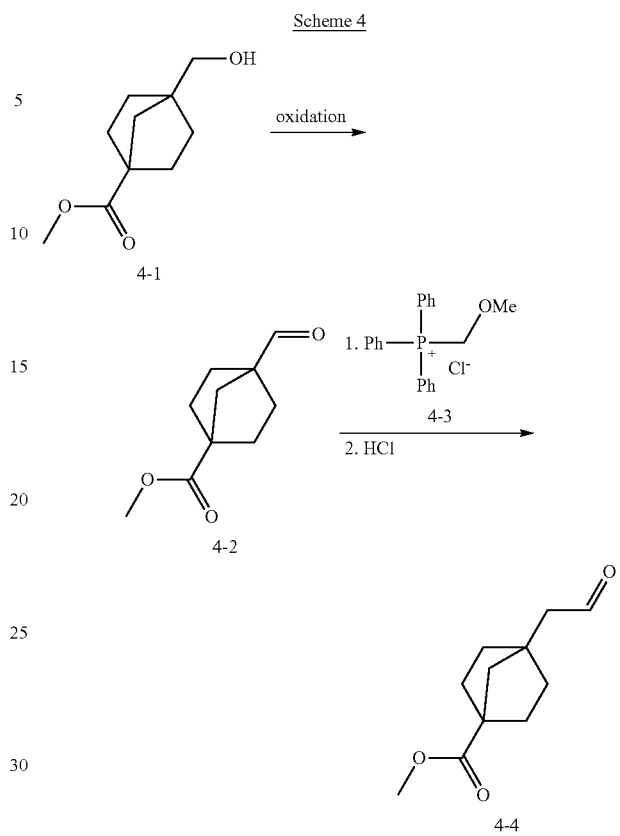

III. Uses of the Compounds

Compounds of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the compounds of the present disclosure, or pharmaceutically acceptable salts or stereoisomers thereof, are useful for therapeutic administration to enhance, stimulate and/or increase immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a compound of Formula (I) or of any of the formulas as described herein, or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound of Formula (I) or any of the formulas as described herein, a compound or composition as recited in any of the claims and described herein, or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-L1.

In some embodiments, cancers treatable with compounds of the present disclosure include melanoma (e.g., metastatic malignant melanoma, cutaneous melanoma), renal cancer (e.g. clear cell carcinoma), prostate cancer (e.g. hormone refractory prostate adenocarcinoma), breast cancer (e.g., breast invasive carcinoma), colon cancer, lung cancer (e.g. non-small cell lung cancer and small cell lung cancer), squamous cell head and neck cancer (e.g., squamous cell carcinoma of the head and neck), urothelial cancer (e.g., bladder cancer, nonmuscle invasive bladder cancer (NMIBC)) and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, biliary tract cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC) (e.g., squamous cell NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (carcinoma, squamous cell carcinoma, adenocarcinoma, leiomyosarcoma, lymphoma), stomach (carcinoma, lymphoma, leiomyosarcoma, adenocarcinoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer (e.g., colorectal adenocarcinoma).

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In some embodiments, the cancer is a urological cancer (e.g., papillary kidney carcinoma, testicular germ cell cancer, chromophobe renal cell carcinoma, clear cell renal carcinoma, or prostate adenocarcinoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, serous adenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma (e.g., cutaneous squamous cell carcinoma), Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include *chlamydia*, rickettsial bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida (albicans, krusei, glabrata, tropicalis*, etc.), *Cryptococcus neoformans, Aspergillus (fumigatus, niger*, etc.), Genus *Mucorales (mucor, absidia*, rhizophus), *Sporothrix schenkii, Blastomyces dermatitidis, Paracoccidioides brasiliensis, Coccidioides immitis* and *Histoplasma capsulatum.*

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

The present disclosure provides a method for treating neurodegenerative diseases or disorders. The method includes administering to a patient in need thereof, a therapeutically effective amount of a compound of Formula (I) or any of the formulas as described herein, a compound as recited in any of the claims and described herein, or a salt thereof. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD122, CD96, CD73, CD47, CSF1R, JAK, PI3K delta, PI3K gamma, TAM, arginase, HPK1, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137 (4-1BB). In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from MR inhibitors, TIGIT inhibitors, LAIR1 inhibitors, CD160 inhibitors, 2B4 inhibitors and TGF beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, cemiplimab, spartalizumab, camrelizumab, cetrelimab, toripalimab, sintilimab, SHR-1210, PDR001, MGA012, PDR001, AB122, AMP-224, JTX-4014, BGB-108, BCD-100, BAT1306, LZMO09, AK105, HLX10, or TSR-042. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent (s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), durvalumab (Imfinzi®), atezolizumab (Tecentriq®), Avelumab (Bavencio®), MSB0010718C, tislelizumab, FAZ053, KN035, CS1001, SHR-1316, CBT-502, A167, STI-A101, CK-301, BGB-A333, MSB-2311, HLX20, or LY3300054. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 bispecific antibody is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of PD-1 and CTLA-4, e.g., an anti-PD-1/CTLA-4 bispecific antibody. In some embodiments, the anti-PD-1/CTLA-4 antibody is AK104.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab. In some embodiments, the inhibitor of CD73 is MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the agonist of an immune checkpoint molecule is an agonist of GITR, e.g., an anti-GITR antibody. In some embodiments, the agonist is TRX518, MK-4166, INCAGN1876, MK-1248, AMG228, BMS-986156, GWN323, MEDI1873, or MEDI6469.

In some embodiments, the agonist of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, BMS-986178, or 9B12. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by dysfunction in multiple biological pathways. Thus, it may be useful to combine inhibitors of different mechanisms, such as enzyme inhibitors, signal transduction inhibitors, inhibitors of chromatin dynamics or modulators of immune responses, to treat such conditions. Targeting more than one signaling pathway (or more than one biological molecule involved in a given signaling pathway) may reduce the likelihood of drug-resistance arising in a cell population, or reduce the toxicity of treatment.

The compounds of the present disclosure can be used in combination with one or more other therapies for the treatment of diseases, such as cancer or infections. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCY54828), INCB62079), an EGFR (also known as ErB-1 or HER-1) inhibitor (e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxolitinib, baricitinib or itacitinib (INCB39110)), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., Parsaclisib (INCB50465) and INCB50797), a PI3K-gamma inhibitor such as PI3K-gamma selective inhibitor, a Pim inhibitor (e.g., INCB53914), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib, talazoparib, or niraparib), a CSF1R inhibitor, a TAM receptor tyrosine kinase (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHPT/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), an arginase inhibitor (INCB001158), a PARP inhibitor (such as rucaparib or olaparib), sitravatinib, a B-Raf inhibitor-MEK inhibitor combination (such as encorafenib plus binimetinib, dabrafenib plus trametinib, or cobimetinib plus vemurafenib), and an adenosine receptor antagonist or combinations thereof.

In some embodiments, the compounds of the present disclosure can be combined with a TLR7 agonist (e.g., imiquimod).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, STING agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab), 4-1BB (e.g. urelumab, utomilumab), antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to nivolumab, pembrolizumab, atezolizumab, durvalumab, avelumab and SHR-1210.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, coronavirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia, rickettsial* bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida (albicans, krusei, glabrata, tropicalis,* etc.), *Cryptococcus neoformans, Aspergillus (fumigatus, niger,* etc.), Genus *Mucorales (mucor, absidia,* rhizophus), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli,* Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

When more than one pharmaceutical agent is administered to a patient, they can be administered simultaneously, separately, sequentially, or in combination (e.g., for more than two agents).

IV. Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the present disclosure can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled compounds.

The present invention further includes isotopically-labeled compounds of the disclosure. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro PD-L1 protein labeling and competition assays, compounds that incorporate $^3H$, $^{14}C$, $^{82}Br$, $^{125}I$, $^{124}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a PD-L1 protein by monitoring its concentration variation when contacting with the PD-L1 protein, through tracking of the labeling. For example, a test compound (labeled) can be evaluated for its ability to reduce binding of another compound which is known to bind to a PD-L1 protein (i.e., standard compound). Accordingly, the ability of a test compound to compete with the standard compound for binding to the PD-L1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following abbreviations may be used herein: aq. (aqueous); br (broad); d (doublet); dd (doublet of doublets); DCM (dichloromethane); DMF (N, N-dimethylformamide); Et (ethyl); EtOAc (ethyl acetate); g (gram(s)); h (hour(s)); HPLC (high performance liquid chromatography); Hz (hertz); J (coupling constant); LCMS (liquid chromatography—mass spectrometry); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); nM (nanomolar); NMR (nuclear magnetic resonance spectroscopy); Ph (phenyl); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent).

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of PD-1/PD-L1 protein/protein interaction according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J. Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

Example 1

4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

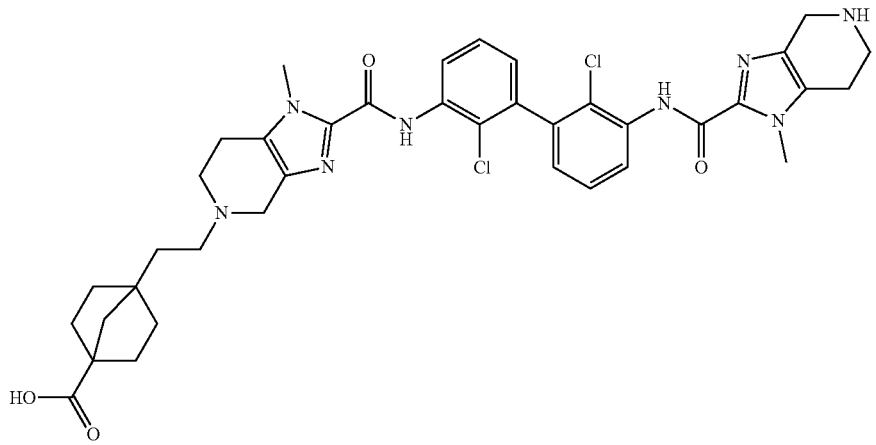

Step 1: tert-butyl 1-methyl-1,4,6,7-tetrahydro-5H-imidazo[4,5-c]pyridine-5-carboxylate

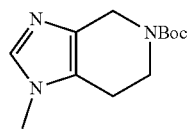 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat #SY032476: 2.0 g, 14.58 mmol) and (Boc)$_2$O (3.38 mL, 14.58 mmol) in dichloromethane (60 mL) was stirred at room temperature for 1 h. The reaction was quenched with saturated aqueous NaHCO$_3$ solution, and extracted with ethyl acetate. The combined organic layers were washed with brine, dried over Na$_2$SO$_4$, filtered, and concentrated under reduced pressure. The crude product was used directly in the next step without further purification. LC-MS calculated for C$_{12}$H$_{20}$N$_3$O$_2$ (M+H)$^+$: m/z=238.2; found 238.2.

Step 2: 5-tert-butyl 2-methyl 1-methyl-6,7-dihydro-1H-imidazo[4,5-c]pyridine-2,5(4H)-dicarboxylate

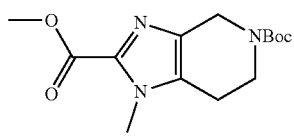 [SMILES: COC(=O)c1nc2c(n1C)CCN(C(=O)OC(C)(C)C)C2]

n-Butyllithium in hexanes (2.5 M, 7.00 mL, 17.49 mmol) was added to a cold (−78° C.) solution of tert-butyl 1-methyl-1,4,6,7-tetrahydro-5H-imidazo[4,5-c]pyridine-5-carboxylate (Step 1: 3.46 g, 14.58 mmol) in tetrahydrofuran (60.0 mL). The reaction mixture was stirred at −78° C. for 10 min prior to the addition of methyl chloroformate (1.69 mL, 21.87 mmol). After being stirred at −78° C. for 30 min, the reaction was then quenched with saturated aqueous NaHCO$_3$ solution, and extracted with ethyl acetate. The combined organic layers were washed with brine, dried over Na$_2$SO$_4$, filtered, and concentrated under reduced pressure. The residue was purified by flash chromatography on a silica gel column eluting with 0-80% ethyl acetate in hexanes to afford the desired product. LC-MS calculated for C$_{14}$H$_{22}$N$_3$O$_4$ (M+H)$^+$: m/z=296.2; found 296.3.

Step 3: tert-butyl 2-((3-bromo-2-chlorophenyl)carbamoyl)-1-methyl-1,4,6,7-tetrahydro-5H-imidazo[4,5-c]pyridine-5-carboxylate

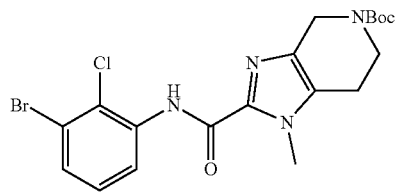 [SMILES: Cn1c(C(=O)Nc2cccc(Br)c2Cl)nc2c1CCN(C(=O)OC(C)(C)C)C2]

Potassium tert-butoxide in THF (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (Step 2: 500 mg, 1.69 mmol) and 3-bromo-2-chloroaniline (350 mg, 1.69 mmol) in tetrahydrofuran (12.0 mL). After being stirred at room temperature for 30 min, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 0-50% ethyl acetate in hexanes to afford the desired product. LC-MS calculated for C$_{19}$H$_{23}$BrClN$_4$O$_3$ (M+H)$^+$: m/z=469.1/471.1; found 469.1/471.1.

Step 4: tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate

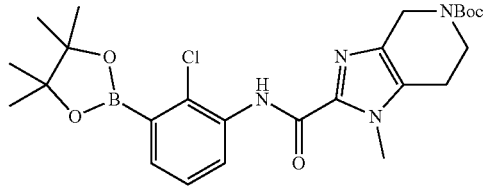 [SMILES: Cn1c(C(=O)Nc2cccc(B3OC(C)(C)C(C)(C)O3)c2Cl)nc2c1CCN(C(=O)OC(C)(C)C)C2]

A mixture of tert-butyl 2-((3-bromo-2-chlorophenyl)carbamoyl)-1-methyl-1,4,6,7-tetrahydro-5H-imidazo[4,5-c]pyridine-5-carboxylate (Step 3: 1.0 g, 2.129 mmol), 4,4,5,5,4',4',5',5'-octamethyl-[2,2']bi[[1,3,2]dioxaborolanyl] (0.649 g, 2.55 mmol), [1,1'-bis(diphenylphosphino)ferrocene]dichloropalladium(II) complexed with dichloromethane (1:1) (0.174 g, 0.213 mmol) and potassium acetate (0.522 g, 5.32 mmol) in 1,4-dioxane (24.0 mL) was purged with nitrogen and then stirred at 110° C. for 3 h. The reaction mixture was cooled to room temperature, diluted with dichloromethane, and then filtered through Celite. The filtrate was concentrated under reduced pressure, and the residue was purified by flash chromatography on a silica gel column eluting with 0-30% ethyl acetate in hexanes to afford the desired product. LC-MS calculated for $C_{25}H_{35}BClN_4O_5$ (M+H)$^+$: m/z=517.2; found 517.2.

Step 5: tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

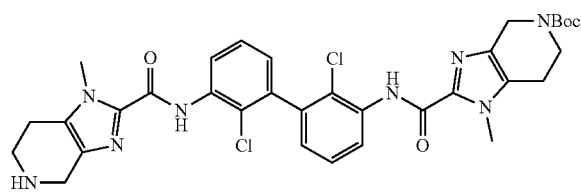

A mixture of tert-butyl 2-((3-bromo-2-chlorophenyl)carbamoyl)-1-methyl-1,4,6,7-tetrahydro-5H-imidazo[4,5-c]pyridine-5-carboxylate (Step 3: 900 mg, 1.92 mmol) in trifluoroacetic acid (4.0 mL) and dichloromethane (8.0 mL) was stirred at room temperature for 1 h. The reaction mixture was concentrated under reduced pressure. A mixture of the above residue, tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Step 4: 1188 mg, 2.30 mmol), sodium carbonate (1015 mg, 9.58 mmol) and [1,1-bis(di-cyclohexylphosphino)ferrocene]dichloropallaclium(II) (145 mg, 0.19 mmol) in 1,4-dioxane (12.0 mL) and water (6.0 mL) was purged with nitrogen and then stirred at 110° C. for 2 h. After being cooled to room temperature, the reaction mixture was diluted with water and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for $C_{33}H_{37}Cl_2N_8O_4$ (M+H)$^+$: m/z=679.2; found 679.2.

Step 6: methyl 4-formylbicyclo[2.2.1]heptane-1-carboxylate

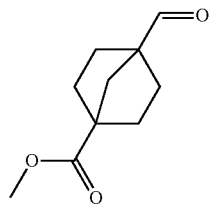

A mixture of methyl 4-(hydroxymethyl)bicyclo[2.2.1]heptane-1-carboxylate (PharmaBlock, cat #PBZ3820: 400 mg, 2.17 mmol) and Dess-Martin periodinane (1381 mg, 3.26 mmol) in dichloromethane (12.0 mL) was stirred at room temperature for 2 h. The reaction mixture was quenched with 20% aqueous Na$_2$S$_2$O$_3$ solution and saturated aqueous NaHCO$_3$ solution, and extracted with ethyl acetate. The combined organic layers were washed with brine, dried over Na$_2$SO$_4$, filtered, and concentrated under reduced pressure. The crude product was used directly in the next step without further purification.

Step 7: methyl 4-(2-oxoethyl)bicyclo[2.2.1]heptane-1-carboxylate

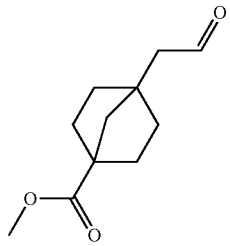

Potassium tert-butoxide in THF (1.0 M, 4.39 mL, 4.39 mmol) was added to a suspension of chloro(methoxymethyl)triphenylphosphorane (1505 mg, 4.39 mmol) in tetrahydrofuran (12.0 mL). The reaction mixture was stirred at room temperature for 1 h prior to the addition of methyl 4-formylbicyclo[2.2.1]heptane-1-carboxylate (Step 6: 400 mg, 2.195 mmol). After being stirred at room temperature for 5 h, the reaction mixture was quenched with water, and extracted with ethyl acetate. The combined organic layers were washed with brine, dried over Na$_2$SO$_4$, filtered, and concentrated under reduced pressure. The residue was dissolved in tetrahydrofuran (12.0 mL), and then treated with HCl in water (4.0 M, 11 mL, 43.9 mmol) at room temperature for 1 h. The reaction mixture was diluted with water and extracted with ethyl acetate. The combined organic layers were washed with brine, dried over Na$_2$SO$_4$, filtered, and concentrated under reduced pressure. The crude product was used directly in the next step without further purification.

Step 8: methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

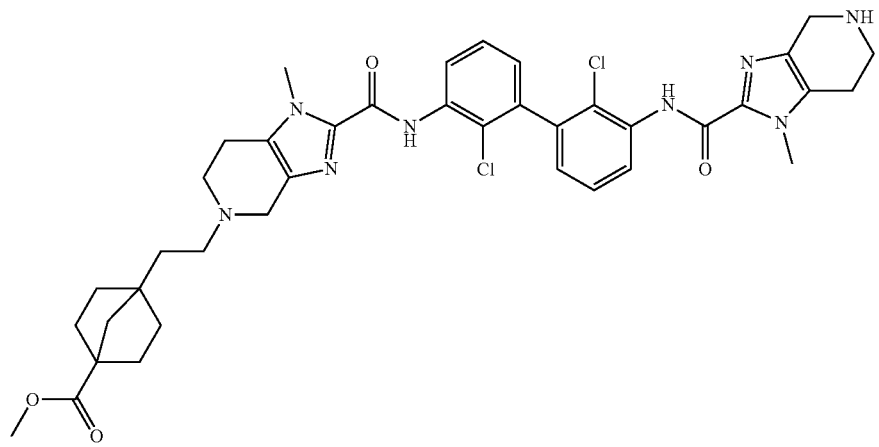 [SMILES: COC(=O)C12CCC(CCN3CCc4c(nc(C(=O)Nc5cccc(-c6cccc(NC(=O)c7nc8c(n7C)CCNC8)c6Cl)c5Cl)n4C)C3)(CC1)C2]

Methyl 4-(2-oxoethyl)bicyclo[2.2.1]heptane-1-carboxylate (Step 7: 43.3 mg, 0.221 mmol) was added to a mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl) carbamoyl)-1-methyl-1,4,6,7-tetrahydro-5H-imidazo[4,5-c]pyridine-5-carboxylate (Step 5: 100 mg, 0.147 mmol) and sodium triacetoxyborohydride (94 mg, 0.441 mmol) in dichloromethane (1.5 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was treated with dichloromethane (1.0 mL) and trifluoroacetic acid (0.5 mL) at room temperature for 1 h. The reaction mixture was concentrated under reduced pressure. The residue was treated with saturated aqueous NaHCO$_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{39}$H$_{45}$Cl$_2$N$_8$O$_4$ (M+H)$^+$: m/z=759.3; found 759.3.

Step 9: 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Lithium hydroxide, monohydrate (11.1 mg, 0.263 mmol) was added to a solution of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylate (Step 8: 40 mg, 0.053 mmol) in THF/MeOH/water (0.2 mL/0.2 mL/0.1 mL). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{38}$H$_{43}$Cl$_2$N$_8$O$_4$ (M+H)$^+$: m/z=745.3; found 745.3. $^1$H NMR (600 MHz, DMSO-d$_6$) δ 9.93 (s, 2H), 9.49 (s, 1H), 8.29 (dd, J=8.2, 1.3 Hz, 1H), 8.28 (dd, J=8.2, 1.3 Hz, 1H), 7.51 (t, J=8.0 Hz, 2H), 7.18 (d, J=7.5, 2H), 4.55-4.44 (m, 1H), 4.28-4.15 (m, 3H), 3.95 (s, 3H), 3.95 (s, 3H), 3.87-3.78 (m, 1H), 3.54-3.38 (m, 3H), 3.32-3.20 (m, 2H), 3.18-2.92 (m, 4H), 2.04-1.82 (m, 4H), 1.58-1.48 (m, 4H), 1.45 (s, 2H), 1.42-1.32 (m, 2H).

Example 2

4-(2-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

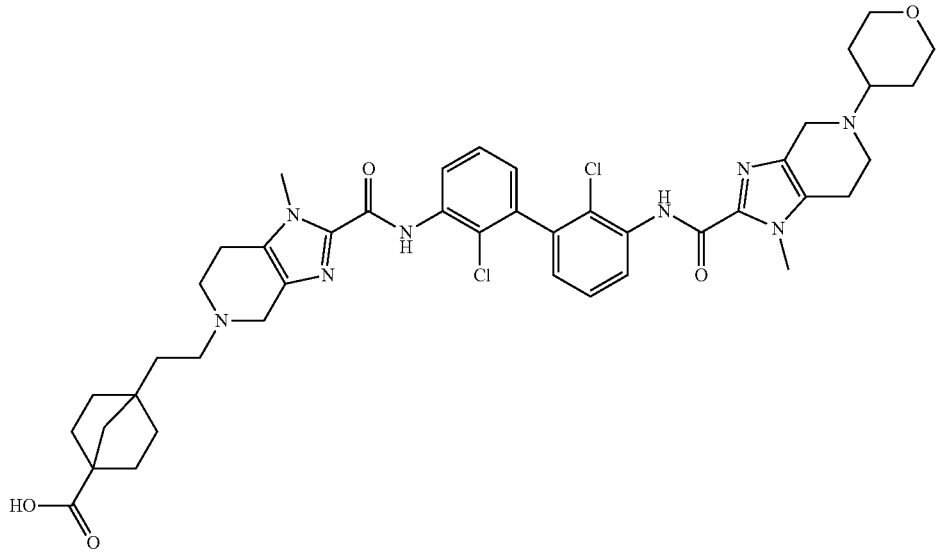

Tetrahydro-4H-pyran-4-one (2.6 mg, 0.026 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 1, Step 8: 10 mg, 0.013 mmol), and sodium triacetoxyborohydride (8.4 mg, 0.039 mmol) in dichloromethane (0.20 mL). After being stirred at room temperature for 2 h, the reaction mixture was quenched with saturated aqueous $NaHCO_3$ solution, and extracted with dichloromethane. The combined organic layers were washed with brine, dried over $Na_2SO_4$, filtered and concentrated under reduced pressure. The residue was dissolved in THF/MeOH/water (0.1 mL/0.1 mL/0.05 mL), and treated with lithium hydroxide, monohydrate (2.8 mg, 0.066 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{43}H_{51}Cl_2N_8O_5$ (M+H)$^+$: m/z=829.3; found 829.4. $^1$H NMR (500 MHz, DMSO-$d_6$) δ 9.93 (s, 1H), 9.92 (s, 1H), 8.31 (dd, J=8.4, 1.4 Hz, 1H), 8.29 (dd, J=8.4, 1.4 Hz, 1H), 7.51 (t, J=7.7 Hz, 2H), 7.18 (d, J=7.6, 1H), 7.18 (d, J=7.6, 1H), 4.56-4.18 (m, 4H), 4.04-3.97 (m, 2H), 3.96 (s, 3H), 3.95 (s, 3H), 3.95-3.78 (m, 2H), 3.68-3.56 (m, 1H), 3.50-3.20 (m, 6H), 3.15-2.94 (m, 4H), 2.13-1.70 (m, 8H), 1.59-1.48 (m, 4H), 1.46 (s, 2H), 1.42-1.32 (m, 2H).

TABLE 1

The compounds in Table 1 were prepared in accordance with the synthetic protocols set forth in Example 2 using the appropriate starting materials.

| Example # | Name | Structure | LC-MS (M + H)$^+$ |
|---|---|---|---|
| 3 | 4-(2-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 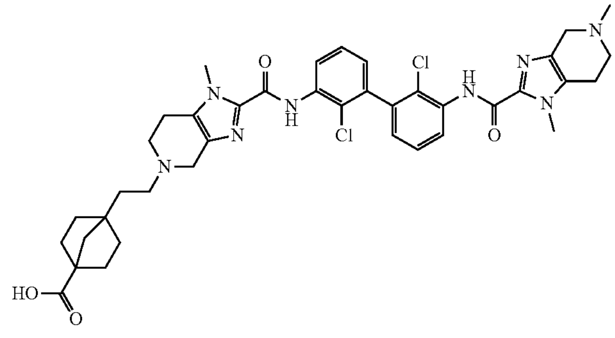 | 759.3 |

TABLE 1-continued

The compounds in Table 1 were prepared in accordance with the synthetic protocols set forth in Example 2 using the appropriate starting materials.

| Example # | Name | Structure | LC-MS (M + H)+ |
|---|---|---|---|
| 4 | 4-(2-(2-((2,2'-dichloro-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 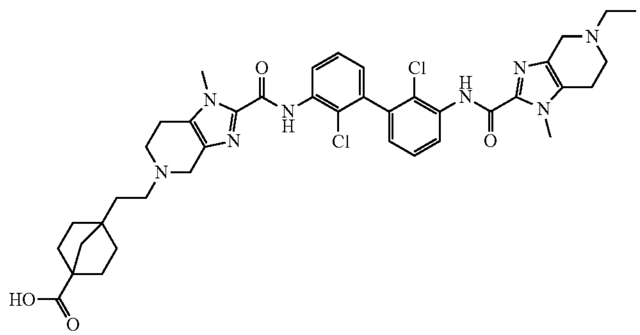 [SMILES: CCN1CCc2c(nc(C(=O)Nc3cccc(-c4cccc(NC(=O)c5nc6c(n5C)CCN(CCC57CCC(C(=O)O)(CC5)C7)C6)c4Cl)c3Cl)n2C)C1] | 773.3 |
| 5 | 4-(2-(2-((2,2'-dichloro-3'-(5-isopropyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 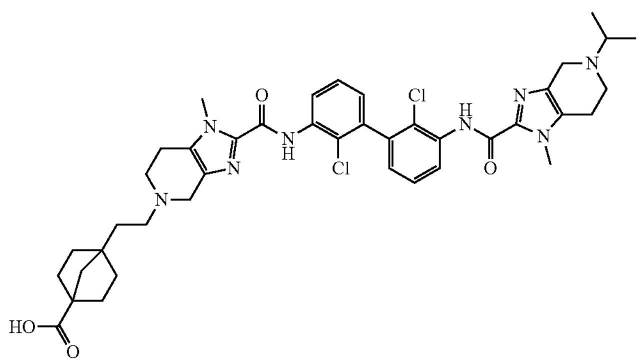 [SMILES: CC(C)N1CCc2c(nc(C(=O)Nc3cccc(-c4cccc(NC(=O)c5nc6c(n5C)CCN(CCC57CCC(C(=O)O)(CC5)C7)C6)c4Cl)c3Cl)n2C)C1] | 787.3 |
| 6 | 4-(2-(2-((2,2'-dichloro-3'-(5-cyclobutyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 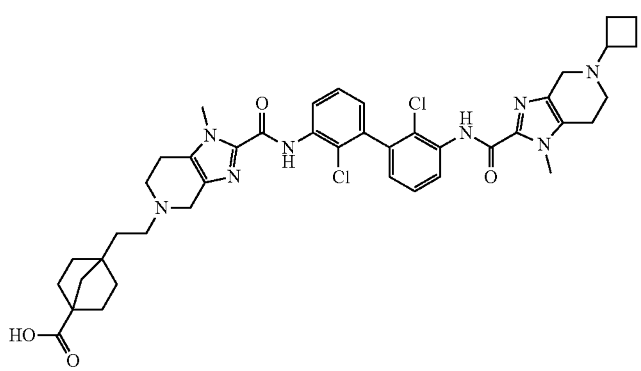 [SMILES: Cn1c(C(=O)Nc2cccc(-c3cccc(NC(=O)c4nc5c(n4C)CCN(C4CCC4)C5)c3Cl)c2Cl)nc2c1CCN(CCC13CCC(C(=O)O)(CC1)C3)C2] | 799.3 |
| 7 | 4-(2-(2-((3'-(5-(1-carbamoylpiperidin-4-yl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 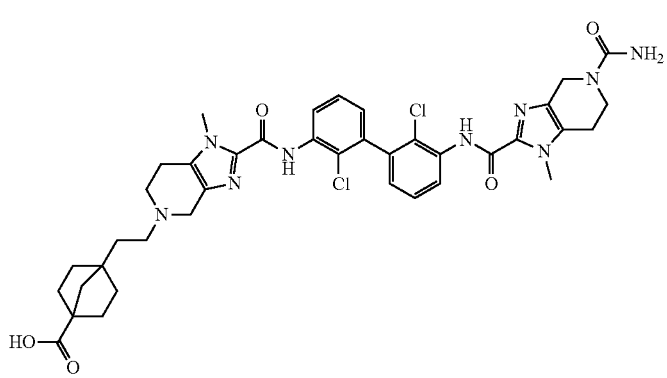 [SMILES: Cn1c(C(=O)Nc2cccc(-c3cccc(NC(=O)c4nc5c(n4C)CCN(C(N)=O)C5)c3Cl)c2Cl)nc2c1CCN(CCC13CCC(C(=O)O)(CC1)C3)C2] | 871.4 |

TABLE 1-continued

The compounds in Table 1 were prepared in accordance with the synthetic protocols set forth in Example 2 using the appropriate starting materials.

| Example # | Name | Structure | LC-MS (M + H)+ |
|---|---|---|---|
| 8 | 4-(2-(2-((2,2'-dichloro-3'-(1-methyl-5-(1-sulfamoylpiperidin-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 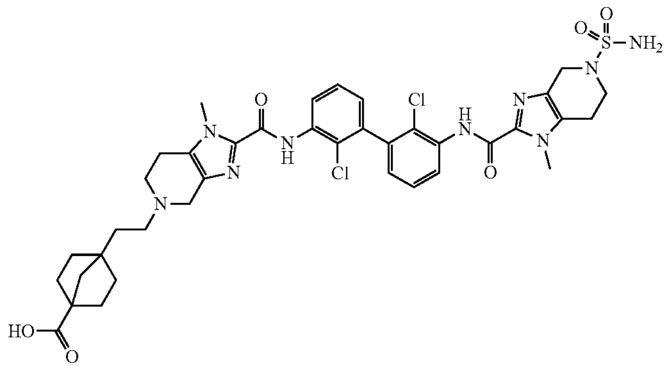 [SMILES: Cn1c(C(=O)Nc2cccc(-c3cccc(NC(=O)c4nc5c(n4C)CCN(S(N)(=O)=O)C5)c3Cl)c2Cl)nc2c1CCN(CCC13CCC(C(=O)O)(CC1)C3)C2] | 907.4 |
| 9 | 4-(2-(2-((3'-(5-((1H-pyrazol-3-yl)methyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 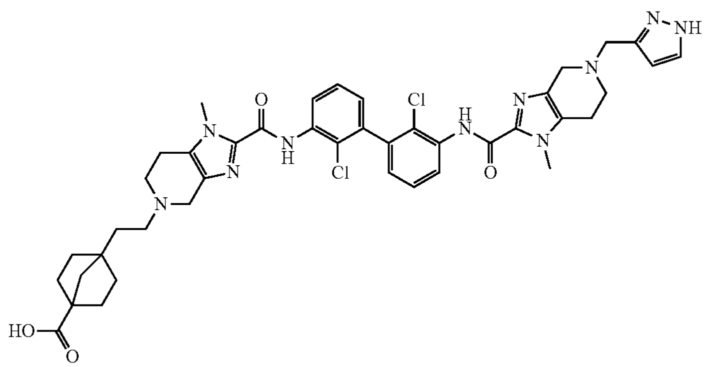 [SMILES: Cn1c(C(=O)Nc2cccc(-c3cccc(NC(=O)c4nc5c(n4C)CCN(Cc4cc[nH]n4)C5)c3Cl)c2Cl)nc2c1CCN(CCC13CCC(C(=O)O)(CC1)C3)C2] | 825.3 |
| 10 | 4-(2-(2-((2,2'-dichloro-3'-(5-(1,3-dihydroxypropan-2-yl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 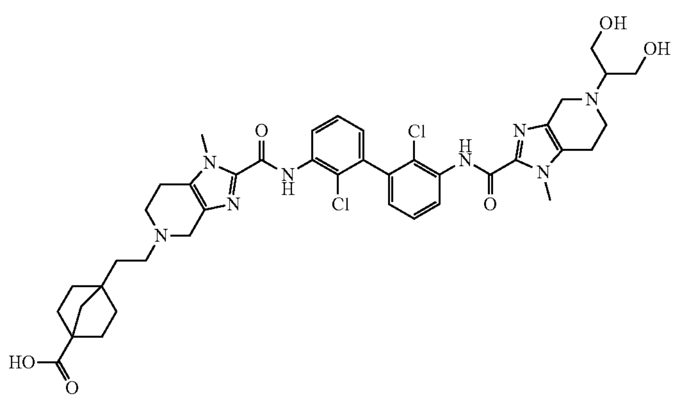 [SMILES: Cn1c(C(=O)Nc2cccc(-c3cccc(NC(=O)c4nc5c(n4C)CCN(C(CO)CO)C5)c3Cl)c2Cl)nc2c1CCN(CCC13CCC(C(=O)O)(CC1)C3)C2] | 819.3 |
| 11 | (R)-4-(2-(2-((2,2'-dichloro-3'-(5-(2,3-dihydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 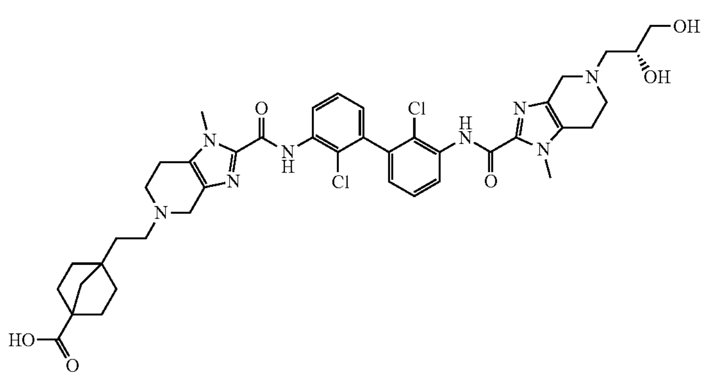 [SMILES: Cn1c(C(=O)Nc2cccc(-c3cccc(NC(=O)c4nc5c(n4C)CCN(C[C@@H](O)CO)C5)c3Cl)c2Cl)nc2c1CCN(CCC13CCC(C(=O)O)(CC1)C3)C2] | 819.3 |

| Example # | Name | Structure | LC-MS (M + H)+ |
|---|---|---|---|
| 12 | (S)-4-(2-(2-((2,2'-dichloro-3'-(5-(2,3-dihydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 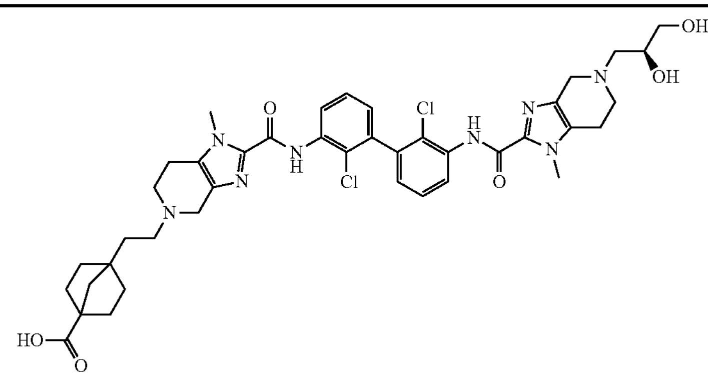 | 819.3 |

Example 13

(R)-4-(2-(2-((2,2'-dichloro-3'-(5-(2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

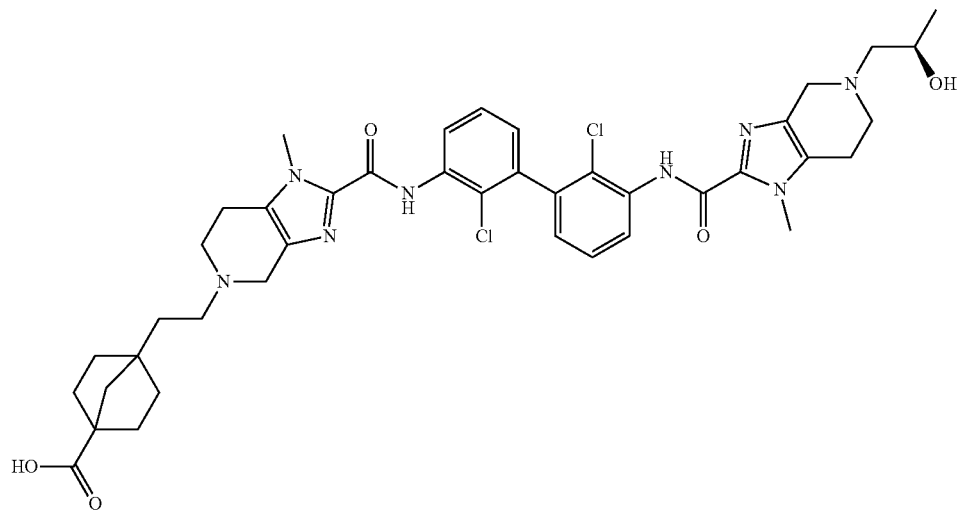 [SMILES: C[C@@H](O)CN1CCc2c(nc(C(=O)Nc3cccc(-c4cccc(NC(=O)c5nc6c(n5C)CCN(CCC57CCC(C(=O)O)(CC5)C7)C6)c4Cl)c3Cl)n2C)C1]

(R)-2-((Tert-butyldimethylsilyl)oxy)propanal (5.0 mg, 0.026 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 1, Step 8: 10 mg, 0.013 mmol), and sodium triacetoxyborohydride (8.4 mg, 0.039 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in methanol (0.10 mL), and then treated with HCl in 1,4-dioxane (4.0 M, 65.8 μL, 0.263 mmol) at 40° C. for 2 h. The reaction mixture was concentrated under reduced pressure. The residue was dissolved in THF/MeOH/water (0.1 mL/0.1 mL/0.05 mL), and then treated with lithium hydroxide, monohydrate (5.5 mg, 0.132 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{41}$H$_{49}$Cl$_2$N$_8$O$_5$ (M+H)$^+$: m/z=803.3; found 803.3. $^1$H NMR (600 MHz, DMSO-d$_6$) δ 9.93 (s, 2H), 8.32-8.25 (m, 2H), 7.51 (t, J=7.9 Hz, 2H), 7.18 (d, J=7.6, 2H), 5.53 (br, 1H), 4.55-4.12 (m, 5H), 3.95 (s, 3H), 3.95 (s, 3H), 3.87-2.92 (m, 12H), 2.04-1.82 (m, 4H), 1.58-1.47 (m, 4H), 1.46 (s, 2H), 1.42-1.32 (m, 2H), 1.13 (d, J=6.1 Hz, 3H).

TABLE 2

The compounds in Table 2 were prepared in accordance with the synthetic protocols set forth in Example 13 using the appropriate starting materials.

| Example # | Name | Structure | LC-MS (M + H)+ |
|---|---|---|---|
| 14 | (S)-4-(2-(2-((2,2'-dichloro-3'-(5-(2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 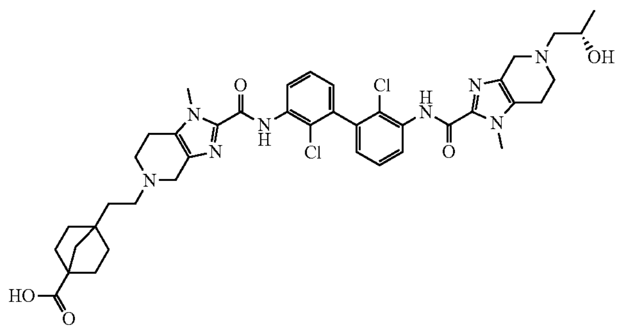 [SMILES: C[C@H](O)CN1CCc2c(nc(C(=O)Nc3cccc(-c4cccc(NC(=O)c5nc6c(n5C)CCN(CCC57CCC(C(=O)O)(CC5)C7)C6)c4Cl)c3Cl)n2C)C1] | 803.3 |
| 15 | 4-(2-(2-((2,2'-dichloro-3'-(5-(2-hydroxyethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 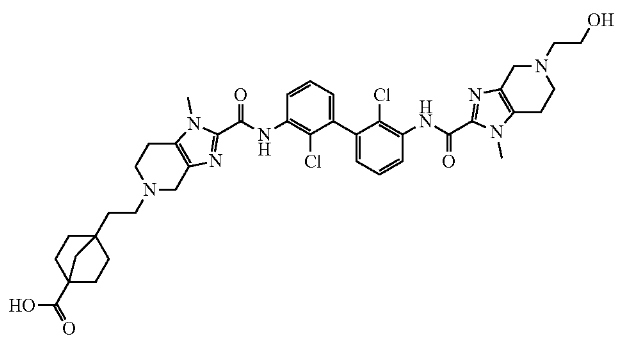 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCO)C2] | 789.3 |
| 16 | 4-(2-(2-((2,2'-dichloro-3'-(5-(3-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 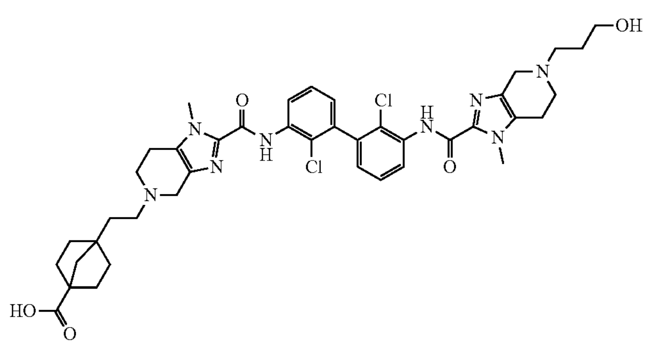 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCCO)C2] | 803.3 |

Example 17

4,4'-((((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid)

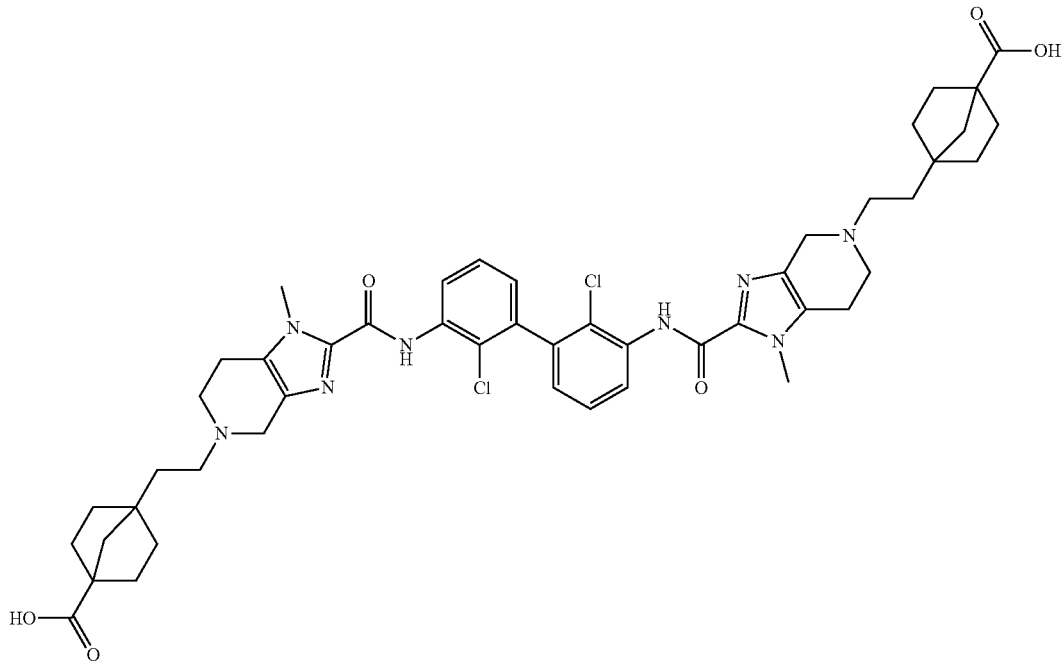 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(C(=O)O)(CC1)C3)C2]

Methyl 4-(2-oxoethyl)bicyclo[2.2.1]heptane-1-carboxylate (Example 1, Step 7: 5.2 mg, 0.026 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 1, Step 8: 10 mg, 0.013 mmol), and sodium triacetoxyborohydride (8.37 mg, 0.039 mmol) in dichloromethane (0.20 mL). After being stirred at room temperature for 2 h, the reaction mixture was quenched with saturated aqueous $NaHCO_3$ solution, and extracted with dichloromethane. The combined organic layers were washed with brine, dried over $Na_2SO_4$, filtered and concentrated under reduced pressure. The residue was dissolved in THF/MeOH/water (0.1 mL/0.1 mL/0.05 mL), and treated with lithium hydroxide, monohydrate (5.5 mg, 0.132 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{48}H_{57}Cl_2N_8O_6$ (M+H)$^+$: m/z=911.4; found 911.4. $^1$H NMR (600 MHz, DMSO-$d_6$) δ 12.08 (s, 2H), 9.93 (s, 2H), 8.29 (d, J=8.1 Hz, 2H), 7.51 (t, J=7.9 Hz, 2H), 7.18 (d, J=7.7 Hz, 2H), 4.56-4.44 (m, 2H), 4.30-4.18 (m, 2H), 3.95 (s, 6H), 3.87-3.78 (m, 2H), 3.52-3.20 (m, 6H), 3.14-2.94 (m, 4H), 2.04-1.82 (m, 8H), 1.58-1.48 (m, 8H), 1.46 (s, 4H), 1.42-1.32 (m, 4H).

TABLE 3

The compounds in Table 3 were prepared in accordance with the synthetic protocols set forth in Example 17 using the appropriate starting materials.

| Example # | Name/$^1$H NMR | Structure | LC-MS (M + H)$^+$ |
|---|---|---|---|
| 18 | 4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 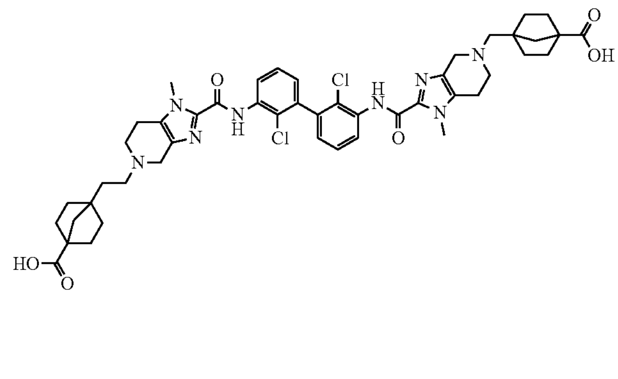 | 897.4 |

TABLE 3-continued

The compounds in Table 3 were prepared in accordance with the synthetic protocols set forth in Example 17 using the appropriate starting materials.

| Example # | Name/$^1$H NMR | Structure | LC-MS (M + H)$^+$ |
|---|---|---|---|
| | $^1$H NMR (500 MHz, DMSO-d$_6$) δ 9.93 (s, 1H), 9.92(s, 1H), 8.30 (dd, J = 8.3, 1.6 Hz, 1H), 8.29 (dd, J = 8.3, 1.6 Hz, 1H), 7.51 (t, J = 7.9 Hz, 2H), 7.18 (dd, J = 7.6, 1.6 Hz, 2H), 4.58-4.45 (m, 2H), 4.36-4.18 (m, 2H), 3.96 (s, 3H), 3.96 (s, 3H), 3.88-3.72 (m, 2H), 3.60-3.38 (m, 4H), 3.34-3.22 (m, 2H), 3.14-2.95 (m, 4H), 2.05-1.83 (m, 6H), 1.80-1.72 (m, 2H), 1.67 (s, 2H), 1.63-1.48 (m, 8H), 1.46 (s, 2H), 1.42-1.32 (m, 2H). | | |
| 19 | 4-(2-(2-((3'-(5-(carboxymethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 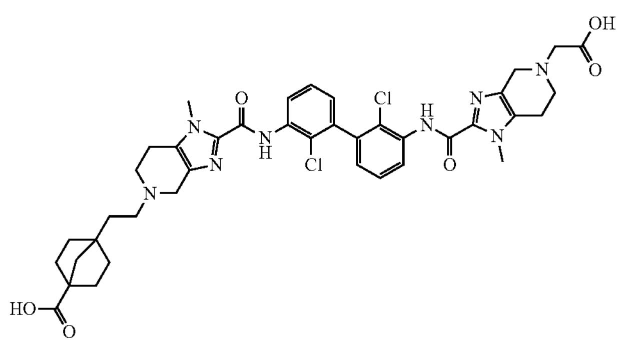 [SMILES: Cn1c(C(=O)Nc2cccc(-c3cccc(NC(=O)c4nc5c(n4C)CCN(CC(=O)O)C5)c3Cl)c2Cl)nc2c1CCN(CCC13CCC(C(=O)O)(CC1)C3)C2] | 803.3 |
| 20 | 4-(2-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 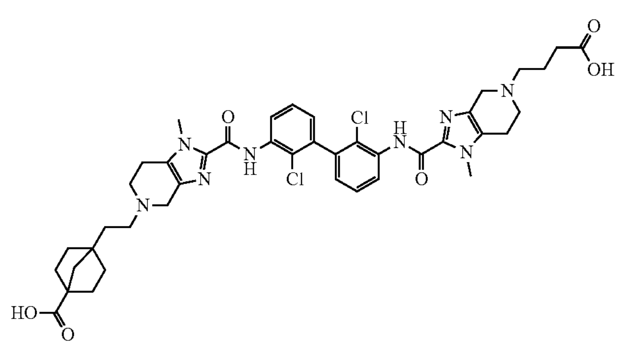 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCCC(=O)O)C2] | 831.3 |
| 21 | 4-(2-(2-((3'-(5-(2-carboxy-2-methylpropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 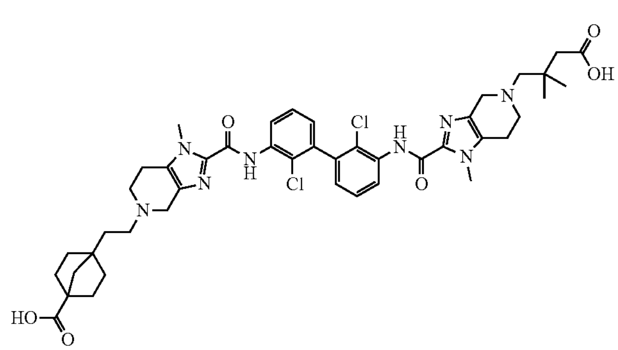 [SMILES: Cn1c(C(=O)Nc2cccc(-c3cccc(NC(=O)c4nc5c(n4C)CCN(CC(C)(C)CC(=O)O)C5)c3Cl)c2Cl)nc2c1CCN(CCC13CCC(C(=O)O)(CC1)C3)C2] | 845.3 |

TABLE 3-continued

The compounds in Table 3 were prepared in accordance with the synthetic protocols set forth in Example 17 using the appropriate starting materials.

| Example # | Name/¹H NMR | Structure | LC-MS (M + H)⁺ |
|---|---|---|---|
| 22 | 4-(2-(2-((3'-(5-((1-carboxycyclopropyl)methyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 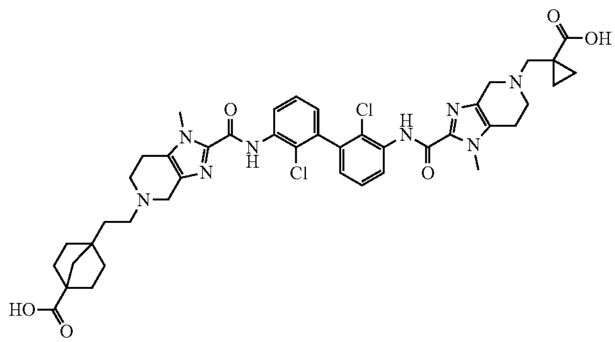 [SMILES: Cn1c(C(=O)Nc2cccc(-c3cccc(NC(=O)c4nc5c(n4C)CCN(CC4(C(=O)O)CC4)C5)c3Cl)c2Cl)nc2c1CCN(CCC13CCC(C(=O)O)(CC1)C3)C2] | 843.3 |
| 23 | 4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)bicyclo[2.2.2]octane-1-carboxylic acid | 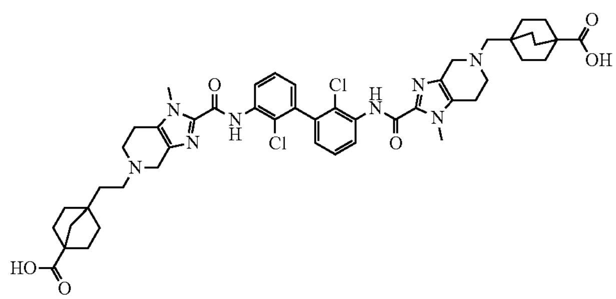 [SMILES: Cn1c(C(=O)Nc2cccc(-c3cccc(NC(=O)c4nc5c(n4C)CCN(CC46CCC(C(=O)O)(CC4)CC6)C5)c3Cl)c2Cl)nc2c1CCN(CCC13CCC(C(=O)O)(CC1)C3)C2] | 911.4 |
| 24 | 3-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)bicyclo[1.1.1]pentane-1-carboxylic acid | 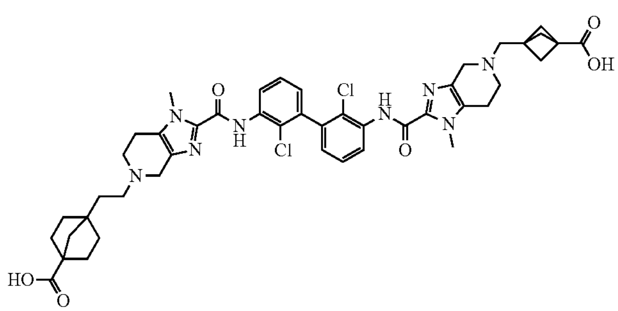 [SMILES: Cn1c(C(=O)Nc2cccc(-c3cccc(NC(=O)c4nc5c(n4C)CCN(CC46CC(C(=O)O)(C4)C6)C5)c3Cl)c2Cl)nc2c1CCN(CCC13CCC(C(=O)O)(CC1)C3)C2] | 869.4 |
| 25 | 4-(2-(2-((3'-(5-(4-carboxyphenethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 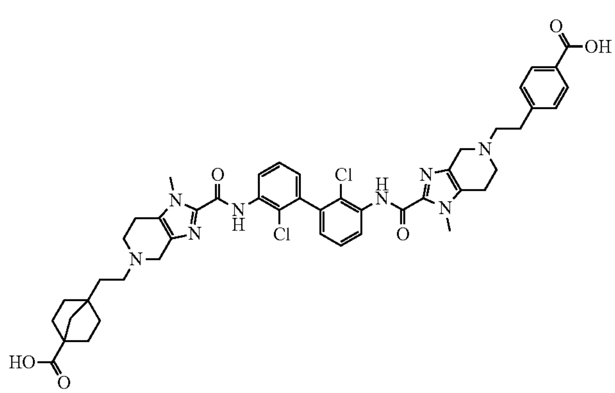 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCc1ccc(C(=O)O)cc1)C2] | 893.4 |

TABLE 3-continued

The compounds in Table 3 were prepared in accordance with the synthetic protocols set forth in Example 17 using the appropriate starting materials.

| Example # | Name/¹H NMR | Structure | LC-MS (M + H)⁺ |
|---|---|---|---|
| 26 | 5-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)-1H-pyrazole-3-carboxylic acid | 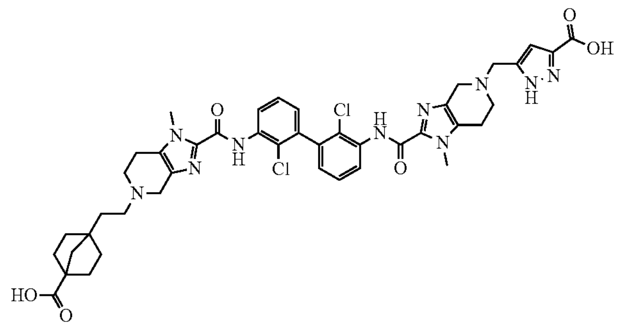 [SMILES: Cn1c(C(=O)Nc2cccc(-c3cccc(NC(=O)c4nc5c(n4C)CCN(Cc4cc(C(=O)O)n[nH]4)C5)c3Cl)c2Cl)nc2c1CCN(CCC13CCC(C(=O)O)(CC1)C3)C2] | 869.3 |

Example 27

4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

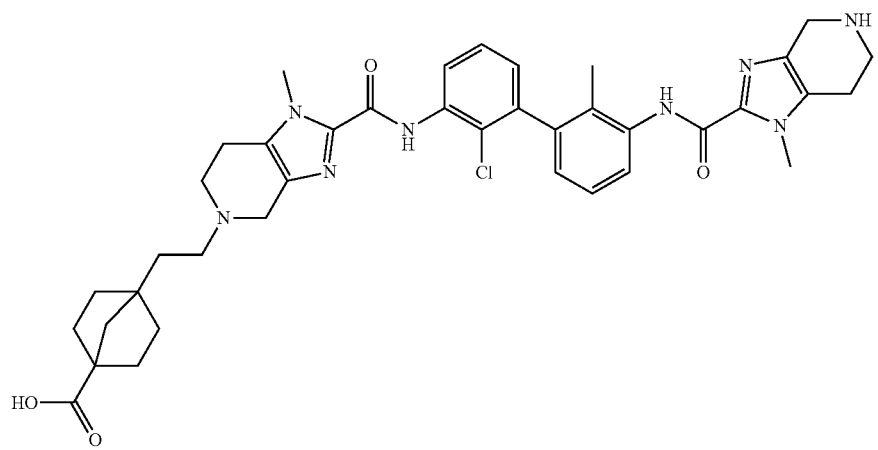 [SMILES: Cc1c(NC(=O)c2nc3c(n2C)CCNC3)cccc1-c1cccc(NC(=O)c2nc3c(n2C)CCN(CCC24CCC(C(=O)O)(CC2)C4)C3)c1Cl]

Step 1: tert-butyl 2-((3-bromo-2-methylphenyl)carbamoyl)-1-methyl-1,4,6,7-tetrahydro-5H-imidazo[4,5-c]pyridine-5-carboxylate

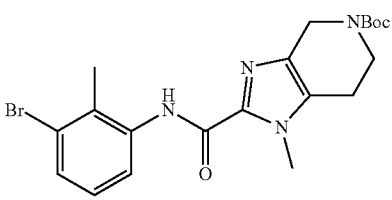

Potassium tert-butoxide in THF (1.0 M, 13.54 mL, 13.54 mmol) was added to a solution of 5-tert-butyl 2-methyl 1-methyl-6,7-dihydro-1H-imidazo[4,5-c]pyridine-2,5(4H)-dicarboxylate (Example 1, Step 2: 2.00 g, 6.77 mmol) and 3-bromo-2-methylaniline (1.26 g, 6.77 mmol) in tetrahydrofuran (34.0 mL). After being stirred at room temperature for 30 min, the reaction mixture was quenched with water, and extracted with ethyl acetate. The combined organic layers were washed with brine, dried over Na₂SO₄, filtered, and concentrated under reduced pressure. The residue was purified by flash chromatography on a silica gel column eluting with 0-50% ethyl acetate in hexanes to afford the desired product. LC-MS calculated for $C_{20}H_{26}BrN_4O_3$ (M+H)⁺: m/z=449.1/451.1; found 449.1/451.1.

Step 2: tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate Step 3: tert-butyl 2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

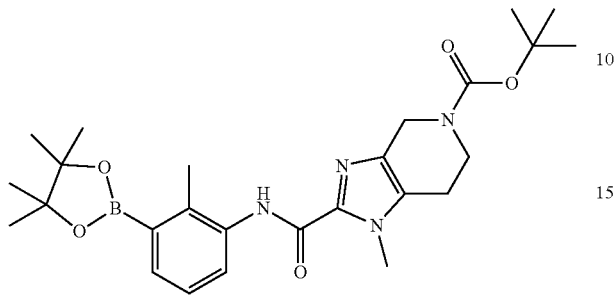

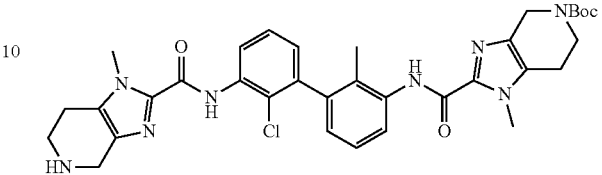

A solution of tert-butyl 2-((3-bromo-2-chlorophenyl)carbamoyl)-1-methyl-1,4,6,7-tetrahydro-5H-imidazo[4,5-c]pyridine-5-carboxylate (Example 1, Step 3: 1.0 g, 2.129 mmol) in dichloromethane (8.0 mL) and trifluoroacetic acid (4.0 mL) was stirred at room temperature for 1 h. The reaction mixture was concentrated under reduced pressure. A mixture of the above residue, tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Step 2: 1.162 g, 2.342 mmol), sodium carbonate (1.128 g, 10.64 mmol) and [1,1-bis(di-cyclohexylphosphino)ferrocene]dichloropalladium(II) (0.161 g, 0.213 mmol) in 1,4-dioxane (12.0 mL) and water (6.0 mL) was purged with nitrogen and then stirred at 110° C. for 2 h. After being cooled to room temperature, the reaction mixture was diluted with water and extracted with dichloromethane. The combined organic layers were dried over $Na_2SO_4$, filtered, and concentrated under reduced pressure. The residue was purified by flash chromatography on a silica gel column eluting with 0-10% methanol in dichloromethane to afford the desired product. LC-MS calculated for $C_{34}H_{40}ClN_8O_4$ (M+H)$^+$: m/z=659.3; found 659.4.

A mixture of tert-butyl 2-((3-bromo-2-methylphenyl)carbamoyl)-1-methyl-1,4,6,7-tetrahydro-5H-imidazo[4,5-c]pyridine-5-carboxylate (Step 1: 600 mg, 1.34 mmol), 4,4,5,5,4',4',5',5'-octamethyl-[2,2']bi[[1,3,2]dioxaborolanyl](509 mg, 2.00 mmol), [1,1'-bis(diphenylphosphino)ferrocene]dichloropalladium(II) complexed with dichloromethane (1:1) (109 mg, 0.14 mmol) and potassium acetate (393 mg, 4.01 mmol) in 1,4-dioxane (13.0 mL) was purged with nitrogen and then stirred at 100° C. for 2 h. The reaction mixture was cooled to room temperature, diluted with dichloromethane, and then filtered through Celite. The filtrate was concentrated, and the residue was purified by flash chromatography on a silica gel column eluting with 0-30% ethyl acetate in hexanes to afford the desired product. LC-MS calculated for $C_{26}H_{38}BN_4O_5$ (M+H)$^+$: m/z=497.3; found 497.3.

Step 4: methyl 4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-o]pyridin-5-yl)ethyl)bicyclo[2.2.1]heptane-1-carboxylate

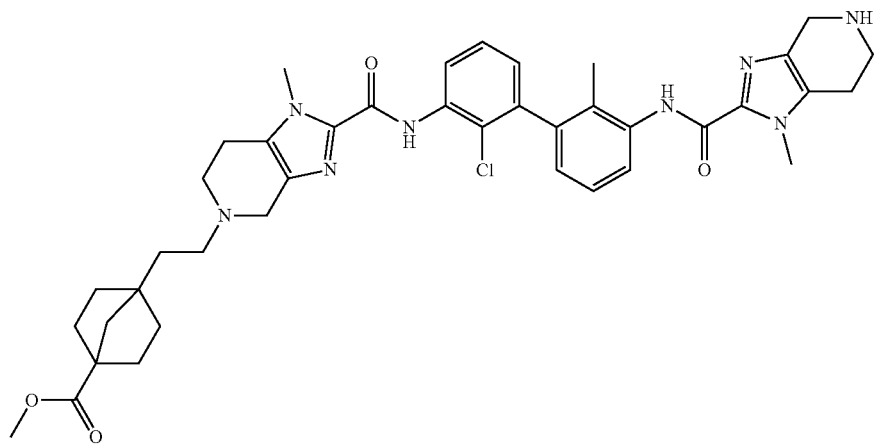 [SMILES: COC(=O)C12CCC(CCN3CCc4c(nc(C(=O)Nc5cccc(-c6cccc(NC(=O)c7nc8c(n7C)CCNC8)c6C)c5Cl)n4C)C3)(CC1)C2]

Methyl 4-(2-oxoethyl)bicyclo[2.2.1]heptane-1-carboxylate (Example 1, Step 7: 44.7 mg, 0.228 mmol) was added to a mixture of tert-butyl 2-42'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 3: 100 mg, 0.152 mmol) and sodium triacetoxyborohydride (96 mg, 0.455 mmol) in dichloromethane (1.5 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was treated with dichloromethane (1.0 mL) and trifluoroacetic acid (0.5 mL) at room temperature for 1 h. The mixture was concentrated under reduced pressure. The residue was treated with saturated aqueous NaHCO$_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{40}$H$_{48}$ClN$_8$O$_4$ (M+H)$^+$: m/z=739.3; found 739.3.

Step 5: 4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Lithium hydroxide, monohydrate (2.8 mg, 0.068 mmol) was added to a solution of methyl 4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Step 4: 10 mg, 0.014 mmol) in THF/MeOH/water (0.1 mL/0.1 mL/0.05 mL). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{39}$H$_{46}$ClN$_8$O$_4$ (M+H)$^+$: m/z=725.3; found 725.3.

Example 28

4-(2-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

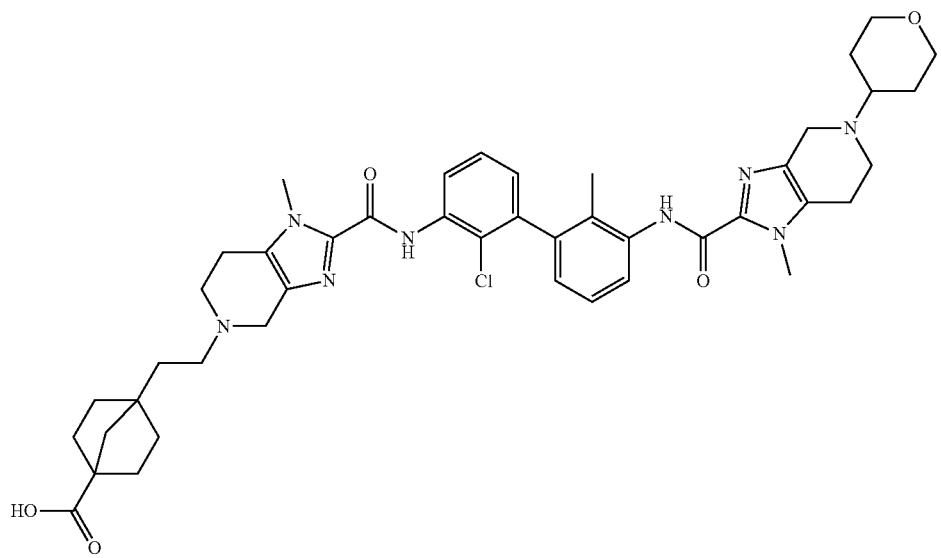 [SMILES: Cc1c(NC(=O)c2nc3c(n2C)CCN(C2CCOCC2)C3)cccc1-c1cccc(NC(=O)c2nc3c(n2C)CCN(CCC24CCC(C(=O)O)(CC2)C4)C3)c1Cl]

Tetrahydro-4H-pyran-4-one (2.7 mg, 0.027 mmol) was added to a mixture of methyl 4-(2-(2-((2-chloro-T-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 27, Step 4: 10 mg, 0.014 mmol), and sodium triacetoxyborohydride (8.6 mg, 0.041 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in THF/MeOH/water (0.1 mL/0.1 mL/0.05 mL), and treated with lithium hydroxide, monohydrate (2.8 mg, 0.068 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{44}$H$_{54}$ClN$_8$O$_5$ (M+H)$^+$: m/z=809.4; found 809.4.

TABLE 4

The compounds in Table 4 were prepared in accordance with the synthetic protocols set forth in Example 28 using the appropriate starting materials.

| Example # | Name | Structure | LC-MS (M + H)+ |
|---|---|---|---|
| 29 | 4-(2-(2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 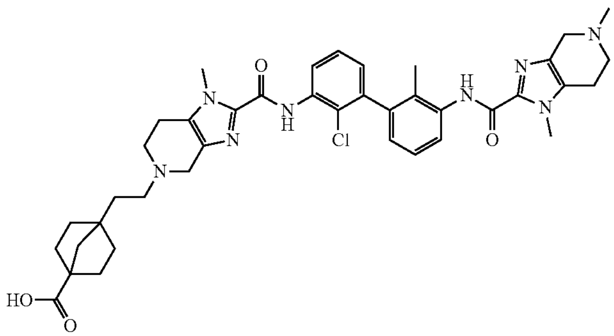 [SMILES: Cc1c(NC(=O)c2nc3c(n2C)CCN(C)C3)cccc1-c1cccc(NC(=O)c2nc3c(n2C)CCN(CCC24CCC(C(=O)O)(CC2)C4)C3)c1Cl] | 739.3 |
| 30 | 4-(2-(2-((3'-(5-(1-carbamoylpiperidin-4-yl)-1-methyl-4,5,6,7-tetrahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 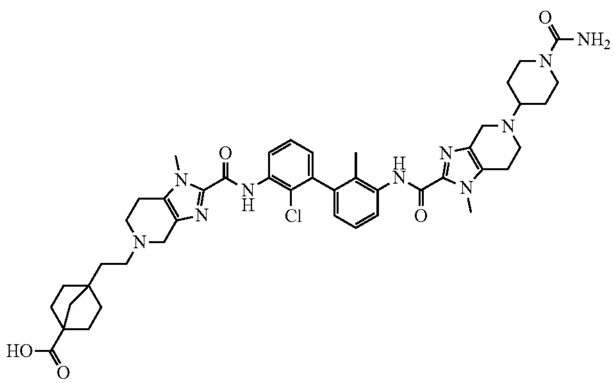 [SMILES: Cc1c(NC(=O)c2nc3c(n2C)CCN(C2CCN(C(N)=O)CC2)C3)cccc1-c1cccc(NC(=O)c2nc3c(n2C)CCN(CCC24CCC(C(=O)O)(CC2)C4)C3)c1Cl] | 851.4 |

Example 31

(R)-4-(2-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

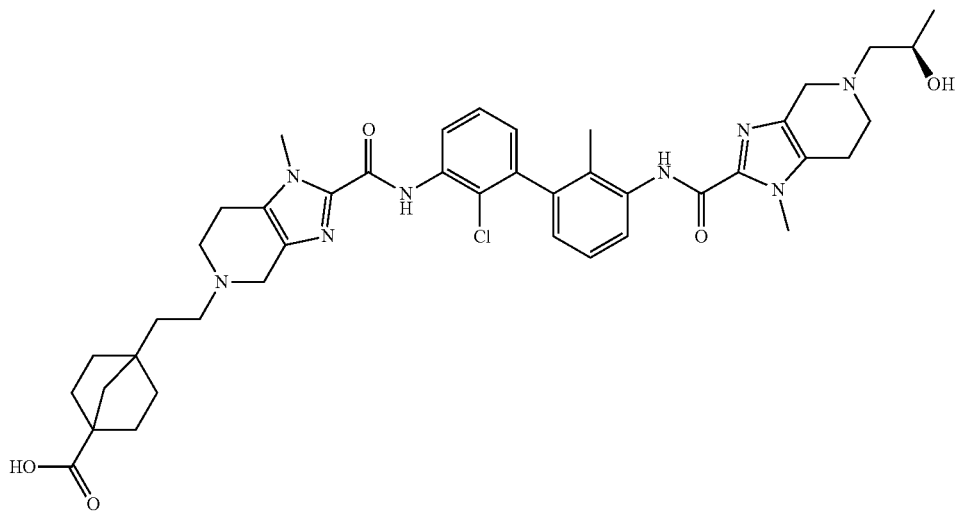 [SMILES: Cc1c(NC(=O)c2nc3c(n2C)CCN(C[C@@H](C)O)C3)cccc1-c1cccc(NC(=O)c2nc3c(n2C)CCN(CCC24CCC(C(=O)O)(CC2)C4)C3)c1Cl]

(R)-2-((Tert-butyldimethylsilyl)oxy)propanal (5.1 mg, 0.027 mmol) was added to a mixture of methyl 4-(2-(2-((2-chloro-T-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 27, Step 4: 10 mg, 0.014 mmol), and sodium triacetoxyborohydride (8.6 mg, 0.041 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in methanol (0.10 mL), and then treated with HCl in 1,4-dioxane (4.0 M, 67.6 µL, 0.271 mmol) at 40° C. for 2 h. The reaction mixture was concentrated under reduced pressure. The residue was dissolved in THF/MeOH/water (0.1 mL/0.1 mL/0.05 mL), and then treated with lithium hydroxide, monohydrate (5.7 mg, 0.135 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{42}$H$_{52}$ClN$_8$O$_5$ (M+H)$^+$: m/z=783.4; found 783.4. $^1$H NMR (600 MHz, DMSO-d$_6$) δ 9.94 (s, 1H), 9.91 (s, 1H), 8.25 (d, J=8.1 Hz, 1H), 7.62 (t, J=8.3 Hz, 1H), 7.48 (t, J=7.9 Hz, 1H), 7.32 (t, J=7.8 Hz, 1H), 7.11 (dd, J=7.5, 1.4 Hz, 1H), 7.04 (d, J=7.5 Hz, 1H) 5.55 (br, 1H), 4.55-4.14 (m, 5H), 3.95 (s, 3H), 3.91 (s, 3H), 3.88-2.95 (m, 12H), 2.04-1.82 (m, 7H), 1.58-1.47 (m, 4H), 1.46 (s, 2H), 1.42-1.32 (m, 2H), 1.14 (d, J=6.0 Hz, 3H).

TABLE 5

The compounds in Table 5 were prepared in accordance with the synthetic protocols set forth in Example 31 using the appropriate starting materials.

| Example # | Name | Structure | LC-MS (M + H)$^+$ |
|---|---|---|---|
| 32 | (S)-4-(2-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 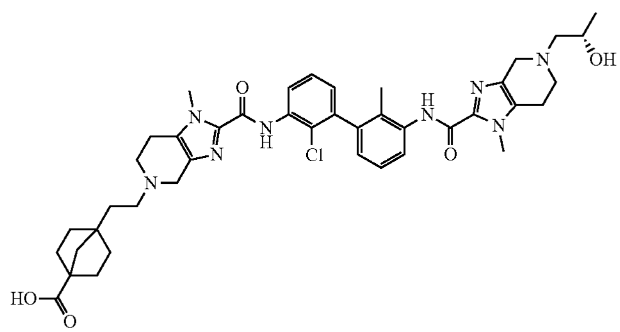 [SMILES: Cc1c(NC(=O)c2nc3c(n2C)CCN(C[C@H](C)O)C3)cccc1-c1cccc(NC(=O)c2nc3c(n2C)CCN(CCC24CCC(C(=O)O)(CC2)C4)C3)c1Cl] | 783.4 |
| 33 | 4-(2-(2-((2-chloro-3'-(5-(2-hydroxyethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 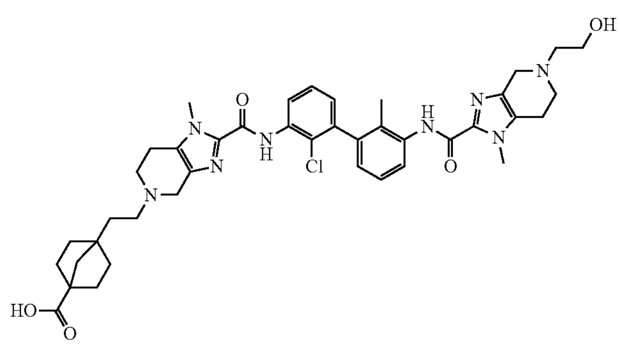 [SMILES: Cc1c(NC(=O)c2nc3c(n2C)CCN(CCO)C3)cccc1-c1cccc(NC(=O)c2nc3c(n2C)CCN(CCC24CCC(C(=O)O)(CC2)C4)C3)c1Cl] | 769.4 |

Example 34

4,4'-(((((2-chloro-2'-methyl-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid)

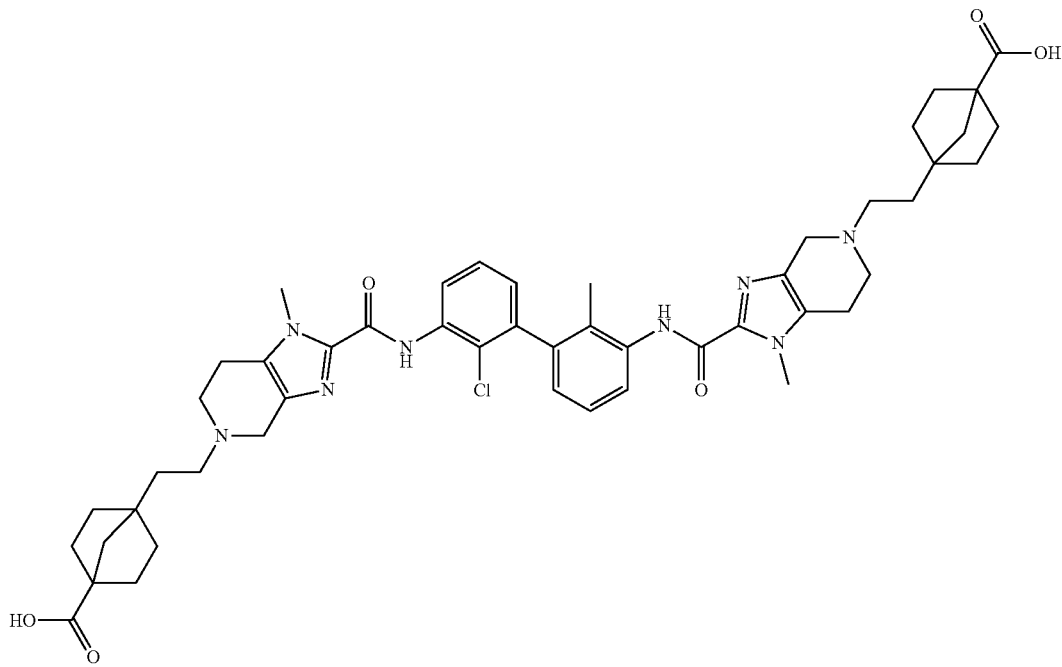 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CCC24CCC(C(=O)O)(CC2)C4)C3)c1Cl]

Methyl 4-(2-oxoethyl)bicyclo[2.2.1]heptane-1-carboxylate (Example 1, Step 7: 5.3 mg, 0.027 mmol) was added to a mixture of methyl 4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 27, Step 4: 10 mg, 0.014 mmol), and sodium triacetoxyborohydride (8.6 mg, 0.041 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in THF/MeOH/water (0.1 mL/0.1 mL/0.05 mL), and then treated with lithium hydroxide, monohydrate (5.7 mg, 0.135 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{49}$H$_{60}$ClN$_8$O$_6$ (M+H)$^+$: m/z=891.4; found 891.4.

TABLE 6

The compounds in Table 6 were prepared in accordance with the synthetic protocols set forth in Example 34 using the appropriate starting materials.

| Example # | Name | Structure | LC-MS (M + H)$^+$ |
|---|---|---|---|
| 35 | 4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2'-chloro-2-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 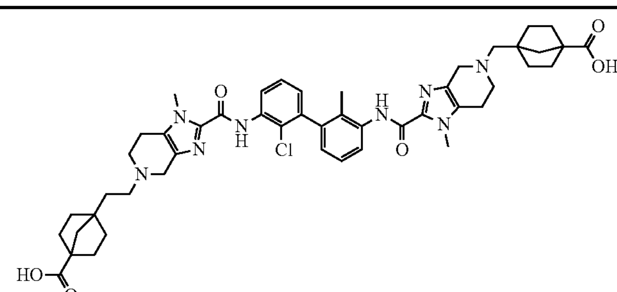 | 877.4 |

TABLE 6-continued

The compounds in Table 6 were prepared in accordance with the synthetic protocols set forth in Example 34 using the appropriate starting materials.

| Example # | Name | Structure | LC-MS (M + H)+ |
|---|---|---|---|
| 36 | 4-(2-(2-((3'-(5-(4-carboxyphenethyl)-1-methyl-4,5,6,7-tetrahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 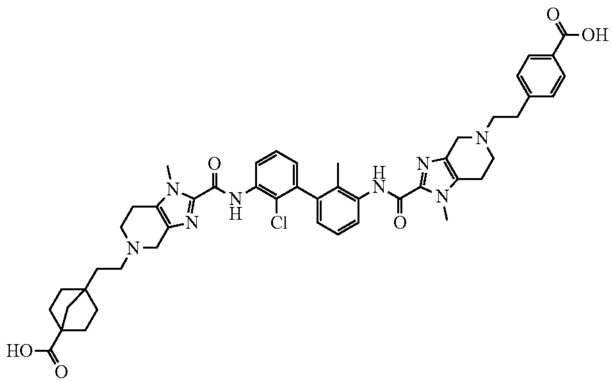 [SMILES: Cc1c(NC(=O)c2nc3c(n2C)CCN(CCc2ccc(C(=O)O)cc2)C3)cccc1-c1cccc(NC(=O)c2nc3c(n2C)CCN(CCC24CCC(C(=O)O)(CC2)C4)C3)c1Cl] | 873.4 |

Example 37

4-(2-(2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

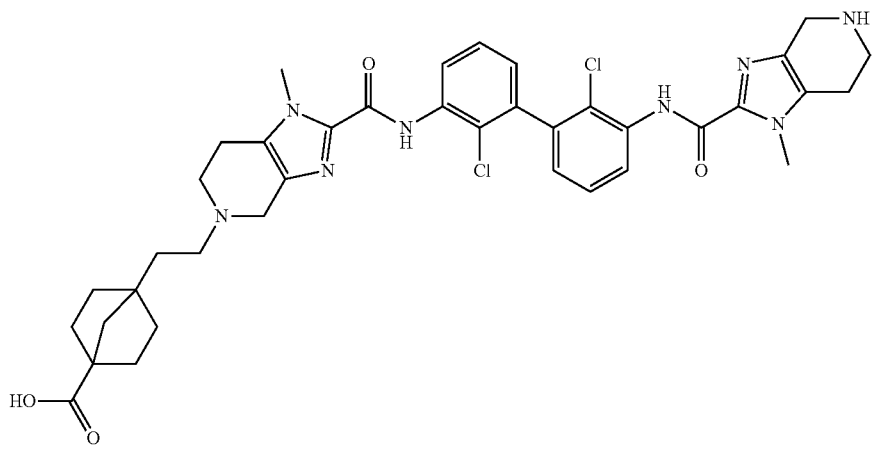 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCNC2]

Step 1: tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

A solution of tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Example 27, Step 2: 254 mg, 0.511 mmol) in dichloromethane (1.0 mL) and trifluoroacetic acid (0.5 mL) was stirred at room temperature for 30 min. The reaction mixture was concentrated under reduced pressure. A mixture of the residue, tert-butyl 2-((3-bromo-2-chlorophenyl)carbamoyl)-1-methyl-1,4,6,7-tetrahydro-5H-imidazo[4,5-c]pyridine-5-carboxylate (Example 1, Step 3: 200 mg, 0.426 mmol), sodium carbonate (226 mg, 2.129 mmol) and [1,1'-bis(di-cyclohexylphosphino)ferrocene]dichloropalladium (II) (32.3 mg, 0.043 mmol) in 1,4-dioxane (2.0 mL) and water (2.0 mL) was purged with nitrogen and then stirred at 110° C. for 2 h. After being cooled to room temperature, the reaction mixture was diluted with water and extracted with dichloromethane. The combined organic layers were washed with brine, dried over $Na_2SO_4$, filtered, and concentrated under reduced pressure. The residue was purified by flash chromatography on a silica gel column eluting with 0-10% methanol in dichloromethane to afford the desired product. LC-MS calculated for $C_{34}H_{40}ClN_8O_4$ (M+H)+: m/z=659.3; found 659.3.

Step 2: methyl 4-(2-(2-(2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-o]pyridin-5-yl)ethyl)bicyclo[2.2.1]heptane-1-carboxylate

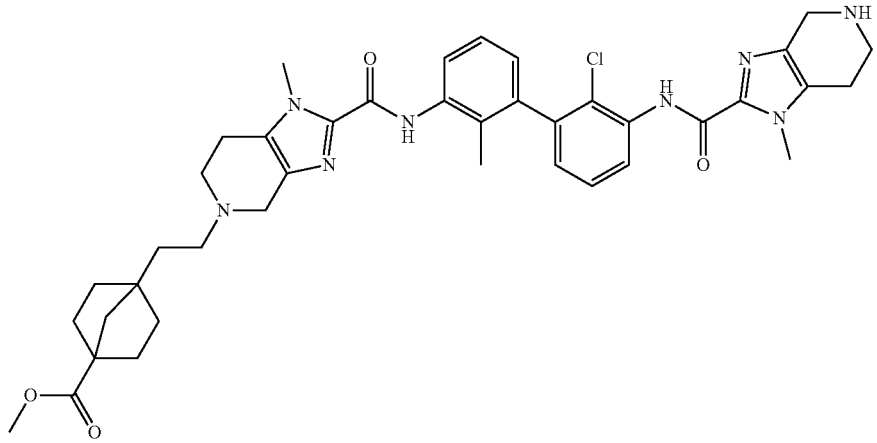 [SMILES: COC(=O)C12CCC(CCN3CCc4c(nc(C(=O)Nc5cccc(-c6cccc(NC(=O)c7nc8c(n7C)CCNC8)c6Cl)c5C)n4C)C3)(CC1)C2]

Methyl 4-(2-oxoethyl)bicyclo[2.2.1]heptane-1-carboxylate (Example 1, Step 7: 44.7 mg, 0.228 mmol) was added to a mixture of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 100 mg, 0.152 mmol), and sodium triacetoxyborohydride (96 mg, 0.455 mmol) in dichloromethane (1.5 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was treated with dichloromethane (1.0 mL) and trifluoroacetic acid (0.5 mL) at room temperature for 1 h. The mixture was concentrated under reduced pressure. The residue was treated with saturated aqueous NaHCO$_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{40}$H$_{48}$ClN$_8$O$_4$ (M+H)$^+$: m/z=739.3; found 739.3.

Step 3: 4-(2-(2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Lithium hydroxide, monohydrate (2.8 mg, 0.068 mmol) was added to a solution of methyl 4-(2-(2-42'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Step 2: 10.0 mg, 0.014 mmol) in THF/MeOH/water (0.1 mL/0.1 mL/0.05 mL). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{39}$H$_{46}$ClN$_8$O$_4$ (M+H)$^+$: m/z=725.3; found 725.3.

Example 38

4-(2-(2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

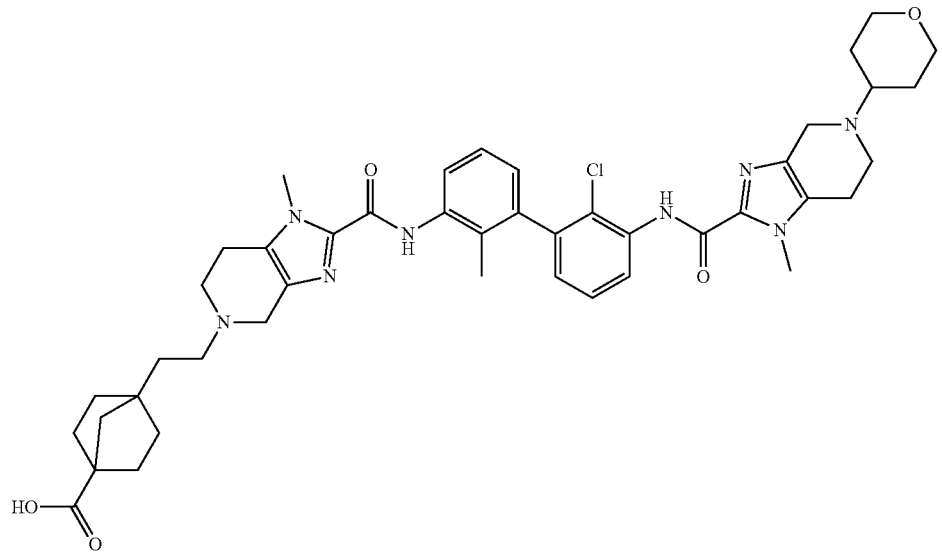 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C2CCOCC2)C3)c1Cl]

Tetrahydro-4H-pyran-4-one (2.7 mg, 0.027 mmol) was added to a mixture of methyl 4-(2-(2-42'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 37, Step 2: 10.0 mg, 0.014 mmol), and sodium triacetoxyborohydride (8.6 mg, 0.041 mmol) in dichloromethane (0.20 mL). After being stirred at room temperature for 2 h, the reaction mixture was quenched with saturated aqueous $NaHCO_3$ solution, and extracted with dichloromethane. The combined organic layers were washed with brine, dried over $Na_2SO_4$, filtered and concentrated under reduced pressure. The residue was dissolved in THF/MeOH/water (0.1 mL/0.1 mL/0.05 mL), and treated with lithium hydroxide, monohydrate (2.8 mg, 0.068 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{44}H_{54}ClN_8O_5$ (M+H)$^+$: m/z=809.4; found 809.4.

TABLE 7

The compounds in Table 7 were prepared in accordance with the synthetic protocols set forth in Example 38 using the appropriate starting materials.

| Example # | Name | Structure | LC-MS (M + H)$^+$ |
|---|---|---|---|
| 39 | 4-(2-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 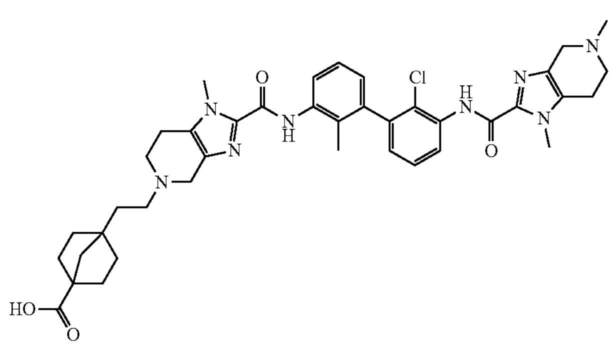 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C)C3)c1Cl] | 739.3 |

TABLE 7-continued

The compounds in Table 7 were prepared in accordance with the synthetic protocols set forth in Example 38 using the appropriate starting materials.

| Example # | Name | Structure | LC-MS (M + H)+ |
|---|---|---|---|
| 40 | 4-(2-(2-((3'-(5-(1-carbamoylpiperidin-4-yl)-1-methyl-4,5,6,7-tetrahydro-1H-imidazo[4,5-c]pyridine-2-carboxamido)-2'-chloro-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 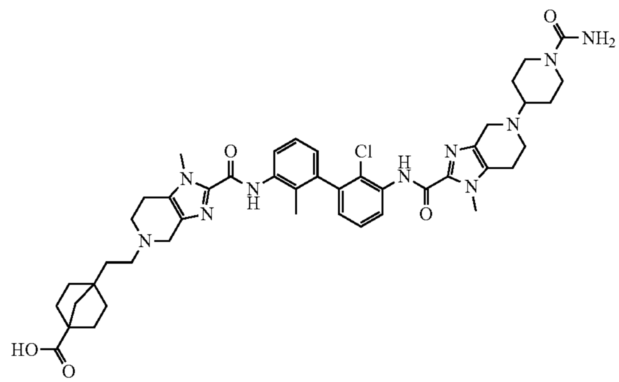 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C2CCN(C(N)=O)CC2)C3)c1Cl] | 851.4 |

Example 41

(R)-4-(2-(2-((2'-chloro-3'-(5-(2-hydroxypropyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

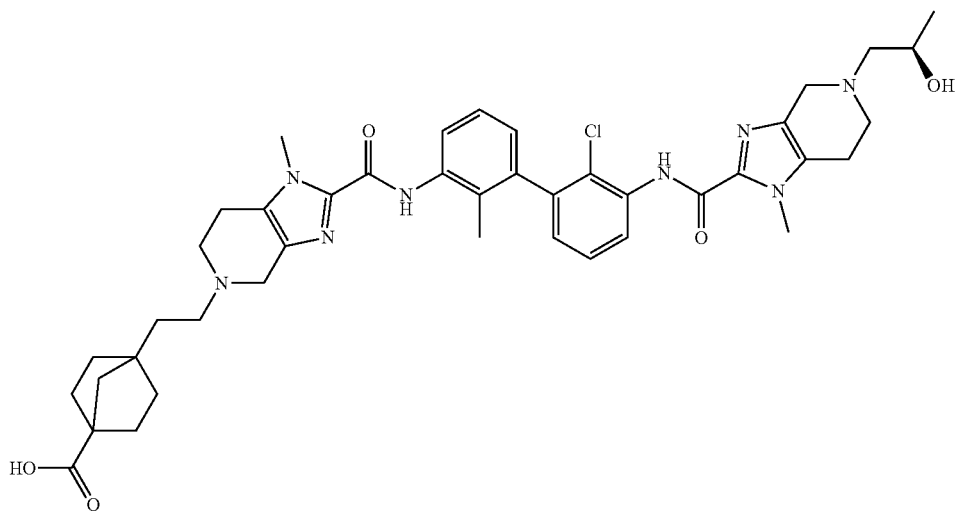 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C[C@@H](C)O)C3)c1Cl]

(R)-2-((Tert-butyldimethylsilyl)oxy)propanal (5.1 mg, 0.027 mmol) was added to a mixture of methyl 4-(2-(2-42'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 37, Step 2: 10 mg, 0.014 mmol), and sodium triacetoxyborohydride (8.6 mg, 0.041 mmol) in dichloromethane (0.20 mL). After being stirred at room temperature for 2 h, the reaction mixture was quenched with saturated aqueous NaHCO₃ solution, and extracted with dichloromethane. The combined organic layers were washed with brine, dried over Na$_2$SO$_4$, filtered, and concentrated under reduced pressure. The residue was dissolved in methanol (0.10 mL), and then treated with HCl in 1,4-dioxane (4.0 M, 67.6 µL, 0.271 mmol) at 40° C. for 2 h. The reaction mixture was concentrated under reduced pressure. The residue was dissolved in THF/MeOH/water (0.1 mL/0.1 mL/0.05 mL), and then treated with lithium hydroxide, monohydrate (5.7 mg, 0.135 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{42}H_{52}ClN_8O_5$ (M+H)+: m/z=783.4; found 783.4.

TABLE 8

The compounds in Table 8 were prepared in accordance with the synthetic protocols set forth in Example 41 using the appropriate starting materials.

| Example # | Name | Structure | LC-MS (M + H)+ |
|---|---|---|---|
| 42 | (S)-4-(2-(2-((2'-chloro-3'-(5-(2-hydroxypropyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 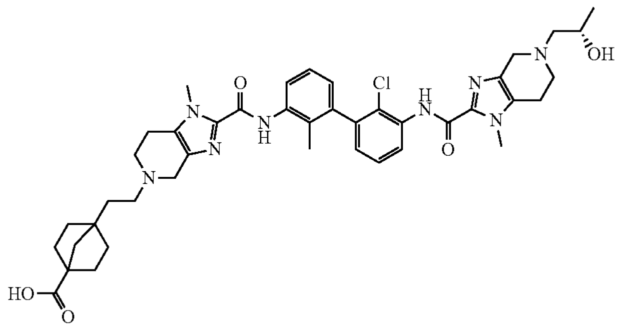 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C[C@H](C)O)C3)c1Cl] | 783.4 |
| 43 | 4-(2-(2-((2'-chloro-3'-(5-(2-hydroxyethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 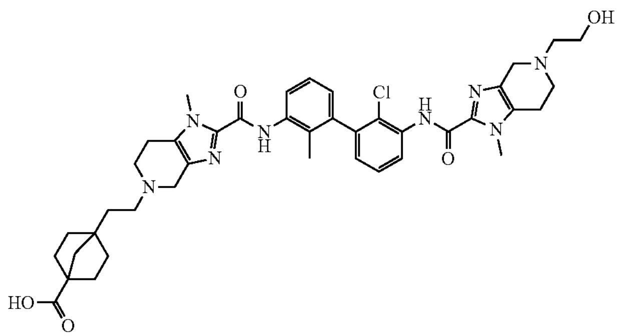 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CCO)C3)c1Cl] | 769.4 |

Example 44

4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid

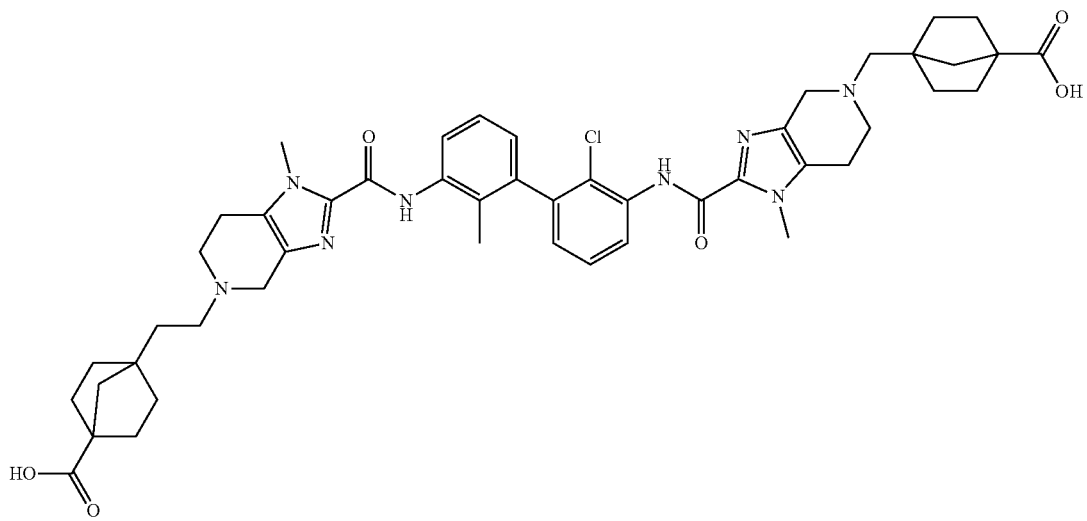 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CC24CCC(C(=O)O)(CC2)C4)C3)c1Cl]

Methyl 4-formylbicyclo[2.2.1]heptane-1-carboxylate (Example 1, Step 6: 4.9 mg, 0.027 mmol) was added to a mixture of methyl 4-(2-(2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 37, Step 2: 10 mg, 0.014 mmol), and sodium triacetoxyborohydride (8.6 mg, 0.041 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in THF/MeOH/water (0.1 mL/0.1 mL/0.05 mL), and then treated with lithium hydroxide, monohydrate (5.7 mg, 0.135 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{48}$H$_{58}$ClN$_8$O$_6$ (M+H)$^+$: m/z=877.4; found 877.4.

TABLE 9

The compounds in Table 9 were prepared in accordance with the synthetic protocols set forth in Example 44 using the appropriate starting materials.

| Example # | Name | Structure | LC-MS (M + H)$^+$ |
|---|---|---|---|
| 45 | 4-(2-(2-((3'-(5-(4-carboxyphenethyl)-1-methyl-4,5,6,7-tetrahydro-1H-imidazo[4,5-c]pyridine-2-carboxamido)-2'-chloro-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 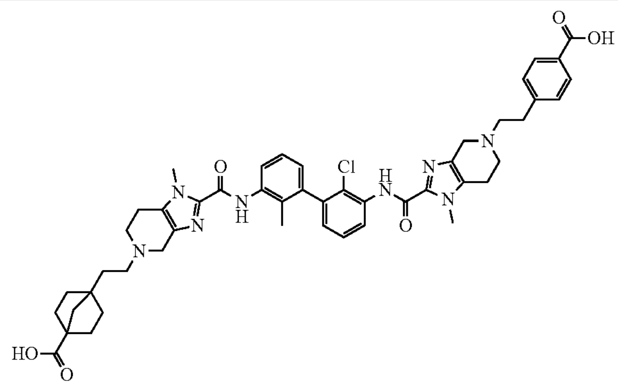 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CCc2ccc(C(=O)O)cc2)C3)c1Cl] | 873.4 |

Example 46

4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

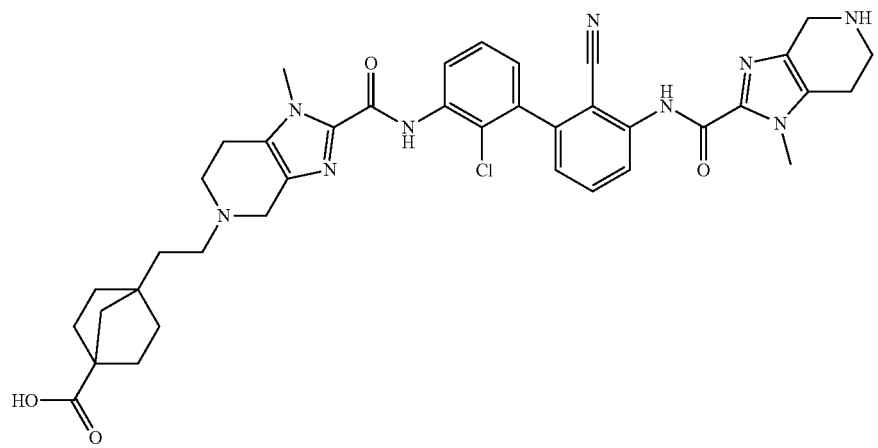 [SMILES: Cn1c(C(=O)Nc2cccc(-c3cccc(NC(=O)c4nc5c(n4C)CCNC5)c3C#N)c2Cl)nc2c1CCN(CCC13CCC(C(=O)O)(CC1)C3)C2]

Step 1: tert-butyl 2-((3-bromo-2-cyanophenyl)carbamoyl)-1-methyl-1,4,6,7-tetrahydro-5H-imidazo[4,5-c]pyridine-5-carboxylate

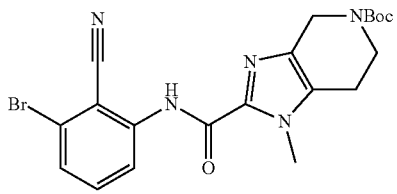 [SMILES: Cn1c(C(=O)Nc2cccc(Br)c2C#N)nc2c1CCN(C(=O)OC(C)(C)C)C2]

Potassium tert-butoxide in THF (1.0 M, 0.677 mL, 0.677 mmol) was added to a solution of 5-tert-butyl 2-methyl 1-methyl-6,7-dihydro-1H-imidazo[4,5-c]pyridine-2,5(4H)-dicarboxylate (Example 1, Step 2: 100 mg, 0.339 mmol) and 2-amino-6-bromobenzonitrile (66.7 mg, 0.339 mmol) in tetrahydrofuran (3.0 mL). After being stirred at room temperature for 30 min, the reaction mixture was quenched with water, and extracted with ethyl acetate. The combined organic layers were washed with brine, dried over $Na_2SO_4$, filtered, and concentrated under reduced pressure. The residue was purified by flash chromatography on a silica gel column eluting with 0-50% ethyl acetate in hexanes to afford the desired product. LC-MS calculated for $C_{20}H_{23}BrN_5O_3$ (M+H)$^+$: m/z=460.1/462.1; found 460.2/462.2.

Step 2: tert-butyl 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

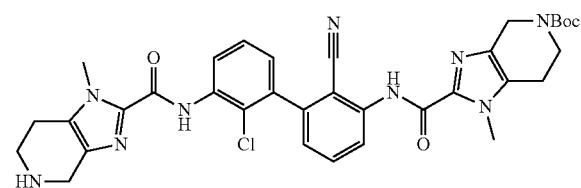 [SMILES: Cn1c(C(=O)Nc2cccc(-c3cccc(NC(=O)c4nc5c(n4C)CCN(C(=O)OC(C)(C)C)C5)c3C#N)c2Cl)nc2c1CCNC2]

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 1, Step 4: 1078 mg, 2.085 mmol) in trifluoroacetic acid (2.0 mL) and dichloromethane (4.0 mL) was stirred at room temperature for 1 h. The reaction mixture was concentrated under reduced pressure. A mixture of the above residue, tert-butyl 2-((3-bromo-2-cyanophenyl)carbamoyl)-1-methyl-1,4,6,7-tetrahydro-5H-imidazo[4,5-c]pyridine-5-carboxylate (Step 1: 800 mg, 1.738 mmol), sodium carbonate (921 mg, 8.69 mmol) and [1,1-bis(dicyclohexylphosphino)ferrocene]dichloropalladium(II) (132 mg, 0.174 mmol) in 1,4-dioxane (12.0 mL) and water (6.0 mL) was purged with nitrogen and then stirred at 110° C. for 3 h. After being cooled to room temperature, the reaction mixture was diluted with water and extracted with dichloromethane. The combined organic layers were dried over $Na_2SO_4$, filtered, and concentrated under reduced pressure. The residue was purified by flash chromatography on a silica gel column eluting with 0-10% methanol in dichloromethane to afford the desired product. LC-MS calculated for $C_{34}H_{37}ClN_9O_4$ (M+H)$^+$: m/z=670.3; found 670.4.

Step 3: methyl 4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-o]pyridin-5-yl)ethyl)bicyclo[2.2.1]heptane-1-carboxylate

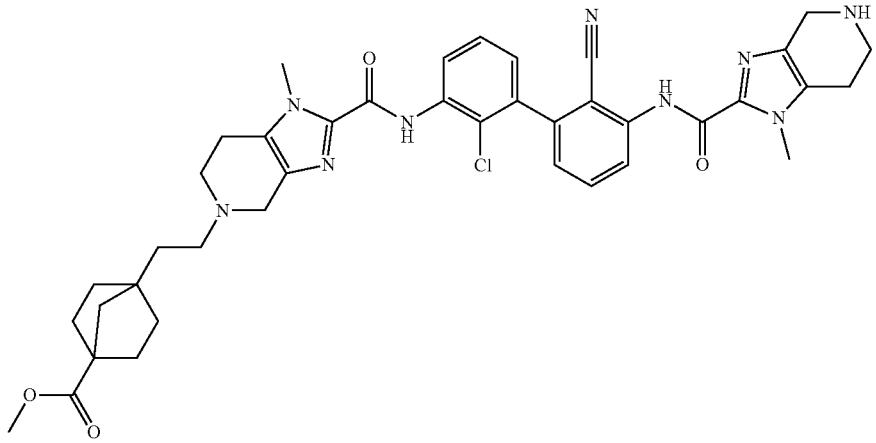 [SMILES: COC(=O)C12CCC(CCN3CCc4c(nc(C(=O)Nc5cccc(-c6cccc(NC(=O)c7nc8c(n7C)CCNC8)c6C#N)c5Cl)n4C)C3)(CC1)C2]

Methyl 4-(2-oxoethyl)bicyclo[2.2.1]heptane-1-carboxylate (Example 1, Step 7: 43.9 mg, 0.224 mmol) was added to a mixture of tert-butyl 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 2: 100 mg, 0.149 mmol), and sodium triacetoxyborohydride (95 mg, 0.458 mmol) in dichloromethane (1.5 mL). After being stirred at room temperature for 2 h, the reaction mixture was quenched with saturated aqueous $NaHCO_3$ solution, and extracted with dichloromethane. The combined organic layers were washed with brine, dried over $Na_2SO_4$, filtered and concentrated under reduced pressure. The residue was treated with dichloromethane (1.0 mL) and trifluoroacetic acid (0.5 mL) at room temperature for 1 h. The mixture was concentrated under reduced pressure. The residue was treated with saturated aqueous $NaHCO_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{40}$H$_{45}$ClN$_9$O$_4$ (M+H)$^+$: m/z=750.3; found 750.3.

Step 4: 4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Lithium hydroxide, monohydrate (2.8 mg, 0.067 mmol) was added to a solution of methyl 4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Step 3: 10 mg, 0.013 mmol) in THF/MeOH/water (0.1 mL/0.1 mL/0.05 mL). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{39}$H$_{43}$ClN$_9$O$_4$ (M+H)$^+$: m/z=736.3; found 736.3.

Example 47

4-(2-(2-((2-chloro-2'-cyano-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

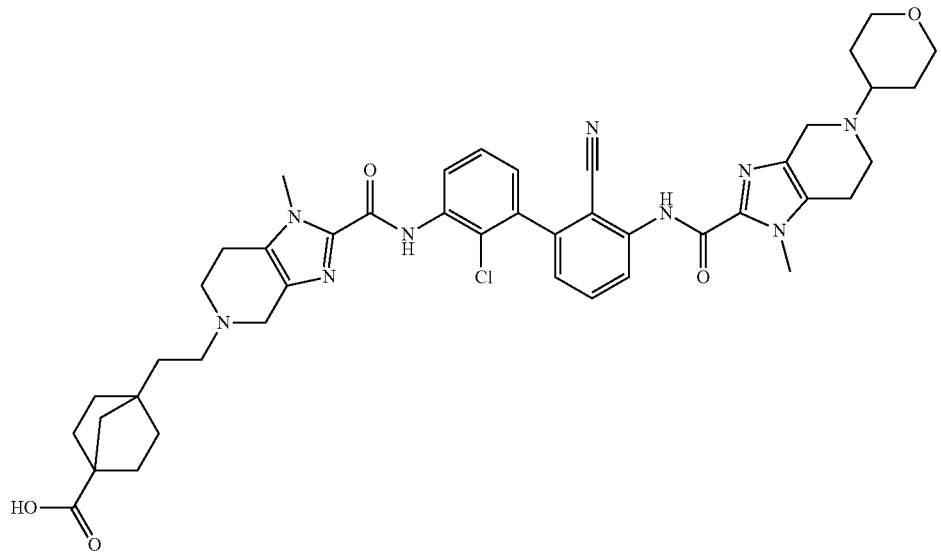 [SMILES: Cn1c(C(=O)Nc2cccc(-c3cccc(NC(=O)c4nc5c(n4C)CCN(C4CCOCC4)C5)c3C#N)c2Cl)nc2c1CCN(CCC13CCC(C(=O)O)(CC1)C3)C2]

Tetrahydro-4H-pyran-4-one (2.7 mg, 0.027 mmol) was added to a mixture of methyl 4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 46, Step 3: 10 mg, 0.013 mmol), and sodium triacetoxyborohydride (8.5 mg, 0.040 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in THF/MeOH/water (0.1 mL/0.1 mL/0.05 mL), and treated with Lithium hydroxide, monohydrate (2.8 mg, 0.067 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{44}$H$_{51}$ClN$_9$O$_5$ (M+H)$^+$: m/z=820.4; found 820.4.

TABLE 10

The compounds in Table 10 were prepared in accordance with the synthetic protocols set forth in Example 47 using the appropriate starting materials.

| Example # | Name | Structure | LC-MS (M + H)+ |
|---|---|---|---|
| 48 | 4-(2-(2-((2-chloro-2'-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 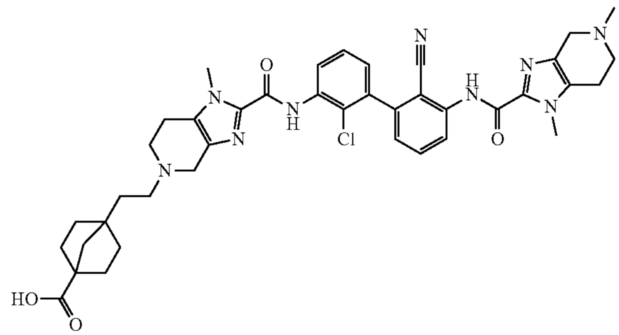 [SMILES: CN1CCc2c(nc(C(=O)Nc3cccc(-c4cccc(NC(=O)c5nc6c(n5C)CCN(CCC57CCC(C(=O)O)(CC5)C7)C6)c4Cl)c3C#N)n2C)C1] | 750.3 |

Example 49

(R)-4-(2-(2-((2-chloro-2'-cyano-3'-(5-(2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

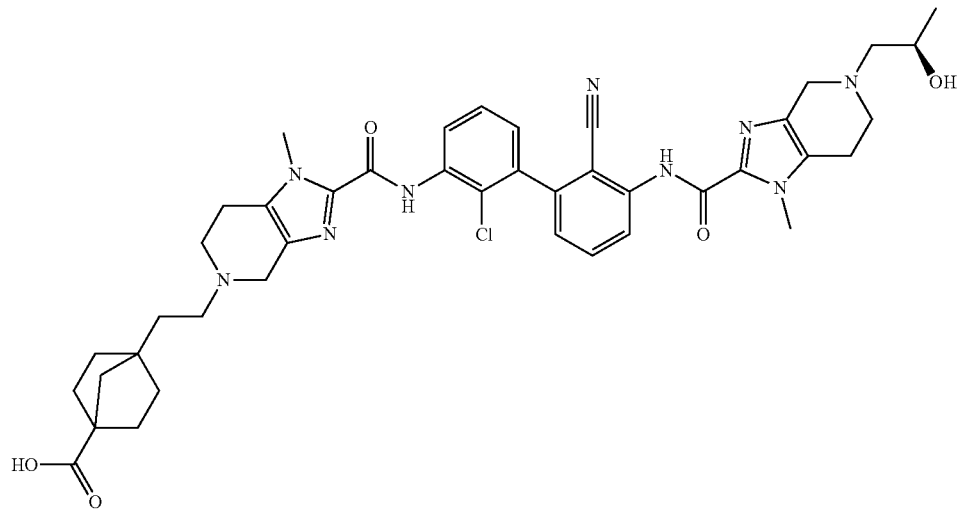 [SMILES: C[C@@H](O)CN1CCc2c(nc(C(=O)Nc3cccc(-c4cccc(NC(=O)c5nc6c(n5C)CCN(CCC57CCC(C(=O)O)(CC5)C7)C6)c4Cl)c3C#N)n2C)C1]

(R)-2-((Tert-butyldimethylsilyl)oxy)propanal (5.0 mg, 0.027 mmol) was added to a mixture of methyl 4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 46, Step 3: 10 mg, 0.013 mmol), and sodium triacetoxyborohydride (8.5 mg, 0.040 mmol) in dichloromethane (0.20 mL). After being stirred at room temperature for 2 h, the reaction mixture was quenched with saturated aqueous $NaHCO_3$ solution, and extracted with dichloromethane. The combined organic layers were washed with brine, dried over $Na_2SO_4$, filtered and concentrated under reduced pressure. The residue was dissolved in methanol (0.10 mL), and then treated with HCl in 1,4-dioxane (4.0 M, 66.6 µL, 0.267 mmol) at 40° C. for 2 h. The reaction mixture was concentrated under reduced pressure. The residue was dissolved in THF/MeOH/water (0.1 mL/0.1 mL/0.05 mL), and then treated with lithium hydroxide, monohydrate (5.6 mg, 0.133 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{42}H_{49}ClN_9O_5(M+H)^+$: m/z=794.4; found 794.4.

TABLE 11

The compounds in Table 11 were prepared in accordance with the synthetic protocols set forth in Example 49 using the appropriate starting materials.

| Example # | Name | Structure | LC-MS (M + H)+ |
|---|---|---|---|
| 50 | 4-(2-(2-(((2-chloro-2'-cyano-3'-(5-(2-hydroxyethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 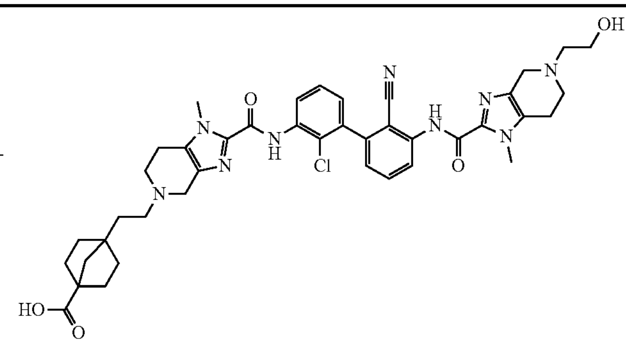 | 780.3 |

Example 51

4,4'-((((((2-chloro-2'-cyano-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid)

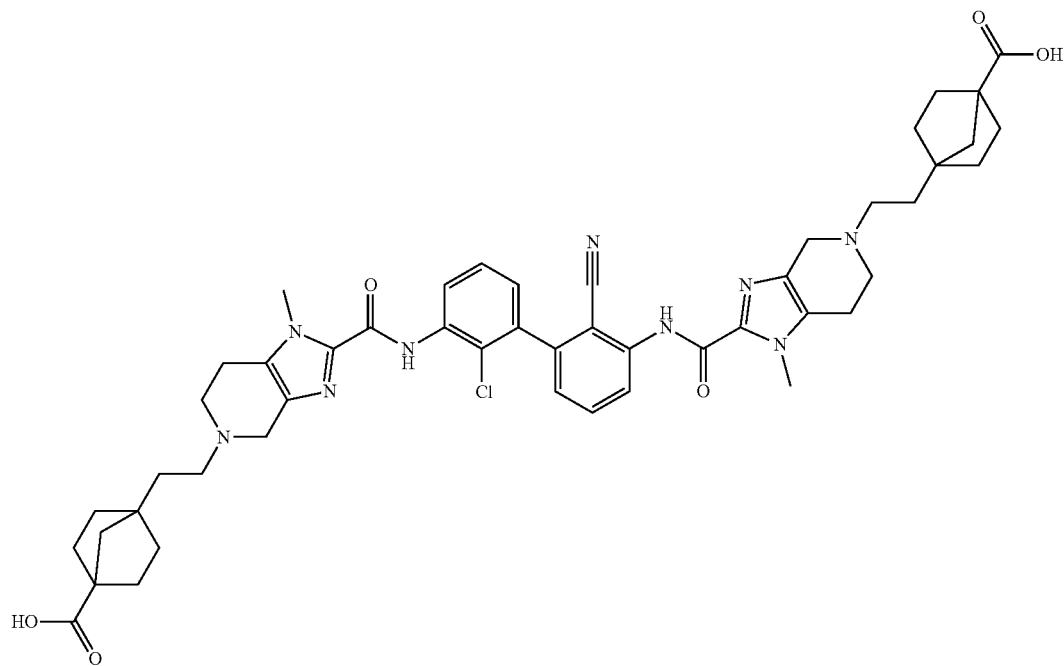 [SMILES: Cn1c(C(=O)Nc2cccc(-c3cccc(NC(=O)c4nc5c(n4C)CCN(CCC46CCC(C(=O)O)(CC4)C6)C5)c3C#N)c2Cl)nc2c1CCN(CCC13CCC(C(=O)O)(CC1)C3)C2]

Methyl 4-(2-oxoethyl)bicyclo[2.2.1]heptane-1-carboxylate (Example 1, Step 7: 5.2 mg, 0.027 mmol) was added to a mixture of methyl 4-(2-(2-(((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 46, Step 3: 10 mg, 0.013 mmol), and sodium triacetoxyborohydride (8.5 mg, 0.040 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in THF/MeOH/water (0.1 mL/0.1 mL/0.05 mL), and then treated with lithium hydroxide, monohydrate (5.6 mg, 0.133 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{49}$H$_{57}$ClN$_9$O$_6$ (M+H)+: m/z=902.4; found 902.5.

TABLE 12

The compounds in Table 12 were prepared in accordance with the synthetic protocols set forth in Example 51 using the appropriate starting materials.

| Example # | Name | Structure | LC-MS (M + H)+ |
|---|---|---|---|
| 52 | 4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2'-chloro-2-cyano-[1,1-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 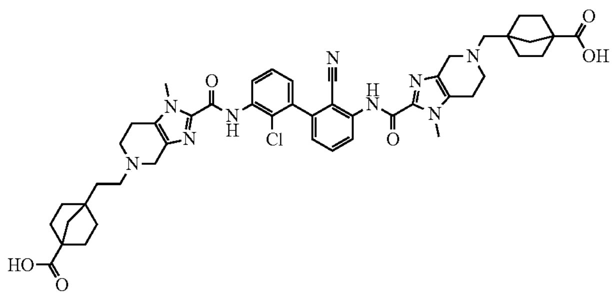 [SMILES: Cn1c(C(=O)Nc2cccc(-c3cccc(NC(=O)c4nc5c(n4C)CCN(CC46CCC(C(=O)O)(CC4)C6)C5)c3C#N)c2Cl)nc2c1CCN(CCC13CCC(C(=O)O)(CC1)C3)C2] | 888.4 |

Example 53

4-(2-(2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

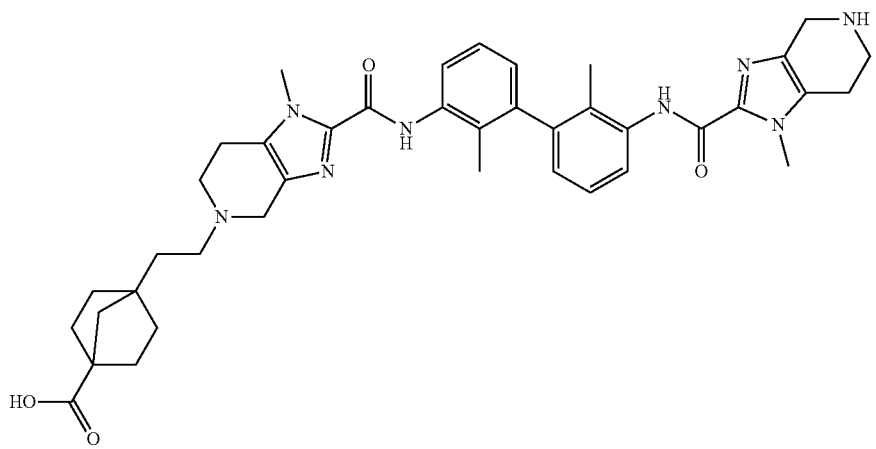 [SMILES: Cc1c(NC(=O)c2nc3c(n2C)CCNC3)cccc1-c1cccc(NC(=O)c2nc3c(n2C)CCN(CCC24CCC(C(=O)O)(CC2)C4)C3)c1C]

Step 1: tert-butyl 2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

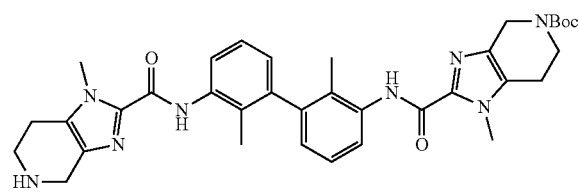 [SMILES: Cc1c(NC(=O)c2nc3c(n2C)CCNC3)cccc1-c1cccc(NC(=O)c2nc3c(n2C)CCN(C(=O)OC(C)(C)C)C3)c1C]

A mixture of tert-butyl 2-((3-bromo-2-methylphenyl)carbamoyl)-1-methyl-1,4,6,7-tetrahydro-5H-imidazo[4,5-c]pyridine-5-carboxylate (Example 27, Step 1: 100 mg, 0.223 mmol) in trifluoroacetic acid (1.0 mL) and dichloromethane (2.0 mL) was stirred at room temperature for 1 h. The reaction mixture was concentrated under reduced pressure. A mixture of the above residue, tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Example 27, Step 2: 133 mg, 0.267 mmol), sodium carbonate (118 mg, 1.113 mmol), and [1,1-bis(di-cyclohexylphosphino)ferrocene]dichloropalladium (II) (16.9 mg, 0.022 mmol) in 1,4-dioxane (1.4 mL) and water (0.7 mL) was purged with nitrogen and then stirred at 110° C. for 2 h. After being cooled to room temperature, the reaction mixture was diluted with water and extracted with dichloromethane. The combined organic layers were dried over $Na_2SO_4$, filtered, and concentrated under reduced pressure. The residue was purified by flash chromatography on a silica gel column eluting with 0-10% methanol in dichloromethane to afford the desired product. LC-MS calculated for $C_{35}H_{43}N_8O_4$ (M+H)+: m/z=639.3; found 639.3.

Step 2: methyl 4-(2-(2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

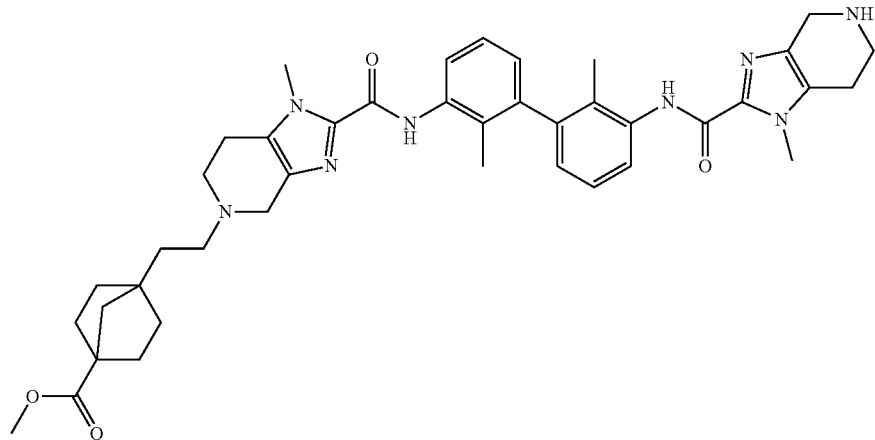 [SMILES: COC(=O)C12CCC(CCN3CCc4c(nc(C(=O)Nc5cccc(-c6cccc(NC(=O)c7nc8c(n7C)CCNC8)c6C)c5C)n4C)C3)(CC1)C2]

Methyl 4-(2-oxoethyl)bicyclo[2.2.1]heptane-1-carboxylate (Example 1, Step 7: 46.1 mg, 0.235 mmol) was added to a mixture of tert-butyl 2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 100 mg, 0.157 mmol) and sodium triacetoxyborohydride (100 mg, 0.470 mmol) in dichloromethane (1.5 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was treated with dichloromethane (1.0 mL) and trifluoroacetic acid (0.5 mL) at room temperature for 1 h. The mixture was concentrated under reduced pressure. The residue was treated with saturated aqueous NaHCO$_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{41}$H$_{51}$N$_8$O$_4$ (M+H)$^+$: m/z=719.4; found 719.4.

Step 3: 4-(2-(2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Lithium hydroxide, monohydrate (2.9 mg, 0.070 mmol) was added to a solution of methyl 4-(2-(2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Step 2: 10 mg, 0.014 mmol) in THF/MeOH/water (0.1 mL/0.1 mL/0.05 mL). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{40}$H$_{49}$N$_8$O$_4$(M+H)$^+$: m/z=705.4; found 705.4.

Example 54

4,4'-(((((2,2'-dimethyl-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid)

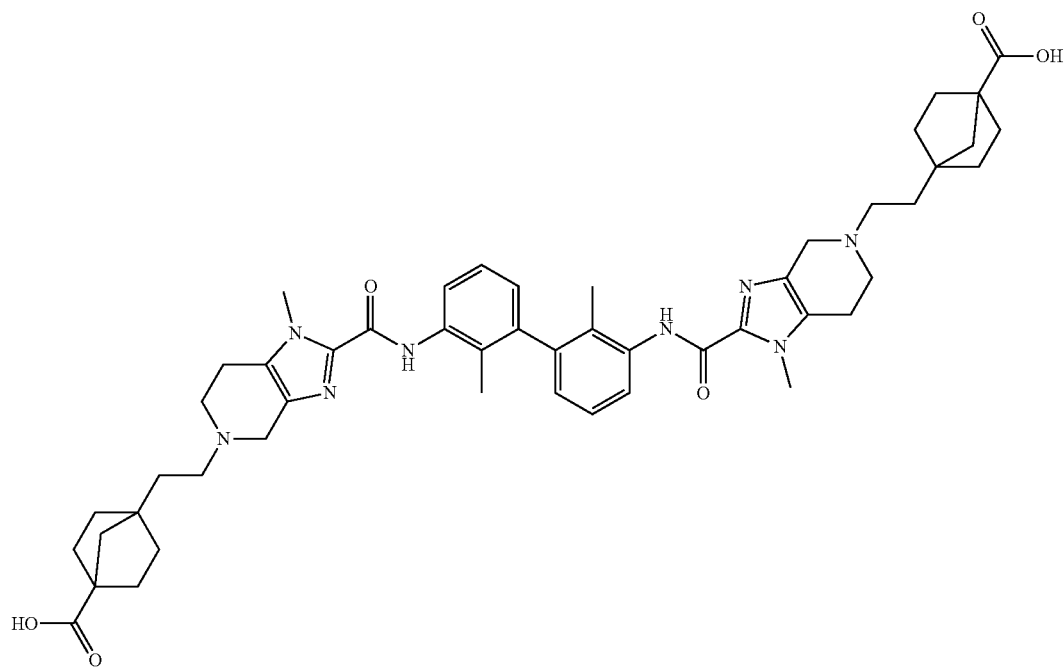 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CCC24CCC(C(=O)O)(CC2)C4)C3)c1C]

Methyl 4-(2-oxoethyl)bicyclo[2.2.1]heptane-1-carboxylate (Example 1, Step 7: 5.5 mg, 0.028 mmol) was added to a mixture of methyl 4-(2-(2-(((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-d]pyridin-5-yl)ethyl)bicyclo[2.2.1]heptane-1-carboxylate (Example 53, Step 2: 10 mg, 0.014 mmol), and sodium triacetoxyborohydride (8.8 mg, 0.042 mmol) in dichloromethane (0.20 mL). After being stirred at room temperature for 2 h, the reaction mixture was quenched with saturated aqueous $NaHCO_3$ solution, and extracted with dichloromethane. The combined organic layers were washed with brine, dried over $Na_2SO_4$, filtered and concentrated under reduced pressure. The residue was dissolved in THF/MeOH/water (0.1 mL/0.1 mL/0.05 mL), and then treated with lithium hydroxide, monohydrate (5.8 mg, 0.139 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{50}H_{63}N_8O_6$ $(M+H)^+$: m/z=871.5; found 871.5.

TABLE 13

The compounds in Table 13 were prepared in accordance with the synthetic protocols set forth in Example 54 using the appropriate starting materials.

| Example # | Name | Structure | LC-MS (M + H)+ |
|---|---|---|---|
| 55 | 4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 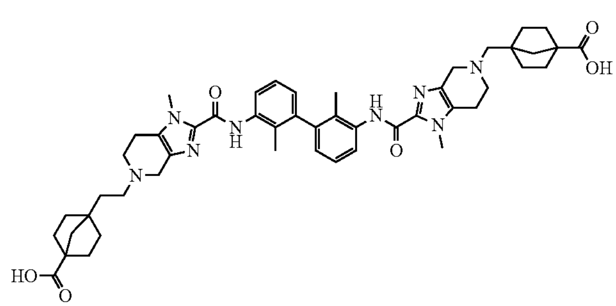 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CC24CCC(C(=O)O)(CC2)C4)C3)c1C] | 857.5 |

TABLE 13-continued

The compounds in Table 13 were prepared in accordance with the synthetic protocols set forth in Example 54 using the appropriate starting materials.

| Example # | Name | Structure | LC-MS (M + H)+ |
|---|---|---|---|
| 56 | 4-(2-(2-((2,2'-dimethyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 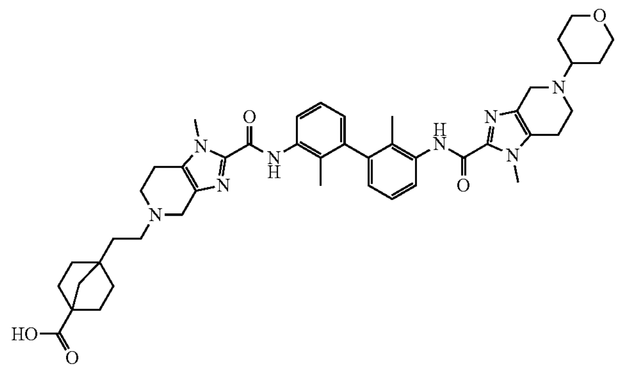 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C2CCOCC2)C3)c1C] | 789.4 |

Example 57

(R)-4-(2-(2-((3'-(5-(2-hydroxypropyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

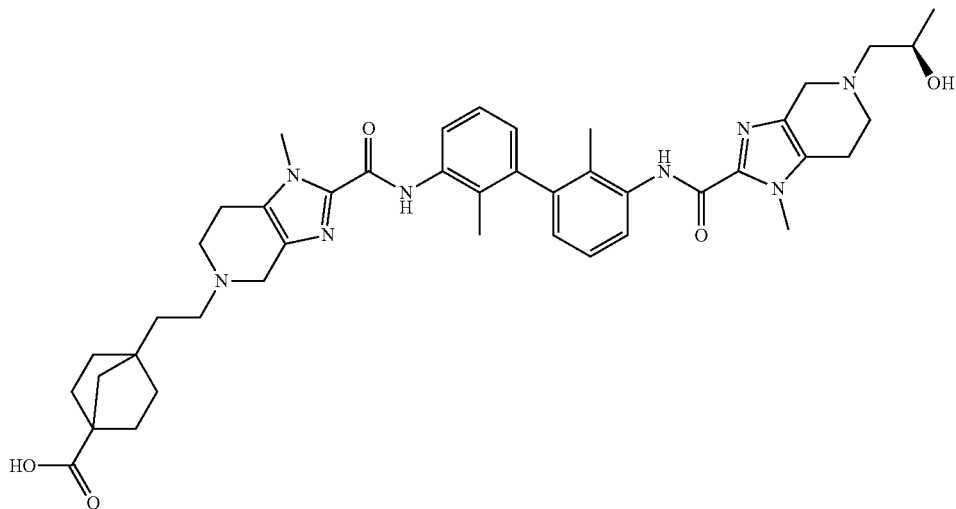 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C[C@@H](C)O)C3)c1C]

(R)-2-((Tert-butyldimethylsilyl)oxy)propanal (5.2 mg, 0.028 mmol) was added to a mixture of methyl 4-(2-(2-((2,2'-dimethyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-d]pyridin-5-yl)ethyl)bicyclo[2.2.1]heptane-1-carboxylate (Example 53, Step 2: 10 mg, 0.014 mmol), and sodium triacetoxyborohydride (8.5 mg, 0.040 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in methanol (0.10 mL), and then treated with HCl in 1,4-dioxane (4.0 M, 69.6 µL, 0.278 mmol) at 40° C. for 2 h. The reaction mixture was concentrated under reduced pressure. The residue was dissolved in THF/MeOH/water (0.1 mL/0.1 mL/0.05 mL), and then treated with lithium hydroxide, monohydrate (5.8 mg, 0.139 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{43}$H$_{55}$N$_8$O$_5$ (M+H)+: m/z=763.4; found 763.4.

TABLE 14

The compounds in Table 14 were prepared in accordance with the synthetic protocols set forth in Example 57 using the appropriate starting materials.

| Example # | Name | Structure | LC-MS (M + H)+ |
|---|---|---|---|
| 58 | (S)-4-(2-(2-((3'-(5-(2-hydroxypropyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 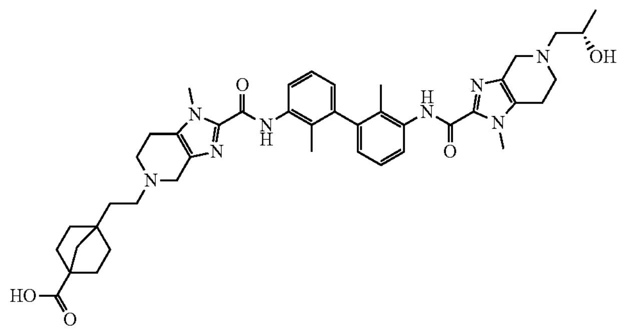 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(C[C@H](C)O)C3)c1C] | 763.4 |
| 59 | 4-(2-(2-((3'-(5-(2-hydroxyethyl)-1-methyl-4,5,6,7-tetrahydro-1H-imidazo[4,5-c]pyridine-2-carboxamido)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 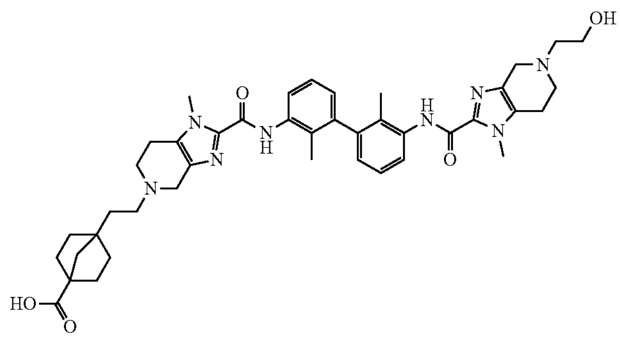 [SMILES: Cc1c(NC(=O)c2nc3c(n2C)CCN(CCO)C3)cccc1-c1cccc(NC(=O)c2nc3c(n2C)CCN(CCC24CCC(C(=O)O)(CC2)C4)C3)c1C] | 749.4 |

Example 60

4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

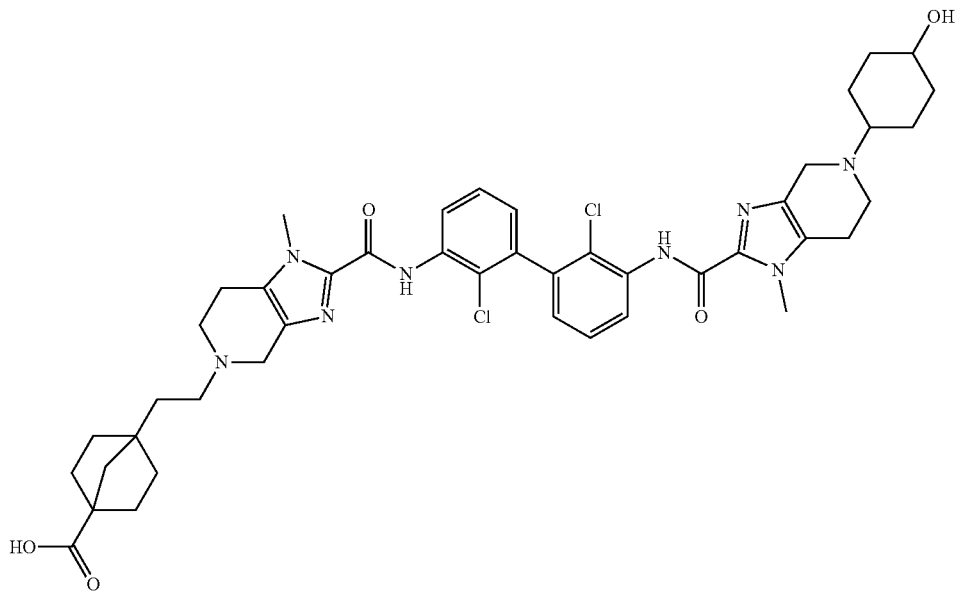 [SMILES: Cn1c(C(=O)Nc2cccc(-c3cccc(NC(=O)c4nc5c(n4C)CCN(C4CCC(O)CC4)C5)c3Cl)c2Cl)nc2c1CCN(CCC13CCC(C(=O)O)(CC1)C3)C2]

Step 1: methyl 4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

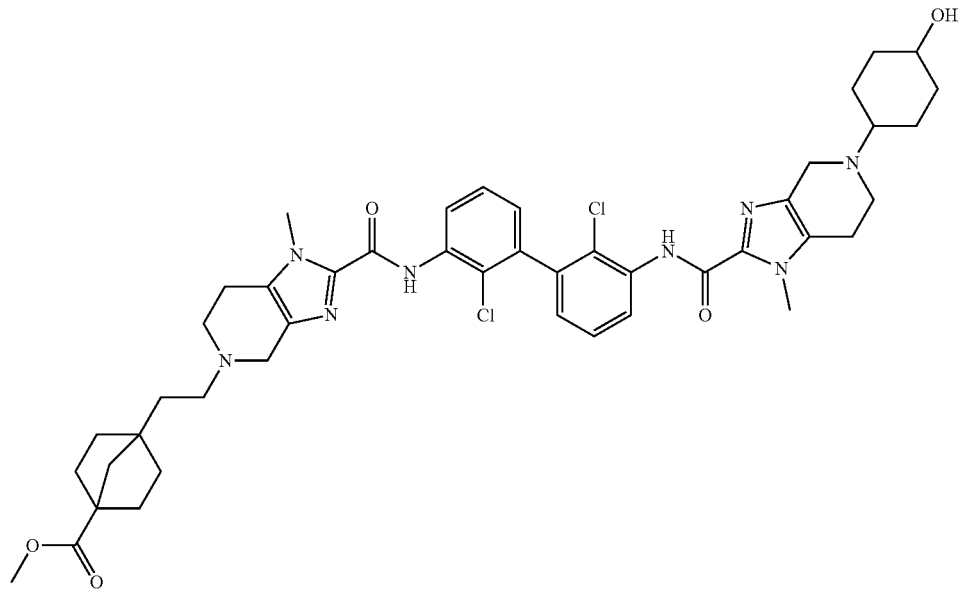 [SMILES: COC(=O)C12CCC(CCN3CCc4c(nc(C(=O)Nc5cccc(-c6cccc(NC(=O)c7nc8c(n7C)CCN(C7CCC(O)CC7)C8)c6Cl)c5Cl)n4C)C3)(CC1)C2]

4-Hydroxycyclohexan-1-one (6.0 mg, 0.053 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl) carbamoyl)-1-methyl-1,4,6,7-tetrahydro-5H-imidazo[4,5-c]pyridin-5-yl)ethyl)bicyclo[2.2.1]heptane-1-carboxylate (Example 1, Step 8: 20 mg, 0.026 mmol), and sodium triacetoxyborohydride (16.7 mg, 0.079 mmol) in dichloromethane (0.30 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was purified by prep-HPLC (pH=10, acetonitrile/water+NH$_4$OH) to give two desired products (cis/trans isomers).

Peak 1: retention time on analytical LC-MS (pH=10, acetonitrile/water+NH$_4$OH) t$_r$=1.71 min, LC-MS calculated for C$_{45}$H$_{55}$Cl$_2$N$_8$O$_5$ (M+H)$^+$: m/z=857.4; Found: 857.4.

Peak 2: retention time on analytical LC-MS (pH=10, acetonitrile/water+NH$_4$OH) t$_r$=1.73 min, LC-MS calculated for C$_{45}$H$_{55}$Cl$_2$N$_8$O$_5$ (M+H)$^+$: m/z=857.4; Found: 857.4;

Step 2: 4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Methyl 4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (5 mg, 5.83 μmol) from Step 1, peak 1 and peak 2 were respectively treated with lithium hydroxide, monohydrate (1.3 mg, 0.030 mmol) in THF/MeOH/water (0.1 mL/0.1 mL/0.05 mL) at 30° C. for 2 h. The reactions were purified by prep-HPLC (pH=2, acetonitrile/water+TFA) to give the desired products as the TFA salt.

Compound 1 (from Step 1, peak 1): LC-MS calculated for C$_{44}$H$_{53}$Cl$_2$N$_8$O$_5$ (M+H)$^+$: m/z=843.4; found: 843.4.

Compound 2 (from Step 1, peak 2): LC-MS calculated for C$_{44}$H$_{53}$Cl$_2$N$_8$O$_5$ (M+H)$^+$: m/z=843.4; found: 843.4.

Example 61

4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

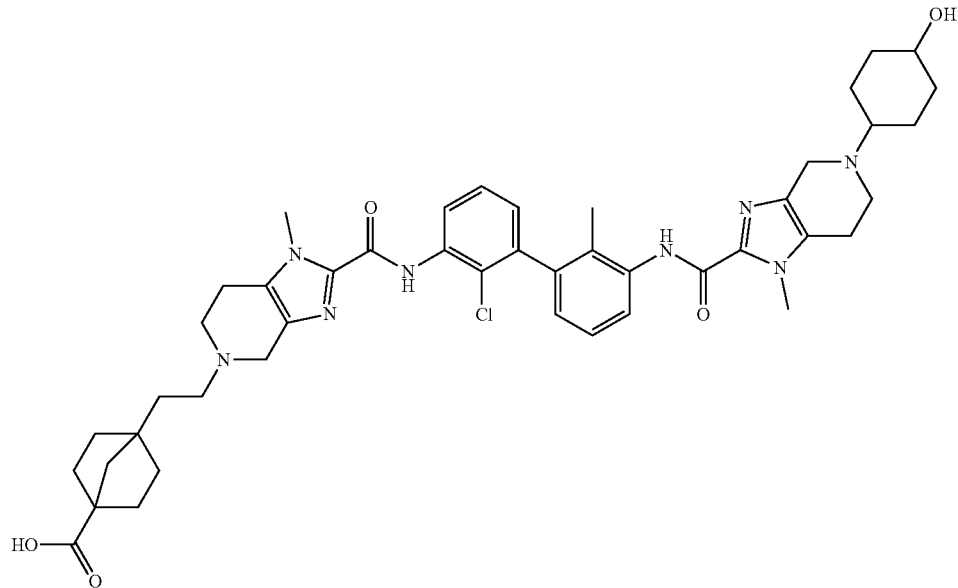 [SMILES: Cc1c(NC(=O)c2nc3c(n2C)CCN(C2CCC(O)CC2)C3)cccc1-c1cccc(NC(=O)c2nc3c(n2C)CCN(CCC24CCC(C(=O)O)(CC2)C4)C3)c1Cl]

Step 1: methyl 4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

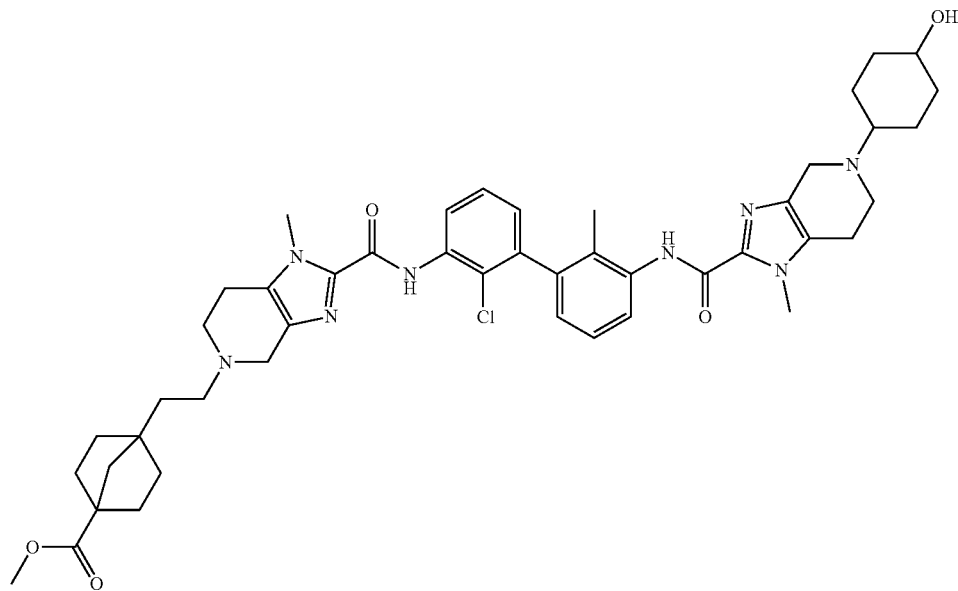 [SMILES: COC(=O)C12CCC(CCN3CCc4c(nc(C(=O)Nc5cccc(-c6cccc(NC(=O)c7nc8c(n7C)CCN(C7CCC(O)CC7)C8)c6C)c5Cl)n4C)C3)(CC1)C2]

4-Hydroxycyclohexan-1-one (6.2 mg, 0.054 mmol) was added to a mixture of methyl 4-(2-(2-((2-chloro-T-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylate (Example 27, Step 4: 20 mg, 0.027 mmol), and sodium triacetoxyborohydride (17.2 mg, 0.081 mmol) in dichloromethane (0.30 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was purified by prep-HPLC (pH=10, acetonitrile/water+NH$_4$OH) to give two desired products (cis/trans isomers).

Peak 1: retention time on analytical LC-MS (pH=10, acetonitrile/water+NH$_4$OH) t$_r$=1.62 min, LC-MS calculated for C$_{46}$H$_{58}$ClN$_8$O$_5$ (M+H)$^+$: m/z=837.4; Found: 837.4.

Peak 2: retention time on analytical LC-MS (pH=10, acetonitrile/water+NH$_4$OH) t$_r$=1.64 min, LC-MS calculated for C$_{46}$H$_{58}$ClN$_8$O$_5$ (M+H)$^+$: m/z=837.4; Found: 837.4.

Step 2: 4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Methyl 4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl) ethyl)bicyclo[2.2.1]heptane-1-carboxylate (5 mg, 5.97 µmol) from Step 1, peak 1 and peak 2 were respectively treated with lithium hydroxide, monohydrate (1.3 mg, 0.030 mmol) in THF/MeOH/water (0.1 mL/0.1 mL/0.05 mL) at 30° C. for 2 h. The reactions were purified by prep-HPLC (pH=2, acetonitrile/water+TFA) to give the desired products as the TFA salt.

Compound 1 (from Step 1, peak 1): LC-MS calculated for C$_{45}$H$_{56}$ClN$_8$O$_5$ (M+H)$^+$: m/z=823.4; found: 823.4.

Compound 2 (from Step 1, peak 2): LC-MS calculated for C$_{45}$H$_{56}$ClN$_8$O$_5$ (M+H)$^+$: m/z=823.4; found: 823.4.

Example 62

4-(2-(2-03'45-(2-(trans-4-carboxycyclohexyl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

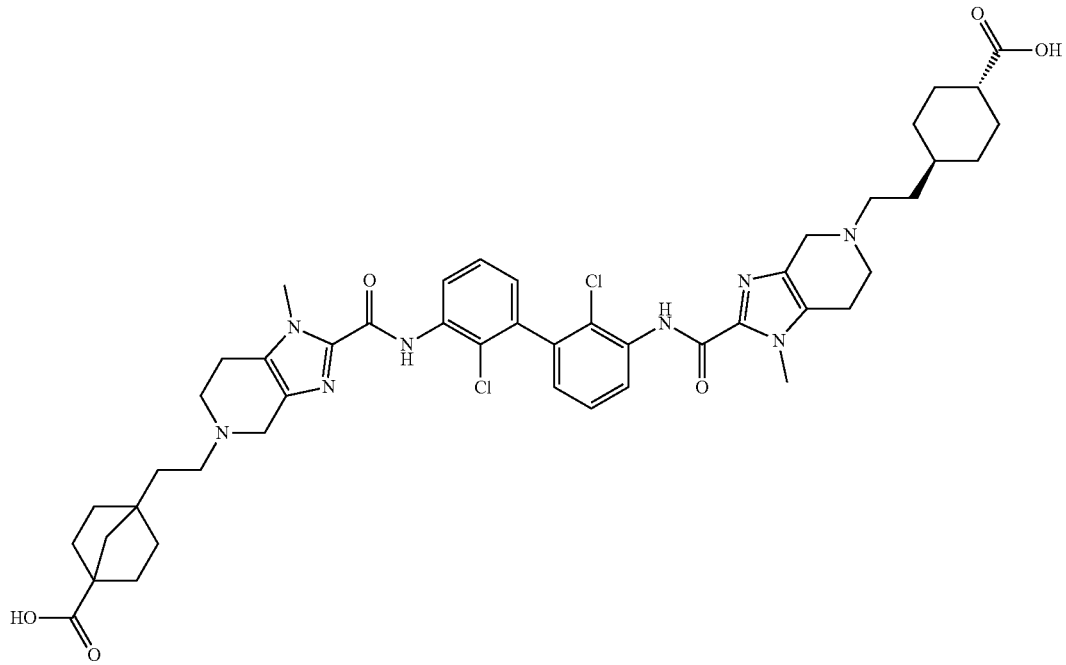 [SMILES: Cn1c(C(=O)Nc2cccc(-c3cccc(NC(=O)c4nc5c(n4C)CCN(CC[C@H]4CC[C@H](C(=O)O)CC4)C5)c3Cl)c2Cl)nc2c1CCN(CCC13CCC(C(=O)O)(CC1)C3)C2]

Methyl 4-(2-oxoethyl)cyclohexane-1-carboxylate (4.9 mg, 0.026 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 1, Step 8: 10 mg, 0.013 mmol), and sodium triacetoxyborohydride (8.4 mg, 0.039 mmol) in dichloromethane (0.2 mL). After being stirred at room temperature for 2 h, the reaction mixture was quenched with saturated aqueous NaHCO$_3$ solution, and extracted with dichloromethane. The combined organic layers were dried over Na$_2$SO$_4$, filtered and concentrated under reduced pressure. The residue was dissolved in THF/MeOH/water (0.1 mL/0.1 mL/0.05 mL), and treated with lithium hydroxide, monohydrate (5.5 mg, 0.132 mmol). After being stirred at 30° C. for 3 h, the reaction mixture was diluted with methanol, and purified by prep-HPLC (pH=2, acetonitrile/water+TFA) to give the desired product (major peak) as the TFA salt. LC-MS calculated for C$_{47}$H$_{57}$Cl$_2$N$_8$O$_6$ (M+H)$^+$: m/z=899.4; found 899.4.

Example 63

4-(2-(2-03'45-(4-carboxybutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

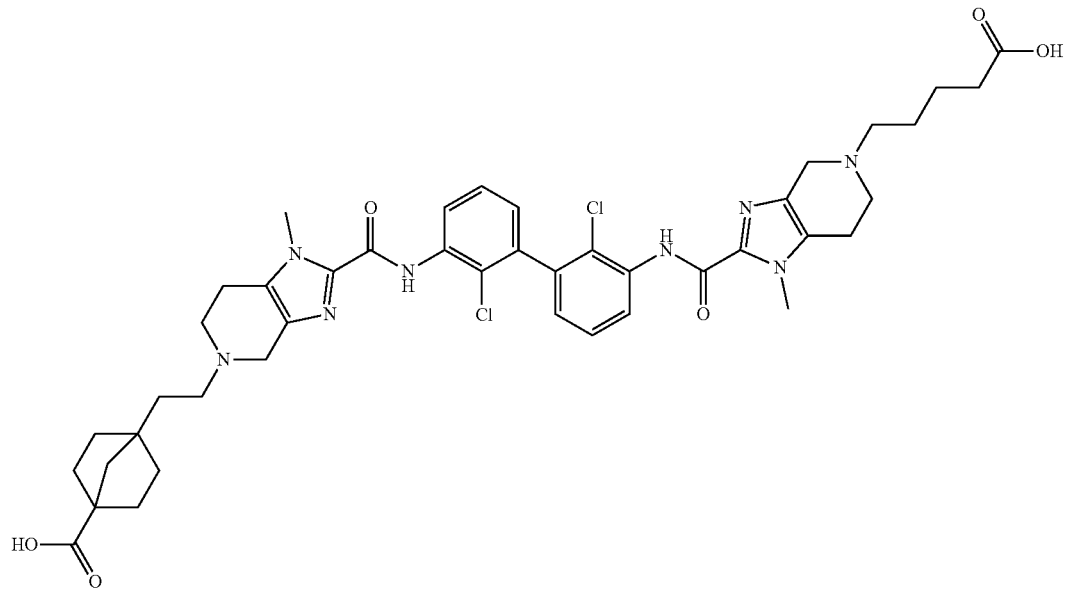 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCCCC(=O)O)C2]

Step 1: methyl 4-(2-(2-((3'-(5-(5-(tert-butoxy)-5-oxopentyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

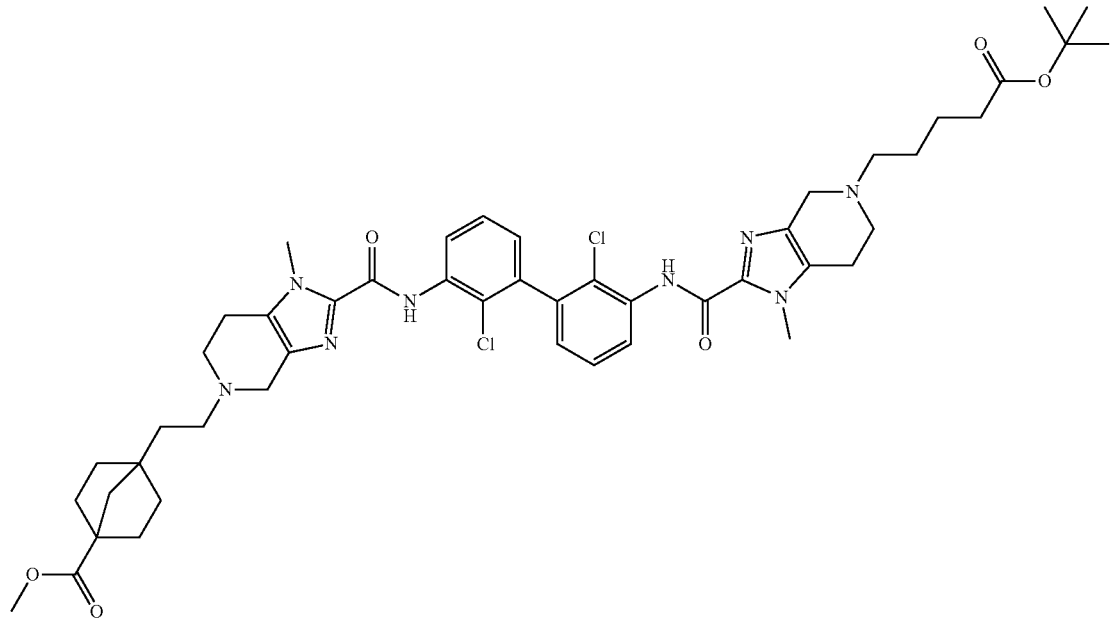 [SMILES: COC(=O)C12CCC(CCN3CCc4c(nc(C(=O)Nc5cccc(-c6cccc(NC(=O)c7nc8c(n7C)CCN(CCCCC(=O)OC(C)(C)C)C8)c6Cl)c5Cl)n4C)C3)(CC1)C2]

Tert-butyl 5-oxopentanoate (34.0 mg, 0.197 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl) carbamoyl)-1-methyl-1,4,6,7-tetrahydro-5H-imidazo[4,5-c]pyridin-5-yl)ethyl)bicyclo[2.2.1]heptane-1-carboxylate (Example 1, Step 8: 100 mg, 0.132 mmol), and sodium triacetoxyborohydride (84 mg, 0.395 mmol) in dichloromethane (1.2 mL). After being stirred at room temperature for 2 h, the reaction mixture was quenched with saturated aqueous $NaHCO_3$ solution, and extracted with dichloromethane. The combined organic layers were dried over $Na_2SO_4$, filtered and concentrated under reduced pressure. The residue was purified by flash chromatography on a silica gel column eluting with 0-10% methanol in dichloromethane to afford the desired product. LC-MS calculated for $C_{48}H_{61}Cl_2N_8O_6$ $(M+H)^+$: m/z=915.4; found 915.5.

Step 2: 4-(2-(2-((3'-(5-(4-carboxybutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid A solution of methyl 4-(2-(2-((3'-(5-(5-(tert-butoxy)-5-oxopentyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Step 1: 10 mg, 10.9 μmop in tetrahydrofuran (0.15 mL) was treated with HCl in 1,4-dioxane (4.0 M, 27.3 μL, 0.109 mmol) at 40° C. for 1 h. The reaction mixture was concentrated under reduced pressure. The residue was dissolved in THF/MeOH/water (0.1 mL/0.1 mL/0.05 mL), and treated with lithium hydroxide, monohydrate (4.6 mg, 0.109 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for $C_{43}H_{51}Cl_2N_8O_6$ $(M+H)^+$: m/z=845.3; found 845.3.

Example 64

4-(2-(2-((2,2'-dichloro-3'-(5-(5-(dimethylamino)-5-oxopentyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

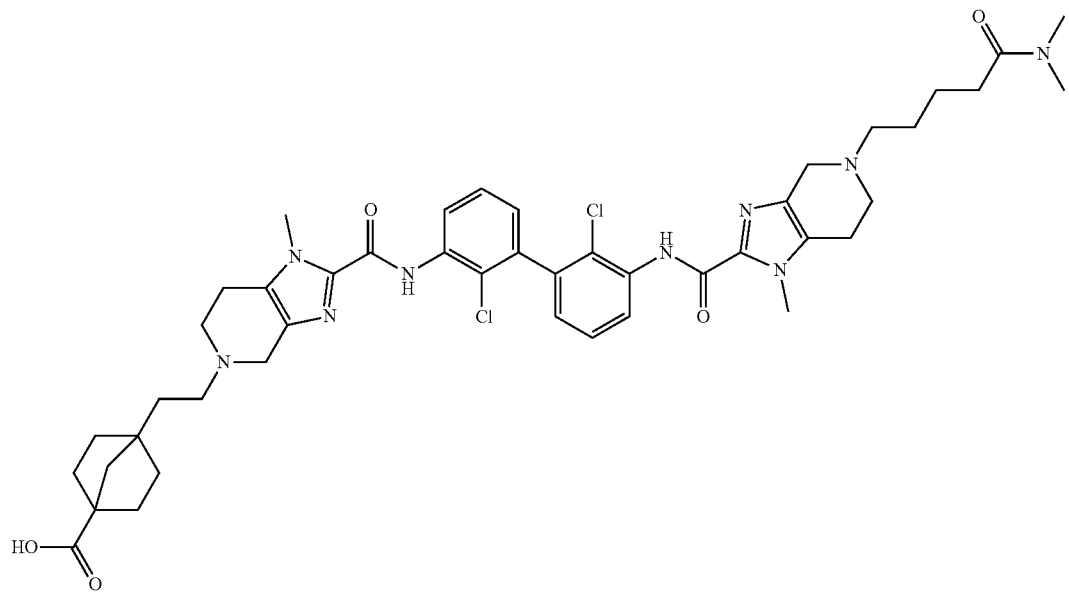 [SMILES: CN(C)C(=O)CCCCN1CCc2c(nc(C(=O)Nc3cccc(-c4cccc(NC(=O)c5nc6c(n5C)CCN(CCC57CCC(C(=O)O)(CC5)C7)C6)c4Cl)c3Cl)n2C)C1]

A solution of methyl 4-(2-(2-43'-(5-(5-(tert-butoxy)-5-oxopentyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Example 63, Step 1: 10 mg, 10.9 μmol) in tetrahydrofuran (0.15 mL) was treated with HCl in 1,4-dioxane (4.0 M, 27.3 μL, 0.109 mmol) at 40° C. for 1 h. The reaction mixture was concentrated under reduced pressure. The residue was dissolved in DMF (0.15 mL), and then subsequently treated with N,N-diisopropylethylamine (9.5 μL, 0.055 mmol), 1-[bis(dimethylamino)methylene]-1H-1,2,3-triazolo[4,5-b]pyridinium 3-oxide hexafluorophosphate (8.3 mg, 0.022 mmol), and dimethylamine hydrochloride (1.4 mg, 0.016 mmol). After being stirred at room temperature for 2 h, lithium hydroxide, monohydrate (4.6 mg, 0.109 mmol) was added. The reaction mixture was stirred at 30° C. for 3 h, then diluted with methanol, and purified by pH 2 preparative LC/MS (MeCN/water with TFA) to give the desired product. LC-MS calculated for $C_{45}H_{56}Cl_2N_9O_5$ (M+H)$^+$: m/z=872.4; found 872.4.

Example 65

4-(2-(2-((3'-(5-(cis-4-carboxy-4-methylcyclohexyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

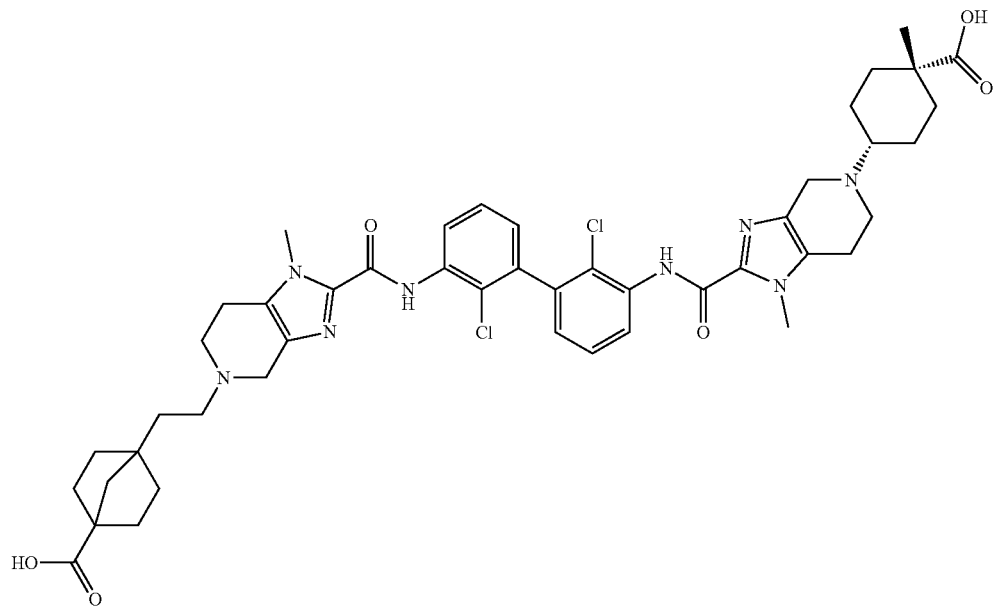 [SMILES: Cn1c(C(=O)Nc2cccc(-c3cccc(NC(=O)c4nc5c(n4C)CCN([C@H]4CC[C@@](C)(C(=O)O)CC4)C5)c3Cl)c2Cl)nc2c1CCN(CCC13CCC(C(=O)O)(CC1)C3)C2]

Step 1: methyl 5-(cis-4-(tert-butoxycarbonyl)-4-methylcyclohexyl)-1-methyl-4,5,6,7-tetrahydro-1H-imidazo[4,5-c]pyridine-2-carboxylate and methyl 5-(trans-4-(tert-butoxycarbonyl)-4-methylcyclohexyl)-1-methyl-4,5,6,7-tetrahydro-1H-imidazo[4,5-c]pyridine-2-carboxylate

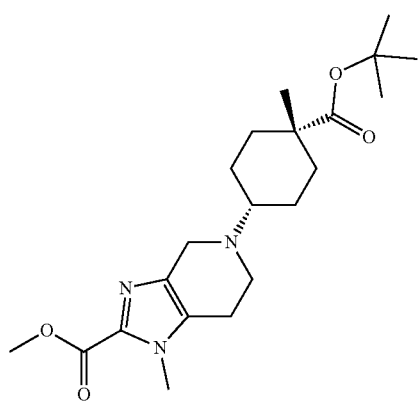

and

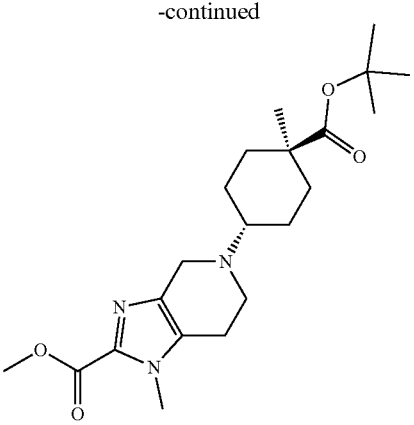

-continued

A solution of 5-tert-butyl 2-methyl 1-methyl-6,7-dihydro-1H-imidazo[4,5-c]pyridine-2,5(4H)-dicarboxylate (Example 1, Step 2: 0.50 g, 1.693 mmol) in dichloromethane (5.0 mL) and trifluoroacetic acid (5.0 mL) was stirred at room temperature for 1 h. The mixture was concentrated under reduced pressure. The residue was dissolved in dichloromethane (10.0 mL) and sequentially treated with N,N-diisopropylethylamine (0.89 mL, 5.08 mmol), sodium triacetoxyborohydride (0.72 g, 3.39 mmol) and tert-butyl 1-methyl-4-oxocyclohexane-1-carboxylate (1.1 g, 4.66 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford a mixture of cis/trans isomers, which was separated by a preparative chiral column (Phenomenex LUX Sum Cellulose-4) eluting with 10% EtOH in hexanes to give the desired products.

Peak 1 (cis): retention time $t_r$=20.1 min, LC-MS calculated for $C_{21}H_{34}N_3O_4(M+H)^+$: m/z=392.3; Found: 392.2. $^1$H NMR (500 MHz, CDCl$_3$) δ 3.92 (s, 3H), 3.85 (s, 3H), 3.66 (s, 2H), 2.91 (t, J=5.5 Hz, 2H), 2.66 (t, J=5.5 Hz, 2H), 2.62-2.52 (m, 1H), 2.28-2.20 (m, 2H), 1.86-1.77 (m, 2H), 1.52-1.42 (m, 11H), 1.21-1.14 (m, 2H), 1.13 (s, 3H).

Peak 2 (trans): retention time $t_r$=24.3 min, LC-MS calculated for $C_{21}H_{34}N_3O_4$ (M+H)$^+$: m/z=392.3; Found: 392.2. $^1$H NMR (500 MHz, CDCl$_3$) δ 3.92 (s, 3H), 3.86 (s, 3H), 3.68 (s, 2H), 2.94 (t, J=5.7 Hz, 2H), 2.67 (t, J=5.7 Hz, 2H), 2.50 (tt, J=10.6, 3.5 Hz, 1H), 1.83-1.76 (m, 2H), 1.75-1.69 (m, 4H), 1.64-1.52 (m, 2H), 1.45 (s, 9H), 1.18 (s, 3H).

Step 2: tert-butyl cis-4-(2-((3-bromo-2-chlorophenyl)carbamoyl)-1-methyl-1,4,6,7-tetrahydro-5H-imidazo[4,5-c]pyridin-5-yl)-1-methylcyclohexane-1-carboxylate Potassium tert-butoxide in THF (1.0 M, 0.56 mL, 0.56 mmol) was added to a solution of methyl 5-(cis-4-(tert-butoxycarbonyl)-4-methylcyclohexyl)-1-methyl-4,5,6,7-tetrahydro-1H-imidazo[4,5-c]pyridine-2-carboxylate (Step1, Peak 1: 110 mg, 0.281 mmol) and 3-bromo-2-chloroaniline (58.0 mg, 0.281 mmol) in tetrahydrofuran (1.5 mL). After being stirred at room temperature for 30 min, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 0-50% ethyl acetate in hexanes to afford the desired product. LC-MS calculated for $C_{26}H_{35}BrClN_4O_3$ (M+H)$^+$: m/z=565.2/567.2; found 565.2/567.2.

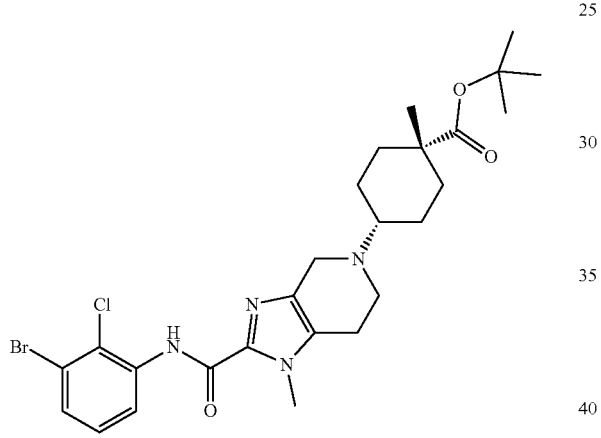

Step 3: tert-butyl cis-4-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-o]pyridin-5-yl)-1-methylcyclohexane-1-carboxylate

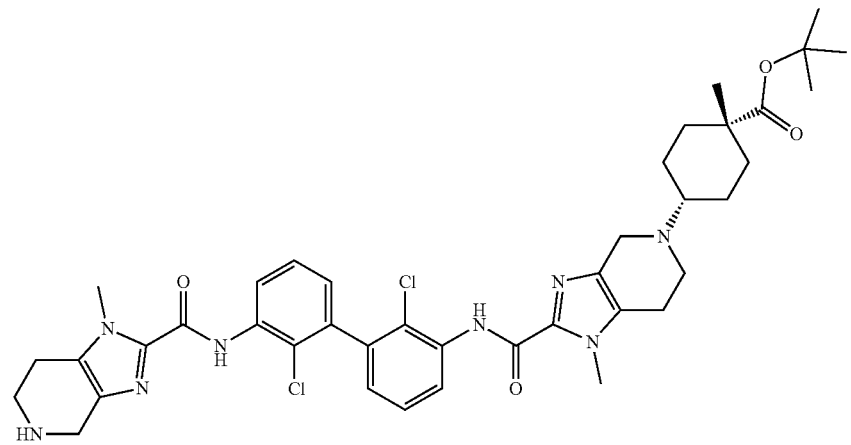 [SMILES: Cn1c(C(=O)Nc2cccc(-c3cccc(NC(=O)c4nc5c(n4C)CCN([C@H]4CC[C@@](C)(C(=O)OC(C)(C)C)CC4)C5)c3Cl)c2Cl)nc2c1CCNC2]

A solution of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-d]pyridine-5-carboxylate (Example 1, Step 4: 164 mg, 0.318 mmol) in trifluoroacetic acid (0.5 mL) and dichloromethane (1.0 mL) was stirred at room temperature for 1 h. The reaction mixture was concentrated under reduced pressure. A mixture of the above residue, tert-butyl cis-4-(2-((3-bromo-2-chlorophenyl)carbamoyl)-1-methyl-1,4,6,7-tetrahydro-5H-imidazo[4,5-c]pyridin-5-yl)-1-methylcyclohexane-1-carboxylate (Step 2: 150 mg, 0.265 mmol), sodium carbonate (140 mg, 1.325 mmol) and [dichloro[1,1'-bis(diphenylphosphino)ferrocene] palladium (II) dichloromethane adduct (21.6 mg, 0.027 mmol) in 1,4-dioxane (1.6 mL) and water (0.8 mL) was purged with nitrogen and then stirred at 110° C. for 2 h. After being cooled to room temperature, the reaction mixture was diluted with water and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{40}$H$_{49}$Cl$_2$N$_8$O$_4$ (M+H)$^+$: m/z=775.3; found 775.4.

Step 4: 4-(2-(2-((3'-(5-(cis-4-carboxy-4-methylcyclohexyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid Methyl 4-(2-oxoethyl)bicyclo[2.2.1]heptane-1-carboxylate (Example 1, Step 7: 3.8 mg, 0.019 mmol) was added to a mixture of tert-butyl cis-4-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate (Step 3: 10 mg, 0.013 mmol) and sodium triacetoxyborohydride (8.2 mg, 0.039 mmol) in dichloromethane (0.20 mL). After being stirred at room temperature for 2 h, the reaction mixture was quenched with saturated aqueous NaHCO$_3$ solution, and extracted with dichloromethane. The combined organic layers were dried over Na$_2$SO$_4$, filtered and concentrated under reduced pressure. The residue was dissolved in methanol (0.10 mL), and then treated with HCl in 1,4-dioxane (4.0 M, 32 µL, 0.129 mmol) at 40° C. for 1 h. The reaction mixture was concentrated under reduced pressure. The residue was dissolved in THF/MeOH/water (0.1 mL/0.1 mL/0.05 mL), and then treated with lithium hydroxide, monohydrate (5.4 mg, 0.129 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{46}$H$_{55}$Cl$_2$N$_8$O$_6$ (M+H)$^+$: m/z=885.4; found 885.4.

Example 66

4-(2-(2-((3'-(5-(trans-4-carboxy-4-methylcyclohexyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

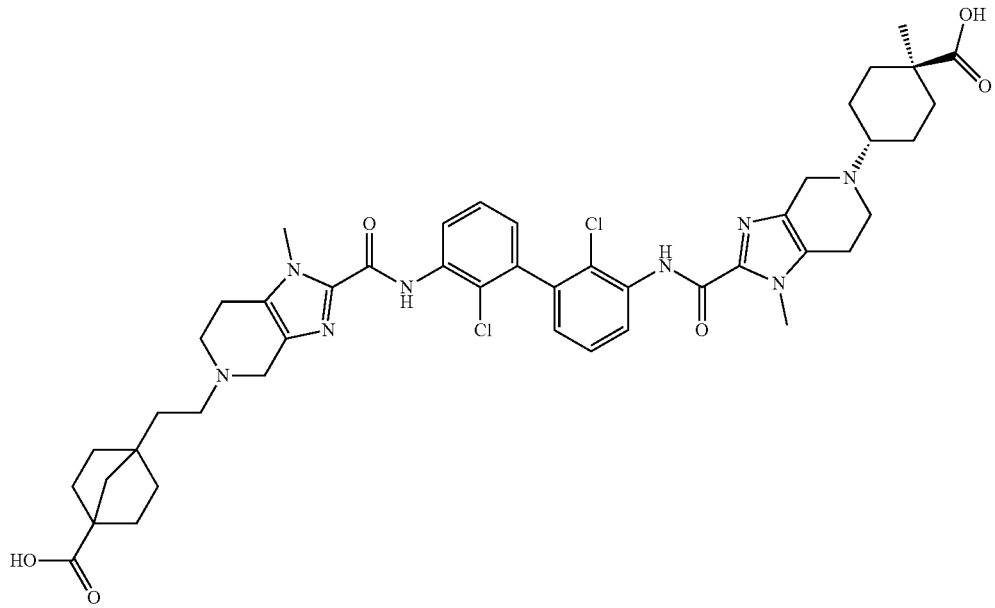 [SMILES: Cn1c(C(=O)Nc2cccc(-c3cccc(NC(=O)c4nc5c(n4C)CCN([C@H]4CC[C@](C)(C(=O)O)CC4)C5)c3Cl)c2Cl)nc2c1CCN(CCC13CCC(C(=O)O)(CC1)C3)C2]

This compound was prepared using similar procedures as described for Example 65 with methyl 5-(trans-4-(tert-butoxycarbonyl)-4-methylcyclohexyl)-1-methyl-4,5,6,7-tetrahydro-1H-imidazo[4,5-c]pyridine-2-carboxylate (from Example 65, Step1, Peak 2) replacing methyl 5-(cis-4-(tert-butoxycarbonyl)-4-methylcyclohexyl)-1-methyl-4,5,6,7-tetrahydro-1H-imidazo[4,5-c]pyridine-2-carboxylate in Step 2.

The reaction mixture was diluted with methanol, and then purified by purified by pH 2 preparative LC/MS (MeCN/water with TFA) to give the desired product as the TFA salt. LC-MS calculated for $C_{46}H_{55}Cl_2N_8O_6$ $(M+H)^+$: m/z=885.4; found 885.4.

Example A. Homogeneous Time-Resolved Fluorescence (HTRF) PD-1/PD-L1 Binding Assay The assays were conducted in a standard black 384-well polystyrene plate with a final volume of 20 µL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 µL was added to the plate well. Plates were centrifuged and proteins were preincubated with inhibitors for 40 minutes. The incubation was followed by the addition of 10 µL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHERAstar FS plate reader (665 nm/620 nm ratio). Final concentrations in the assay were—3 nM PD1, 10 nM PD-L1, 1 nM europium anti-human IgG and 20 nM anti-His-Allophycocyanin. $IC_{50}$ determination was performed by fitting the curve of percent control activity versus the log of the inhibitor concentration using the GraphPad Prism 5.0 software.

Example B. Src Homology Region 2 Domain-Containing Phosphatase (SHP) Assay

U2OS/PD-L1 cells (DiscoveRx Corporation) were maintained in McCoy's 5A medium with addition of 10% FBS, 0.25 µg/ml Puromycin. After removing the culture media, the cell medium was replaced with assay medium (RPMI1640 medium with 1% FBS). The U2OS/PD-L1 cells were then added in 384-well black clear bottom assay plate (CELLCOAT® Tissue Culture Plates, Greiner Bio-One) at 5000 cells per well in 20 µL assay medium. Test compounds were prepared by serial dilution in DMSO and 125 nL compound were first transferred to the 384 REMP plate well (Thermofisher) by ECHO liquid handler (Labcyte) followed with addition of 27.5 µL assay medium. 5 µL/well compounds in the assay medium were transferred to the cell plate with 0.05% DMSO in the final assay at 0.25 Jurkat-PD-1-SHP cells (DiscoveRx Corporation) were cultured in RPMI1640 medium supplemented with 10% FBS, 250 µg/ml Hygromycin B, 500 µg/ml G418. After the replacement of culture media with assay medium, 5,000 Jurkat-PD-1-SHP cells in 20 µL were dispensed into each well. The assay plate was incubated at 37° C., 5% $CO_2$ for 2 hours before 2.5 µL PathHunter reagent 1 (DiscoveRx Corporation) were added to each well. The assay plate was shaken for 1 min at 350 rpm in the dark followed with addition of 10 µL PathHunter reagent 2 (DiscoveRx Corporation). Chemiluminescent signal was recorded with TopCount reader (Perkin Elmer) after incubation at room temperature for 1 hour. Wells with DMSO were served as the positive controls and wells containing no cells were used as negative controls. $IC_{50}$ determination was performed by fitting the curve of percentage of control activity versus the log of the compound concentration using the GraphPad Prism 6.0 software.

Example C. Nuclear Factor of Activated T-Cells (NFAT) Assay

PD-L1 aAPC/CHO-K1 cells (Promega) were maintained in F-12 medium with addition of 10% FBS, 200 µg/ml Hygromycin B, 250 µg/ml Geneticin (G418). Jurkat-PD-1-NFAT effector cells (Promega) were cultured in RPMI 1640 medium supplemented with 10% FBS, 100 µg/ml Hygromycin B, 500 µg/ml G418. The culture media of PD-L1 aAPC/CHO-K1 cells were first replaced with assay medium (RPMI1640 medium with 1% FBS). The PD-L1 aAPC/CHO-K1 cells were then added in a white 384-well white clear bottom assay plate (CELLCOAT® Tissue Culture Plates, Greiner Bio-One) at 8000 per well in 10 µL assay medium. Test compounds were prepared by serial dilution in DMSO and 0.8 µL test compounds in DMSO were first transferred to the 384 REMP plate well (Thermofisher) by PlateMate Plus (Thermofisher) followed with addition of 50 µL plating medium. 5 µL compounds in the assay medium were transferred to the cells with 0.4% DMSO in the final assay at 2 µM After removing the culture media, 10,000 Jurkat-PD-1-NFAT effector cells in 5 µL assay medium was dispensed into each well. The assay plate was incubated at 37° C., 5% $CO_2$ for 24 hours. After the assay plate was equilibrated to room temp for 15 minutes, 20 µL/well of Bio-Glo™ reagent (Promega) were added. After 8 minutes incubation at room temperature, luminescence was read at with Pherastar microplate reader (BMG Labtech). The fold of induction (FOI) was calculated based on the ratio of luminescence normalized to the DMSO wells within each assay plate. The maximum percentage of induction was reported based on the ratio between the highest FOI of each compound and the maximum FOI of control compound within each assay plate. Wells with DMSO were served as the negative controls and wells containing control compound with the highest FOI were used as positive controls. EC50 determination was performed by fitting the curve of percent control activity versus the log of the compound concentration using the GraphPad Prism 6.0 software.

Example D. PD-L1 Whole Blood Internalization Assay

To determine PD-L1 internalization in human whole blood, normal human blood (Biological Specialty Corp, Colmar. Pa.) was incubated in the presence or absence of a concentration range of test compounds and 1 ng/ml human interferon γ (R&D Systems Inc. Minn. Minn.) in a 96 well "2 ml Assay Block" (Corning, Corning N.Y.) for 18-20 hours at 37° C. Blood was then stained with PD-L1 (MIH1, eBioscience; or BD Biosciences San Jose, Calif.), CD14 (Life Technologies, Carlsbad, Calif.) for 30 minutes in the dark at room temperature. Whole Blood/red cells were lysed/fixed (lysis buffer BD Biosciences) for 5 minutes at 37° C. in the dark and then centrifuged at 1600 RPM for 5 minutes. Cells were resuspended in Stain Buffer (BD Bioscience, San Jose, Calif.) and transferred into 96 well round bottom plates (Corning). Cells were gated on CD14+ (BD Biosciences) and PD-L1 expression determined by mean fluorescence intensity (MFI) (BD LSRFortessa™ X-20).

$IC_{50}$ determination was performed by fitting the curve of compound percent inhibition versus the log of the compound concentration using the GraphPad Prism 7.0 software.

Example E. In Vivo Pharmacokinetics in Rats, Monkeys and Dogs

For in vivo pharmacokinetic experiments, test compounds are administered to male Sprague Dawley rats, male beagle dogs, or male and female Cynomolgus monkeys intravenously or via oral gavage. For IV dosing, test compounds are dosed at 0.5 to 1 mg/kg using a formulation of 10% dimethylacetamide (DMAC) in acidified saline via IV bolus for rat and 5 min or 10 min IV infusion for dog and monkey respectively. For oral dosing, test compounds are dosed at 1.0 to 3.0 mg/kg using 5% DMAC in 0.5% methylcellulose in citrate buffer (pH 3.5). Blood samples are collected at predose and various time points up to 24 hours postdose. All blood samples are collected using EDTA as the anticoagulant and centrifuged to obtain plasma samples. The plasma concentrations of test compounds are determined by LC-MS methods. The measured plasma concentrations are used to calculate PK parameters by standard noncompartmental methods using Phoenix® WinNonlin software program (version 7.0, Pharsight Corporation).

In rats and monkeys, cassette dosing of test compounds are conducted to obtain preliminary PK parameters.

Example F. Results

Compounds of the present disclosure, as exemplified in Examples 1-66, were assessed in each of the HTRF PD-1/PD-L1 binding assay (Example A), SHP assay (Example B), NFAT assay (Example C), and whole blood internalization assay (Example D). The cutoffs for ranges of values observed in each of the assays are shown. The results obtained for the tested compounds are shown in Table 15.

| Cutoffs | + | ++ | +++ |
|---|---|---|---|
| HTRF binding assay $IC_{50}$ (nM) | <=5 nM | >5 to <=10 | >10 to <=100 |
| SHP Assay $IC_{50}$ (nM) | <=10 nM | >10 to <=100 | >100 to <=500 |
| NFAT assay $EC_{50}$ (nM) | <=10 nM | >10 to <=100 | >100 to <=500 |
| whole blood internalization assay $IC_{50}$ (nM) | <=10 nM | >10 to <=100 | >100 to <=500 |

TABLE 15

| Example | HTRF binding $IC_{50}$ (nM) | SHP $IC_{50}$ (nM) | NFAT $EC_{50}$ (nM) | Whole Blood (24 HR) $IC_{50}$ (nM) |
|---|---|---|---|---|
| 1 | + | + | ++ | + |
| 2 | + | + | ++ | ++ |
| 3 | + | + | ++ | |
| 4 | + | + | ++ | |
| 5 | + | + | + | |
| 6 | + | + | ++ | |
| 7 | + | | ++ | ++ |
| 8 | + | + | ++ | +++ |
| 9 | + | + | ++ | ++ |
| 10 | + | + | ++ | ++ |
| 11 | ++ | ++ | ++ | +++ |
| 12 | + | + | ++ | ++ |
| 13 | + | + | + | ++ |
| 14 | + | + | ++ | ++ |
| 15 | + | + | ++ | ++ |
| 16 | + | + | + | ++ |
| 17 | + | + | ++ | ++ |
| 18 | + | + | ++ | ++ |
| 19 | + | + | ++ | ++ |
| 20 | + | + | ++ | ++ |
| 21 | + | + | ++ | ++ |
| 22 | + | + | ++ | ++ |
| 23 | + | + | ++ | +++ |
| 24 | + | + | ++ | ++ |
| 25 | + | ++ | ++ | +++ |
| 26 | + | + | ++ | |
| 27 | + | + | ++ | ++ |
| 28 | + | | ++ | ++ |
| 29 | + | + | ++ | |
| 30 | + | + | ++ | ++ |
| 31 | + | + | ++ | ++ |
| 32 | + | | ++ | ++ |
| 33 | + | | ++ | ++ |
| 34 | + | + | ++ | ++ |
| 35 | + | ++ | +++ | +++ |
| 36 | + | + | ++ | ++ |
| 37 | + | + | ++ | ++ |
| 38 | + | + | ++ | ++ |
| 39 | + | + | ++ | |
| 40 | + | + | ++ | ++ |
| 41 | + | + | ++ | ++ |
| 42 | + | + | ++ | ++ |
| 43 | + | + | ++ | ++ |
| 44 | + | + | ++ | +++ |
| 45 | ++ | + | ++ | +++ |
| 46 | + | + | ++ | |
| 47 | + | | ++ | |
| 48 | + | + | ++ | |
| 49 | + | | ++ | |
| 50 | + | | ++ | |
| 51 | + | + | ++ | ++ |
| 52 | + | ++ | +++ | |
| 53 | + | + | ++ | |
| 54 | + | + | ++ | +++ |
| 55 | + | + | ++ | |
| 56 | + | + | ++ | +++ |
| 57 | + | + | ++ | ++ |
| 58 | + | + | ++ | +++ |
| 59 | + | + | +++ | |
| 60 (compound 1) | + | + | + | ++ |
| 60 (compound 2) | + | + | + | ++ |
| 61 (compound 1) | + | + | ++ | ++ |
| 61 (compound 2) | + | + | ++ | ++ |
| 62 | + | + | ++ | ++ |
| 63 | + | + | ++ | ++ |
| 64 | + | | + | ++ |
| 65 | + | + | ++ | ++ |
| 66 | + | + | + | ++ |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of Formula I:

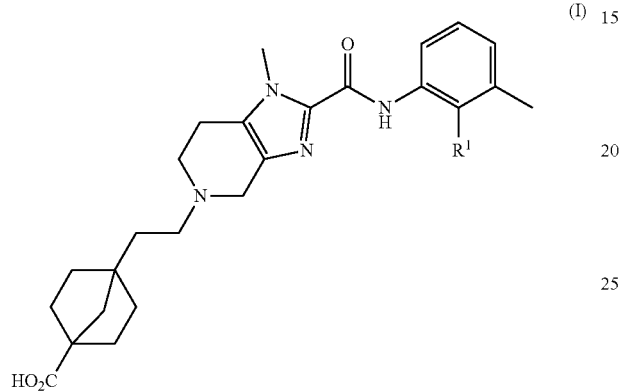

(I)

2. A compound of Formula I:

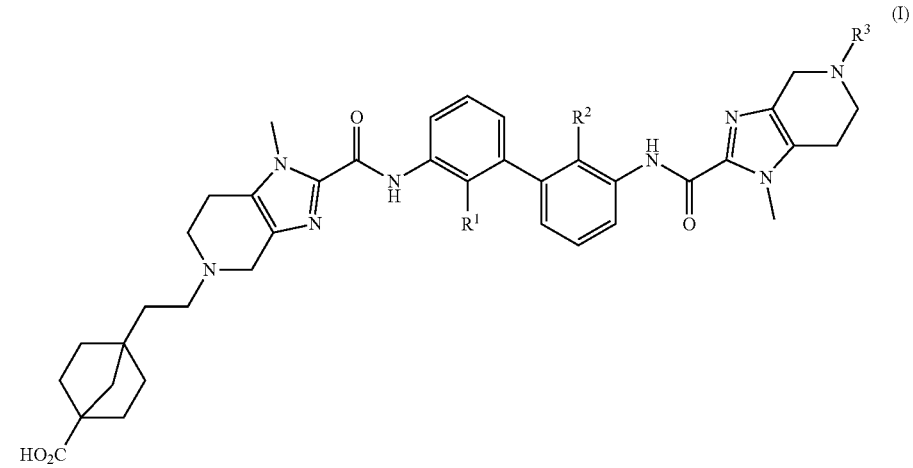

(I)

$R^3$ is H, $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl or 4- to 6-membered heterocycloalkyl-$C_{1-2}$ alkyl-, wherein the 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- of $R^3$ are each optionally substituted with 1 or 2 substituents independently selected from $CONH_2$, $SO_2NH_2$, $COOH$, $OH$, $CON(CH_3)_2$, $CH_3$, F, Cl, Br, CN, ethyl, and propyl.

-continued

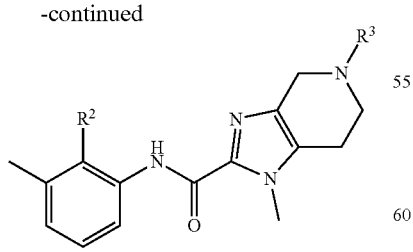

or a pharmaceutically acceptable salt or a stereoisomer thereof, wherein:
$R^1$ is methyl, CN, F, Cl, or Br;
$R^2$ is methyl, CN, F, Cl, or Br; and or a pharmaceutically acceptable salt or a stereoisomer thereof, wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl, $C_{6-10}$ aryl-$C_{1-2}$ alkyl, 5- to 6-membered heteroaryl, 5- to 6-membered heteroaryl-$C_{1-2}$ alkyl, 4- to 6-membered heterocycloalkyl or 4- to 6-membered heterocycloalkyl-$C_{1-2}$ alkyl-, wherein the 5- to 6-membered heteroaryl, 5- to 6-membered heteroaryl-$C_{1-2}$ alkyl, 4- to 6-membered heterocycloalkyl and 4- to 6-membered heterocycloalkyl-$C_{1-2}$ alkyl- each has one or two heteroatoms as ring members selected from O, N and S, and wherein the $C_{1-4}$ alkyl, $C_{3-8}$ cycloalkyl, $C_{3-8}$ cycloalkyl-C$_{1-2}$ alkyl-, C$_{6-10}$ aryl, C$_{6-10}$ aryl-C$_{1-2}$ alkyl, 5- to 6-membered heteroaryl, 5- to 6-membered heteroaryl-C$_{1-2}$ alkyl, 4- to 6-membered heterocycloalkyl and 4- to 6-membered heterocycloalkyl-C$_{1-2}$ alkyl- of R$^3$ are each optionally substituted with 1 or 2 substituents independently selected from CONH$_2$, SO$_2$NH$_2$, COOH, and OH.

3. The compound of claim 1, or a pharmaceutically acceptable salt or a stereoisomer thereof, wherein R$^1$ is methyl, F, Cl, or Br.

4. The compound of claim 1, or a pharmaceutically acceptable salt or a stereoisomer thereof, wherein R$^1$ is methyl.

5. The compound of claim 1, or a pharmaceutically acceptable salt or a stereoisomer thereof, wherein R$^1$ is F, Cl, or Br.

6. The compound of claim 1, or a pharmaceutically acceptable salt or a stereoisomer thereof, wherein R$^1$ is Cl.

7. The compound of claim 1, or a pharmaceutically acceptable salt or a stereoisomer thereof, wherein R$^2$ is methyl.

8. The compound of claim 1, or a pharmaceutically acceptable salt or a stereoisomer thereof, wherein R$^2$ is CN.

9. The compound of claim 1, or a pharmaceutically acceptable salt or a stereoisomer thereof, wherein R$^2$ is F, Cl, or Br.

10. The compound of claim 1, or a pharmaceutically acceptable salt or a stereoisomer thereof, wherein R$^2$ is Cl.

11. The compound of claim 1, or a pharmaceutically acceptable salt or a stereoisomer thereof, wherein R$^1$ is Cl and R$^2$ is Cl.

12. The compound of claim 1, or a pharmaceutically acceptable salt or a stereoisomer thereof, wherein R$^1$ is Cl and R$^2$ is methyl.

13. The compound of claim 1, or a pharmaceutically acceptable salt or a stereoisomer thereof, wherein R$^1$ is methyl and R$^2$ is Cl.

14. The compound of claim 1, or a pharmaceutically acceptable salt or a stereoisomer thereof, wherein R$^1$ is Cl and R$^2$ is CN.

15. The compound of claim 1, or a pharmaceutically acceptable salt or a stereoisomer thereof, wherein R$^1$ is methyl and R$^2$ is methyl.

16. The compound of claim 1, or a pharmaceutically acceptable salt or a stereoisomer thereof, wherein R$^3$ is H, C$_{1-4}$ alkyl, C$_{3-8}$ cycloalkyl, C$_{3-8}$ cycloalkyl-C$_{1-2}$ alkyl-, C$_{6-10}$ aryl-C$_{1-2}$ alkyl, 5- to 6-membered heteroaryl-C$_{1-2}$ alkyl, or 4- to 6-membered heterocycloalkyl, wherein the 5- to 6-membered heteroaryl-C$_{1-2}$ alkyl and 4- to 6-membered heterocycloalkyl each has one or two heteroatoms as ring members selected from O, N and S, and wherein the C$_{1-4}$ alkyl, C$_{3-8}$ cycloalkyl, C$_{3-8}$ cycloalkyl-C$_{1-2}$ alkyl-, C$_{6-10}$ aryl-C$_{1-2}$ alkyl, 5- to 6-membered heteroaryl-C$_{1-2}$ alkyl, and 4- to 6-membered heterocycloalkyl of R$^3$ are each optionally substituted with 1 or 2 substituents independently selected from CONH$_2$, SO$_2$NH$_2$, COOH, OH, CON(CH$_3$)$_2$, and CH$_3$.

17. The compound of claim 1, or a pharmaceutically acceptable salt or a stereoisomer thereof, wherein R$^3$ is H, C$_{1-4}$ alkyl, C$_{3-8}$ cycloalkyl, C$_{3-8}$ cycloalkyl-C$_{1-2}$ alkyl-, C$_{6-10}$ aryl-C$_{1-2}$ alkyl, 5- to 6-membered heteroaryl-C$_{1-2}$ alkyl, or 4- to 6-membered heterocycloalkyl, wherein the 5- to 6-membered heteroaryl-C$_{1-2}$ alkyl and 4- to 6-membered heterocycloalkyl each has one or two heteroatoms as ring members selected from O, N and S, and wherein the C$_{1-4}$ alkyl, C$_{3-8}$ cycloalkyl, C$_{3-8}$ cycloalkyl-C$_{1-2}$ alkyl-, C$_{6-10}$ aryl-C$_{1-2}$ alkyl, 5- to 6-membered heteroaryl-C$_{1-2}$ alkyl, and 4- to 6-membered heterocycloalkyl of R$^3$ are each optionally substituted with 1 or 2 substituents independently selected from CONH$_2$, SO$_2$NH$_2$, COOH, and OH.

18. The compound of claim 1, or a pharmaceutically acceptable salt or a stereoisomer thereof, wherein R$^3$ is H.

19. The compound of claim 1, or a pharmaceutically acceptable salt or a stereoisomer thereof, wherein R$^3$ is C$_{1-4}$ alkyl, optionally substituted with 1 or 2 substituents independently selected from COOH, OH, and CON(CH$_3$)$_2$.

20. The compound of claim 1, or a pharmaceutically acceptable salt or a stereoisomer thereof, wherein R$^3$ is C$_{1-4}$ alkyl, optionally substituted with 1 or 2 substituents independently selected from COOH and OH.

21. The compound of claim 1, or a pharmaceutically acceptable salt or a stereoisomer thereof, wherein R$^3$ is methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, or 4-carboxybutyl.

22. The compound of claim 1, or a pharmaceutically acceptable salt or a stereoisomer thereof, wherein R$^3$ is methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl or 2-carboxy-2-methylpropyl.

23. The compound of claim 1, or a pharmaceutically acceptable salt or a stereoisomer thereof, wherein R$^3$ is C$_{3-8}$ cycloalkyl, optionally substituted with 1 or 2 substituents independently selected from COOH, OH, and CH$_3$.

24. The compound of claim 1, or a pharmaceutically acceptable salt or a stereoisomer thereof, wherein R$^3$ is C$_{3-8}$ cycloalkyl, optionally substituted with 1 or 2 substituents independently selected from COOH and OH.

25. The compound of claim 1, or a pharmaceutically acceptable salt or a stereoisomer thereof, wherein R$^3$ is C$_{3-8}$ cycloalkyl-C$_{1-2}$ alkyl-, optionally substituted with 1 or 2 substituents independently selected from COOH and OH.

26. The compound of claim 1, or a pharmaceutically acceptable salt or a stereoisomer thereof, wherein R$^3$ is C$_{6-10}$ aryl-C$_{1-2}$ alkyl, optionally substituted with 1 or 2 substituents independently selected from COOH and OH.

27. The compound of claim 1, or a pharmaceutically acceptable salt or a stereoisomer thereof, wherein R$^3$ is cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (4-carboxycyclohexyl)ethyl, or 4-carboxy-4-methylcyclohexyl.

28. The compound of claim 1, or a pharmaceutically acceptable salt or a stereoisomer thereof, wherein R$^3$ is cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, or 4-carboxyphenethyl.

29. The compound of claim 1, or a pharmaceutically acceptable salt or a stereoisomer thereof, wherein R$^3$ is 5- to 6-membered heteroaryl-C$_{1-2}$ alkyl, optionally substituted with 1 or 2 substituents independently selected from CONH$_2$, SO$_2$NH$_2$, and COOH.

30. The compound of claim 1, or a pharmaceutically acceptable salt or a stereoisomer thereof, wherein R$^3$ is 4- to 6-membered heterocycloalkyl, optionally substituted with 1 or 2 substituents independently selected from CONH$_2$, SO$_2$NH$_2$, and COOH.

31. The compound of claim 1, or a pharmaceutically acceptable salt or a stereoisomer thereof, wherein $R^3$ is (1H-pyrazol-3-yl)methyl, tetrahydro-2H-pyran-4-yl, 1-carbamoylpiperidin-4-yl, 1-sulfamoylpiperidin-4-yl, or (3-carboxy-1H-pyrazol-5-yl)methyl.

32. The compound of claim 1, or a pharmaceutically acceptable salt or a stereoisomer thereof, wherein $R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, (3-carboxy-1H-pyrazol-5-yl)methyl, 4-carboxybutyl, (4-carboxycyclohexyl)ethyl, or 4-carboxy-4-methylcyclohexyl.

33. The compound of claim 1, or a pharmaceutically acceptable salt or a stereoisomer thereof, wherein $R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, or (3-carboxy-1H-pyrazol-5-yl)methyl.

34. The compound of claim 1, or a pharmaceutically acceptable salt or a stereoisomer thereof, wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, OH, $CON(CH_3)_2$, and $CH_3$.

35. The compound of claim 1, or a pharmaceutically acceptable salt or a stereoisomer thereof, wherein:
$R^1$ is methyl, CN, F, Cl, or Br;
$R^2$ is methyl, CN, F, Cl, or Br; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, and OH.

36. The compound of claim 1, or a pharmaceutically acceptable salt or a stereoisomer thereof, wherein:
$R^1$ is methyl or Cl;
$R^2$ is methyl, CN, or Cl; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, OH, $CON(CH_3)_2$, and $CH_3$.

37. The compound of claim 1, or a pharmaceutically acceptable salt or a stereoisomer thereof, wherein:
$R^1$ is methyl or Cl;
$R^2$ is methyl, CN, or Cl; and
$R^3$ is H, $C_{1-4}$ alkyl, $C_{3-8}$ cycloalkyl, $C_{3-8}$ cycloalkyl-$C_{1-2}$ alkyl-, $C_{6-10}$ aryl-$C_{1-2}$ alkyl, 5- to 6-membered heteroaryl-$C_{1-2}$ alkyl, or 4- to 6-membered heterocycloalkyl, wherein the 5- to 6-membered heteroaryl-$C_{1-2}$ alkyl and 4- to 6-membered heterocycloalkyl each has one or two heteroatoms as ring members selected from O, N and S, and wherein the $C_{1-4}$ alkyl, $C_{3-8}$ cycloalkyl, $C_{3-8}$ cycloalkyl-$C_{1-2}$ alkyl-, $C_{6-10}$aryl-$C_{1-2}$ alkyl, 5- to 6-membered heteroaryl-$C_{1-2}$ alkyl, and 4- to 6-membered heterocycloalkyl of $R^3$ are each optionally substituted with 1 or 2 substituents independently selected from $CONH_2$, $SO_2NH_2$, COOH, and OH.

38. The compound of claim 1, or a pharmaceutically acceptable salt or a stereoisomer thereof, wherein:
$R^1$ is methyl or Cl;
$R^2$ is methyl, CN, or Cl; and
$R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, (3-carboxy-1H-pyrazol-5-yl)methyl, 4-carboxybutyl, (4-carboxycyclohexyl)ethyl, or 4-carboxy-4-methylcyclohexyl.

39. The compound of claim 1, or a pharmaceutically acceptable salt or a stereoisomer thereof, wherein:
$R^1$ is methyl or Cl;
$R^2$ is methyl, CN, or Cl; and
$R^3$ is H, methyl, ethyl, isopropyl, 1,3-dihydroxypropan-2-yl, 2,3-dihydroxypropyl, 2-hydroxypropyl, 2-hydroxyethyl, 3-hydroxypropyl, carboxymethyl, 3-carboxypropyl, 2-carboxy-2-methylpropyl, cyclobutyl, 4-hydroxycyclohexyl, (1-carboxycyclopropyl)methyl, (4-carboxybicyclo[2.2.1]heptan-1-yl)ethyl, (4-carboxybicyclo[2.2.1]heptan-1-yl)methyl, (4-carboxybicyclo[2.2.2]octan-1-yl)methyl, (3-carboxybicyclo[1.1.1]pentan-1-yl)methyl, 4-carboxyphenethyl, (1H-pyrazol-3-yl)methyl, tetrahydro-2H-pyran-4-yl, 1-carbamoylpiperidin-4-yl, 1-sulfamoylpiperidin-4-yl, or (3-carboxy-1H-pyrazol-5-yl)methyl.

40. A pharmaceutical composition comprising a compound of claim 1, or a pharmaceutically acceptable salt or a stereoisomer thereof, and a pharmaceutically acceptable excipient or carrier.

41. A pharmaceutical composition comprising a compound of claim 20, or a pharmaceutically acceptable salt or a stereoisomer thereof, and a pharmaceutically acceptable excipient or carrier.

* * * * *